(12) United States Patent
Liu et al.

(10) Patent No.: US 9,434,774 B2
(45) Date of Patent: Sep. 6, 2016

(54) PROTEIN SURFACE REMODELING

(75) Inventors: David R. Liu, Lexington, MA (US);
Kevin John Phillips, Somerville, MA (US); Michael S. Lawrence, Atkinson, NH (US)

(73) Assignee: President and Fellows of Harvard College, Cambridge, MA (US)

( * ) Notice: Subject to any disclaimer, the term of this patent is extended or adjusted under 35 U.S.C. 154(b) by 0 days.

(21) Appl. No.: 13/341,231

(22) Filed: Dec. 30, 2011

(65) Prior Publication Data
US 2012/0129759 A1 May 24, 2012

Related U.S. Application Data

(63) Continuation of application No. 12/303,047, filed as application No. PCT/US2007/070254 on Jun. 1, 2007, now Pat. No. 9,150,626.

(60) Provisional application No. 60/810,364, filed on Jun. 2, 2006, provisional application No. 60/836,607, filed on Aug. 9, 2006.

(51) Int. Cl.
*C07K 17/00* (2006.01)
*C07K 14/435* (2006.01)
*C12N 9/00* (2006.01)

(52) U.S. Cl.
CPC ........... *C07K 14/43595* (2013.01); *C12N 9/93* (2013.01); *C12Y 603/02003* (2013.01)

(58) Field of Classification Search
None
See application file for complete search history.

(56) References Cited

U.S. PATENT DOCUMENTS

| 4,270,537 A | 6/1981 | Romaine |
| 4,596,556 A | 6/1986 | Morrow et al. |
| 4,790,824 A | 12/1988 | Morrow et al. |
| 4,886,499 A | 12/1989 | Cirelli et al. |
| 4,940,460 A | 7/1990 | Casey et al. |
| 4,941,880 A | 7/1990 | Burns |
| 5,015,235 A | 5/1991 | Crossman |
| 5,064,413 A | 11/1991 | McKinnon et al. |

(Continued)

FOREIGN PATENT DOCUMENTS

| WO | WO 91/00345 | 1/1991 |
| WO | WO 97/13537 | 4/1997 |

(Continued)

OTHER PUBLICATIONS

Strickler et al. (Biochemistry, 2006, 45(9), 2761-2766).*

(Continued)

*Primary Examiner* — Larry D Riggs, III
(74) *Attorney, Agent, or Firm* — Wolf, Greenfield & Sacks, P.C.

(57) ABSTRACT

Aggregation is a major cause of the misbehavior of proteins. A system for modifying a protein to create a more stable variant is provided. The method involves identifying non-conserved hydrophobic amino acid residues on the surface of a protein, suitable for mutating to more hydrophilic residues (e.g., charged amino acids). Any number of residues on the surface may be changed to create a variant that is more soluble, resistant to aggregation, has a greater ability to re-fold, and/or is more stable under a variety of conditions. The invention also provides GFP, streptavidin, and GST variants with an increased theoretical net charge created by the inventive technology. Kits are also provided for carrying out such modifications on any protein of interest.

26 Claims, 6 Drawing Sheets

(56) References Cited

U.S. PATENT DOCUMENTS

| | | | |
|---|---|---|---|
| 5,141,496 | A | 8/1992 | Dalto et al. |
| 5,190,521 | A | 3/1993 | Hubbard et al. |
| 5,258,453 | A | 11/1993 | Kopecek et al. |
| 5,312,335 | A | 5/1994 | McKinnon et al. |
| 5,328,483 | A | 7/1994 | Jacoby |
| 5,334,144 | A | 8/1994 | Alchas et al. |
| 5,339,163 | A | 8/1994 | Homma et al. |
| 5,383,851 | A | 1/1995 | McKinnon, Jr. et al. |
| 5,417,662 | A | 5/1995 | Hjertman et al. |
| 5,466,220 | A | 11/1995 | Brenneman |
| 5,480,381 | A | 1/1996 | Weston |
| 5,503,627 | A | 4/1996 | McKinnon et al. |
| 5,520,639 | A | 5/1996 | Peterson et al. |
| 5,527,288 | A | 6/1996 | Gross et al. |
| 5,569,189 | A | 10/1996 | Parsons |
| 5,574,142 | A | 11/1996 | Meyer, Jr. et al. |
| 5,599,302 | A | 2/1997 | Lilley et al. |
| 5,649,912 | A | 7/1997 | Peterson |
| 5,704,911 | A | 1/1998 | Parsons |
| 5,893,397 | A | 4/1999 | Peterson et al. |
| 5,977,089 | A | 11/1999 | Arimilli et al. |
| 5,993,412 | A | 11/1999 | Deily et al. |
| 6,005,087 | A | 12/1999 | Cook et al. |
| 6,031,086 | A | 2/2000 | Switzer |
| 6,127,533 | A | 10/2000 | Cook et al. |
| 6,225,460 | B1 | 5/2001 | Bischofberger et al. |
| 6,399,754 | B1 | 6/2002 | Cook |
| 6,403,779 | B1 | 6/2002 | Kawasaki et al. |
| 7,241,869 | B2 * | 7/2007 | Springer et al. ............... 530/350 |
| 7,252,960 | B2 | 8/2007 | Yamada et al. |
| 7,271,241 | B2 | 9/2007 | Waldo |
| 7,306,937 | B2 * | 12/2007 | Poulose et al. ............... 435/219 |
| 7,417,131 | B2 | 8/2008 | Lukyanov |
| 8,450,279 | B2 | 5/2013 | Jo et al. |
| 9,150,626 | B2 | 10/2015 | Liu et al. |
| 9,221,886 | B2 | 12/2015 | Liu et al. |
| 2003/0134352 | A1 | 7/2003 | Freimuth et al. |
| 2003/0175950 | A1 | 9/2003 | McSwiggen |
| 2003/0236214 | A1 | 12/2003 | Wolff et al. |
| 2004/0092470 | A1 | 5/2004 | Leonard et al. |
| 2004/0102606 | A1 | 5/2004 | Balicki et al. |
| 2004/0110928 | A1 | 6/2004 | Crisanti et al. |
| 2004/0162235 | A1 | 8/2004 | Trubetskoy et al. |
| 2004/0176282 | A1 | 9/2004 | Dalby et al. |
| 2004/0192626 | A1 | 9/2004 | McSwiggen et al. |
| 2004/0215400 | A1 | 10/2004 | Slovic et al. |
| 2005/0020525 | A1 | 1/2005 | McSwiggen et al. |
| 2005/0032733 | A1 | 2/2005 | McSwiggen et al. |
| 2005/0059005 | A1 | 3/2005 | Tuschl et al. |
| 2005/0119181 | A1 | 6/2005 | Pepinsky et al. |
| 2005/0260192 | A1 | 11/2005 | Springer et al. |
| 2007/0105182 | A1 | 5/2007 | Raines et al. |
| 2009/0142820 | A1 | 6/2009 | Bradbury et al. |
| 2010/0209994 | A1 | 8/2010 | Liu et al. |
| 2011/0112040 | A1 | 5/2011 | Liu et al. |
| 2012/0100569 | A1 | 4/2012 | Liu et al. |

FOREIGN PATENT DOCUMENTS

| | | |
|---|---|---|
| WO | WO 97/37705 | 10/1997 |
| WO | WO 99/34850 | 7/1999 |
| WO | WO 02/18583 A2 | 3/2002 |
| WO | WO 2005/000097 A2 | 1/2005 |
| WO | WO 2005/035559 A1 | 4/2005 |
| WO | WO 05/078074 | 8/2005 |
| WO | WO 07/143574 | 12/2007 |
| WO | WO 2008/054544 A2 | 5/2008 |
| WO | WO 09/116984 | 9/2009 |
| WO | WO 09/134808 | 11/2009 |

OTHER PUBLICATIONS

U.S. Appl. No. 61/507,897, filed Jul. 14, 2011, Liu.
Supplementary European Search Report for 07784283.9 mailed Oct. 12, 2009.
International Search Report and Written Opinion for PCT/US2007/070254 mailed Nov. 8, 2007.
International Preliminary Report on Patentability for PCT/US2007/070254 mailed Dec. 18, 2008.
Invitation to Pay Additional Fees for PCT/US2009/041984 mailed Jan. 27, 2010.
International Search Report and Written Opinion for PCT/US2009/041984 mailed Apr. 20, 2010.
International Preliminary Report on Patentability for PCT/US2009/041984 mailed Nov. 11, 2010.
International Search Report and Written Opinion for PCT/US2010/001250 mailed Apr. 12, 2011.
International Preliminary Report on Patentability for PCT/US2010/001250 mailed Nov. 10, 2011.
GENBANK Submission; NIH/NCBI, Accession No. P42212, Prasher et al.; Mar. 21, 2006.
UniProtKB/Swiss-Prot O75925: Liu et al.: Dec. 14, 2011.
UniProtKB/Swiss-Prot O75683: Magoulas et al.: Sep. 21, 2011.
UniProtKB/Swiss-Prot P05412: Hattori et al.: Dec. 14, 2011.
UniProtKB/Swiss-Prot P09429: Wen et al.: Dec. 14, 2011.
UniProtKB/Swiss-Prot P12034: Haub et al.: Dec. 14, 2011.
UniProtKB/Swiss-Prot P12956: Chan et al.: Dec. 14, 2011.
UniProtKB/Swiss-Prot P14210: Miyazawa et al.: Dec. 14, 2011.
UniProtKB/Swiss-Prot P16401: Albig et al.: Dec. 14, 2011.
UniProtKB/Swiss-Prot P18509: Ohkubo et al.: Dec. 14, 2011.
UniProtKB/Swiss-Prot P21741: Tsutsui et al.: Dec. 14, 2011.
UniProtKB/Swiss-Prot P35659: von Lindern et al.: Dec. 14, 2011.
UniProtKB/Swiss-Prot P36578: Bagni et al.: Dec. 14, 2011.
UniProtKB/Swiss-Prot P41218: Briggs et al.: Dec. 14, 2011.
UniProtKB/Swiss-Prot P54274: Chong et al.: Dec. 14, 2011.
UniProtKB/Swiss-Prot P62805: Sierra et al.: Dec. 14, 2011.
UniProtKB/Swiss-Prot P81534: Harder et al.: Sep. 21, 2011.
UniProtKB/Swiss-Prot P83369: Ota et al.: Dec. 14, 2011.
UniProtKB/Swiss-Prot Q03164: Tkachuk et al.: Dec. 14, 2011.
UniProtKB/Swiss-Prot Q12796: Chen et al.: Dec. 14, 2011.
UniProtKB/Swiss-Prot Q13601: Gerhard et al.: Dec. 14, 2011.
UniProtKB/Swiss-Prot Q15287: Badolato et al.: Dec. 14, 2011.
UniProtKB/Swiss-Prot Q66PJ3: Mural et al.: Dec. 14, 2011.
UniProtKB/Swiss-Prot Q7L7LO: Marzluff et al.: Dec. 14, 2011.
UniProtKB/Swiss-Prot Q8N5F7: Chen et al.: Dec. 14, 2011.
UniProtKB/Swiss-Prot Q8N726: Stone et al.: Dec. 14, 2011.
UniProtKB/Swiss-Prot Q8N9Q2: Ota et al.: Dec. 14, 2011.
UniProtKB/Swiss-Prot Q8TDN6: Kaser et al.: Dec. 14, 2011.
UniProtKB/Swiss-Prot Q8WVK2: Nakamura et al.: Dec. 14, 2011.
UniProtKB/Swiss-Prot Q96FI4: Takao et al.: Dec. 14, 2011.
UniProtKB/Swiss-Prot Q9NWT8: Ota et al.: Dec. 14, 2011.
UniProtKB/Swiss-Prot Q99075: Higashiyama et al.: Dec. 14, 2011.
UniProtKB/Swiss-Prot Q99848: Shire et al.: Dec. 14, 2011.
UniProtKB/Swiss-Prot Q9H6F5: Hoshino et al.: Jan. 19, 2010.
UniProtKB/Swiss-Prot Q9HC23: Li et al.: Dec. 14, 2011.
UniProtKB/Swiss-Prot Q9UK58: Dickinson et al.: Dec. 14, 2011.
UniProtKB/Swiss-Prot Q9Y258: Guo et al.: Dec. 14, 2011.
Abremski et al., Studies on the properties of P1 site-specific recombination: evidence for topologically unlinked products following recombination. Cell. Apr. 1983;32(4):1301-11.
Akinc et al., A combinatorial library of lipid-like materials for delivery of RNAi therapeutics. Nat Biotechnol. May 2008;26(5):561-9. Epub Apr. 27, 2008.
Ali-Osman et al., Molecular cloning, characterization, and expression in *Escherichia coli* of full-length cDNAs of three human glutathione S-transferase Pi gene variants. Evidence for differential catalytic activity of the encoded proteins. J Biol Chem. Apr. 11, 1997;272(15):10004-12.
Altschul et al., Basic local alignment search tool. J Mol Biol. Oct. 5, 1990;215(3):403-10.
Anastassiadis et al., Dre recombinase, like Cre, is a highly efficient site-specific recombinase in *E. coli*, mammalian cells and mice. Dis Model Mech. Sep.-Oct. 2009;2(9-10):508-15. Epub Aug. 19, 2009.
Andrews et al., The rough energy landscape of superfolder GFP is linked to the chromophore. J Mol Biol. Oct. 19, 2007;373(2):476-90. Epub Aug. 15, 2007.

(56) References Cited

OTHER PUBLICATIONS

Apple et al., Cationization of protein antigens. IV. Increased antigen uptake by antigen-presenting cells. J Immunol. May 15, 1988;140(10):3290-5.
Atkinson et al., Delivering the goods: viral and non-viral gene therapy systems and the inherent limits on cargo DNA and internal sequences. Genetica. May 2010;138(5):485-98. Epub Jan. 19, 2010.
Atwell et al., Structural plasticity in a remodeled protein-protein interface. Science. Nov. 7, 1997;278(5340):1125-8.
Bae et al., Protective anti-tumour immune responses by murine dendritic cells pulsed with recombinant Tat-carcinoembryonic antigen derived from *Escherichia coli*. Clin Exp Immunol. Jul. 2009;157(1):128-38.
Baeuerle et al., Chlorate—a potent inhibitor of protein sulfation in intact cells. Biochem Biophys Res Commun. Dec. 15, 1986;141(2):870-7.
Baker et al., Electrostatics of nanosystems: application to microtubules and the ribosome. Proc Natl Acad Sci U S A. Aug. 28, 2001;98(18):10037-41. Epub Aug. 21, 2001.
Bartel, MicroRNAs: genomics, biogenesis, mechanism, and function. Cell. Jan. 23, 2004;116(2):281-97.
Beard et al., Efficient method to generate single-copy transgenic mice by site-specific integration in embryonic stem cells. Genesis. Jan. 2006;44(1):23-8.
Borodovsky et al., A novel active site-directed probe specific for deubiquitylating enzymes reveals proteasome association of USP14. EMBO J. Sep. 17, 2001;20(18):5187-96.
Boussif et al., A versatile vector for gene and oligonucleotide transfer into cells in culture and in vivo: polyethylenimine. Proc Natl Acad Sci U S A. Aug. 1, 1995;92(16):7297-301.
Brambrink et al., Sequential expression of pluripotency markers during direct reprogramming of mouse somatic cells. Cell Stem Cell. Feb. 7, 2008;2(2):151-9.
Brummelkamp et al., Stable suppression of tumorigenicity by virus-mediated RNA interference. Cancer Cell. Sep. 2002;2(3):243-7.
Brunet et al., the transcription factor Engrailed-2 guides retinal axons. Nature. Nov. 3, 2005;438(7064):94-8.
Bumcrot et al., RNAi therapeutics: a potential new class of pharmaceutical drugs. Nat Chem Biol. Dec. 2006;2(12):711-9.
Buskirk et al., Creating small-molecule-dependent switches to modulate biological functions. Chem Biol. Feb. 2005;12(2):151-61.
Buskirk et al., Directed evolution of ligand dependence: small-molecule-activated protein splicing. Proc Natl Acad Sci U S A. Jul. 20, 2004;101(29):10505-10. Epub Jul. 9, 2004.
Bystroff et al., Crystal structure of unliganded *Escherichia coli* dihydrofolate reductase. Ligand-induced conformational changes and cooperativity in binding. Biochemistry. Feb. 26, 1991;30(8):2227-39.
Cabantous et al., In vivo and in vitro protein solubility assays using split GFP. Nat Methods. Oct. 2006;3(10):845-54.
Cabantous et al., New molecular reporters for rapid protein folding assays. PLoS One. Jun. 11, 2008;3(6):e2387.
Cabantous et al., Protein tagging and detection with engineered self-assembling fragments of green fluorescent protein. Nat Biotechnol. Jan. 2005;23(1):102-7. Epub Dec. 5, 2004.
Cabantous et al., Recent advances in GFP folding reporter and split-GFP solubility reporter technologies. Application to improving the folding and solubility of recalcitrant proteins from *Mycobacterium tuberculosis*. J Struct Funct Genomics. 2005;6(2-3):113-9.
Cardoso et al., siRNA delivery by a transferrin-associated lipid-based vector: a non-viral strategy to mediate gene silencing. J Gene Med. Mar. 2007;9(3):170-83.
Carillo et al., The Multiple Sequence Alignment Problem in Biology. SIAM J Applied Math. 1988;48(5):1073-82.
Carlotti et al., Lentiviral vectors efficiently transduce quiescent mature 3T3-L1 adipocytes. Mol Ther. Feb. 2004;9(2):209-17.
Carroll, Zinc-finger nucleases as gene therapy agents. Gene Ther. Nov. 2008;15(22):1463-8. Epub Sep. 11, 2008.
Caron et al., Intracellular delivery of a Tat-eGFP fusion protein into muscle cells. Mol Ther. Mar. 2001;3(3):310-8.
Cava et al., Expression and use of superfolder green fluorescent protein at high temperatures in vivo: a tool to study extreme thermophile biology. Environ Microbiol. Mar. 2008;10(3):605-13. Epub Jan. 7, 2008.
Chakraborty, Potentiality of small interfering RNAs (siRNA) as recent therapeutic targets for gene-silencing. Curr Drug Targets. Mar. 2007;8(3):469-82.
Chandler et al., Targeting tumor cells via EGF receptors: selective toxicity of an HBEGF-toxin fusion protein. Int J Cancer. Sep. 25, 1998;78(1):106-11.
Charton et al., The structural dependence of amino acid hydrophobicity parameters. J Theor Biol. Dec. 21, 1982;99(4):629-44.
Chen et al., A general strategy for the evolution of bond-forming enzymes using yeast display. Proc Natl Acad Sci U S A. Jul. 12, 2011;108(28):11399-404. Epub Jun. 22, 2011.
Chen et al., HDAC4 regulates neuronal survival in normal and diseased retinas. Science. Jan. 9, 2009;323(5911):256-9.
Chiti et al., Protein misfolding, functional amyloid, and human disease. Annu Rev Biochem. 2006;75:333-66.
Chiti et al., Rationalization of the effects of mutations on peptide and protein aggregation rates. Nature. Aug. 14, 2003;424(6950):805-8.
Chiti et al., Studies of the aggregation of mutant proteins in vitro provide insights into the genetics of amyloid diseases. Proc Natl Acad Sci U S A. Dec. 10, 2002;99 Suppl 4:16419-26. Epub Oct. 8, 2002.
Chun et al., Split GFP complementation assay: a novel approach to quantitatively measure aggregation of tau in situ: effects of GSK3beta activation and caspase 3 cleavage. J Neurochem. Dec. 2007;103(6):2529-39. Epub Oct. 1, 2007.
Cioce et al., Hepatocyte growth factor (HGF)/NK1 is a naturally occurring HGF/scatter factor variant with partial agonist/antagonist activity. J Biol Chem. May 31, 1996;271(22):13110-5.
Clackson et al., A hot spot of binding energy in a hormone-receptor interface. Science. Jan. 20, 1995;267(5196):383-6.
Cohen et al., Therapeutic approaches to protein-misfolding diseases. Nature. Dec. 18, 2003;426(6968):905-9.
Cornette et al., Hydrophobicity scales and computational techniques for detecting amphipathic structures in proteins. J Mol Biol. Jun. 5, 1987;195(3):659-85.
Crameri et al., Improved green fluorescent protein by molecular evolution using DNA shuffling. Nat Biotechnol. Mar. 1996;14(3):315-9.
Cronican et al., A class of human proteins that deliver functional proteins into mammalian cells in vitro and in vivo. Chem Biol. Jul. 29, 2011;18(7):833-8.
Cronican et al., Potent delivery of functional proteins into Mammalian cells in vitro and in vivo using a supercharged protein. ACS Chem Biol. Aug. 20, 2010;5(8):747-52.
Czerwinski et al., Cytotoxic agents directed to peptide hormone receptors: defining the requirements for a successful drug. Proc Natl Acad Sci U S A. Sep. 29, 1998;95(20):11520-5.
Daniels et al., Intrinsically cell-permeable miniature proteins based on a minimal cationic PPII motif. J Am Chem Soc. Nov. 28, 2007;129(47):14578-9. Epub Nov. 6, 2007.
Darimont et al., Structure and specificity of nuclear receptor-coactivator interactions. Genes Dev. Nov. 1, 1998;12(21):3343-56.
Deshayes et al., Cell-penetrating peptides: tools for intracellular delivery of therapeutics. Cell Mol Life Sci. Aug. 2005;62(16):1839-49.
Deshayes et al., Chapter 11. Peptide-mediated delivery of nucleic acids into mammalian cells. Methods Mol Biol. 2007;386:299-308.
Devereux et al., A comprehensive set of sequence analysis programs for the VAX. Nucleic Acids Res. Jan. 11, 1984;12(1 Pt 1):387-95.
Dirr et al., Refined crystal structure of porcine class Pi glutathione S-transferase (pGST P1-1) at 2.1 A resolution. J Mol Biol. Oct. 14, 1994;243(1):72-92.
Domen et al., Cationization of protein antigens. III. Abrogation of oral tolerance. J Immunol. Nov. 15, 1987;139(10):3195-8.

(56) References Cited

OTHER PUBLICATIONS

Dorsett et al., siRNAs: applications in functional genomics and potential as therapeutics. Nat Rev Drug Discov. Apr. 2004;3(4):318-29.

Doudna et al., The chemical repertoire of natural ribozymes. Nature. Jul. 11, 2002;418(6894):2228.

Dubowchik et al., Cathepsin B-labile dipeptide linkers for lysosomal release of doxorubicin from internalizing immunoconjugates: model studies of enzymatic drug release and antigen-specific in vitro anticancer activity. Bioconjug Chem. Jul.-Aug. 2002;13(4):855-69.

Duncan et al., Degradation of side-chains of N-(2-hydroxypropyl)methacrylamide copolymers by lysosomal thiol-proteinases. Biosci Rep. Dec. 1982;2(12):1041-6.

Dykxhoorn et al., Killing the messenger: short RNAs that silence gene expression. Nat Rev Mol Cell Biol. Jun. 2003;4(6):457-67.

Elbashir et al., Duplexes of 21-nucleotide RNAs mediate RNA interference in cultured mammalian cells. Nature. May 24, 2001;411(6836):494-8.

Elbashir et al., Functional anatomy of siRNAs for mediating efficient RNAi in *Drosophila melanogaster* embryo lysate. EMBO J. Dec. 3, 2001;20(23):6877-88.

Elbashir et al., RNA interference is mediated by 21- and 22-nucleotide RNAs. Genes Dev. Jan. 15, 2001;15(2):188-200.

Elenius et al., Activation of HER4 by heparin-binding EGF-like growth factor stimulates chemotaxis but not proliferation. EMBO J. Mar. 17, 1997;16(6):1268-78.

Erbacher et al., Putative role of chloroquine in gene transfer into a human hepatoma cell line by DNA/lactosylated polylysine complexes. Exp Cell Res. May 25, 1996;225(1):186-94.

Fire et al., Potent and specific genetic interference by double-stranded RNA in Caenorhabditis elegans. Nature. Feb. 19, 1998;391(6669):806-11.

Fisher et al., Evaluating the specificity of antisense oligonucleotide conjugates. A DNA array analysis. J Biol Chem. Jun. 21, 2002;277(25):22980-4. Epub Apr. 10, 2002.

Fowler et al., Rational design of aggregation-resistant bioactive peptides: reengineering human calcitonin. Proc Natl Acad Sci U S A. Jul. 19, 2005;102(29):10105-10. Epub Jul. 8, 2005.

Frankel et al., Cellular uptake of the tat protein from human immunodeficiency virus. Cell. Dec. 23, 1988;55(6):1189-93.

Frokjaer et al., Protein drug stability: a formulation challenge. Nat Rev Drug Discov. Apr. 2005;4(4):298-306.

Fuchs et al., Arginine grafting to endow cell permeability. ACS Chem Biol. Mar. 20, 2007;2(3):167-70. Epub Feb. 23, 2007.

Fuchs et al., Increasing the potency of a cytotoxin with an arginine graft. Protein Eng Des Sel. Oct. 2007;20(10):505-9. Epub Oct. 22, 2007.

Fuchs et al., Pathway for polyarginine entry into mammalian cells. Biochemistry. Mar. 9, 2004;43(9):2438-44.

Futaki et al., Arginine-rich peptides. An abundant source of membrane-permeable peptides having potential as carriers for intracellular protein delivery. J Biol Chem. Feb. 23, 2001;276(8):5836-40. Epub Nov. 17, 2000.

Futaki et al., Structural variety of membrane permeable peptides. Curr Protein Pept Sci. Apr. 2003;4(2):87-96.

Futami et al., Preparation of potent cytotoxic ribonucleases by cationization: enhanced cellular uptake and decreased interaction with ribonuclease inhibitor by chemical modification of carboxyl groups. Biochemistry. Jun. 26, 2001;40(25):7518-24.

Gabel et al., Mannose 6-phosphate receptor-mediated endocytosis of acid hydrolases: internalization of beta-glucuronidase is accompanied by a limited dephosphorylation. J Cell Biol. Nov. 1986;103(5):1817-27.

Gampe et al., Asymmetry in the PPARgamma/RXRalpha crystal structure reveals the molecular basis of heterodimerization among nuclear receptors. Mol Cell. Mar. 2000;5(3):545-55.

Giepmans et al., The fluorescent toolbox for assessing protein location and function. Science. Apr. 14, 2006;312(5771):217-24.

Gitlin et al., Why are proteins charged? Networks of charge-charge interactions in proteins measured by charge ladders and capillary electrophoresis. Angew Chem Int Ed Engl. May 5, 2006;45(19):3022-60.

Glover et al., Crystal structure of the heterodimeric bZIP transcription factor c-Fos-c-Jun bound to DNA. Nature. Jan. 19, 1995;373(6511):257-61.

Goodchild, Hammerhead ribozymes: biochemical and chemical considerations. Curr Opin Mol Ther. Jun. 2000;2(3):272-81.

Green et al., Autonomous functional domains of chemically synthesized human immunodeficiency virus tat trans-activator protein. Cell. Dec. 23, 1988;55(6):1179-88.

Gregory et al., Chapter 3. MicroRNA biogenesis: isolation and characterization of the microprocessor complex. Methods Mol Biol. 2006;342:33-47.

Gudiksen et al., Eliminating positively charged lysine epsilon-NH3+ groups on the surface of carbonic anhydrase has no significant influence on its folding from sodium dodecyl sulfate. J Am Chem Soc. Apr. 6, 2005;127(13):4707-14.

Guo et al., Structure of Cre recombinase complexed with DNA in a site-specific recombination synapse. Nature. Sep. 4, 1997;389(6646):40-6.

Hamelryck et al., An amino acid has two sides: a new 2D measure provides a different view of solvent exposure. Proteins. Apr. 1, 2005;59(1):38-48.

Hammond et al., An RNA-directed nuclease mediates post-transcriptional gene silencing in *Drosophila* cells. Nature. Mar. 16, 2000;404(6775):293-6.

Hanna et al., Direct reprogramming of terminally differentiated mature B lymphocytes to pluripotency. Cell. Apr. 18, 2008;133(2):250-64.

Hansen et al., Predicting cell-penetrating peptides. Adv Drug Deliv Rev. Mar. 1, 2008;60(45):572-9. Epub Oct. 22, 2007.

Harder et al., Isolation and characterization of human beta-defensin-3, a novel human inducible peptide antibiotic. J Biol Chem. Feb. 23, 2001;276(8):5707-13. Epub Nov. 20, 2000.

Hasadsri et al., Functional protein delivery into neurons using polymeric nanoparticles. J Biol Chem. Mar. 13, 2009;284(11):6972-81. Epub Jan. 7, 2009.

Helene, The anti-gene strategy: control of gene expression by triplex-forming-oligonucleotides. Anticancer Drug Des. Dec. 1991;6(6):569-84.

Helene et al., Control of gene expression by triple helix-forming oligonucleotides. The antigene strategy. Ann N Y Acad Sci. Oct. 28, 1992;660:27-36.

Hockemeyer et al., Efficient targeting of expressed and silent genes in human ESCs and iPSCs using zinc-finger nucleases. Nat Biotechnol. Sep. 2009;27(9):851-7. Epub Aug. 13, 2009.

Hollenback et al., Daxx and histone deacetylase II associate with chromatin through an interaction with core histones and the chromatin-associated protein Dek. J Cell Sci. Aug. 15, 2002;115(Pt 16):3319-30.

Hopkins et al., Internalization and processing of 10yclone10ring and the 10yclone10ring receptor in human carcinoma A431 cells. J Cell Biol. Aug. 1983;97(2):508-21.

Hoshino et al., Redundant promoter elements mediate IL-3-induced expression of a novel cytokine-inducible gene, cyclon. FEBS Lett. Mar. 6, 2007;581(5):975-80. Epub Feb. 7, 2007.

Iannone et al., Multiplexed molecular interactions of nuclear receptors using fluorescent microspheres. Cytometry. Aug. 1, 2001;44(4):326-37.

Janin, Surface and inside vols. In globular proteins. Nature. Feb. 8, 1979;277(5696):491-2.

Jantsch et al., Small interfering RNA (siRNA) delivery into murine bone marrow-derived dendritic cells by electroporation. J Immunol Methods. Aug. 20, 2008;337(1):71-7. Epub Apr. 28, 2008.

Jarver et al., In vivo biodistribution and efficacy of peptide mediated delivery. Trends Pharmacol Sci. Nov. 2010;31(11):528-35. Epub Sep. 7, 2010.

Jia et al., Demonstration of two novel methods for predicting functional siRNA efficiency. BMC Bioinformatics. May 29, 2006;7:271. 10 pages.

(56) References Cited

OTHER PUBLICATIONS

Joliot et al., Antennapedia homeobox peptide regulates neural morphogenesis. Proc Natl Acad Sci U S A. Mar. 1, 1991;88(5):1864-8.
Kada et al., Rapid estimation of avidin and streptavidin by fluorescence quenching or fluorescence polarization. Biochim Biophys Acta. Mar. 14, 1999;1427(1):44-8.
Kandavelou et al., Targeted manipulation of mammalian genomes using designed zinc finger nucleases. Biochem Biophys Res Commun. Oct. 9, 2009;388(1):56-61. Epub Jul. 25, 2009.
Kaouass et al., Histonefection: Novel and potent non-viral gene delivery. J Control Release. Jul. 20, 2006;113(3):245-54. Epub Jun. 27, 2006.
Kim et al., Generation of human induced pluripotent stem cells by direct delivery of reprogramming proteins. Cell Stem Cell. Jun. 5, 2009;4(6):472-6. Epub May 28, 2009.
Kim et al., miTarget: microRNA target gene prediction using a support vector machine BMC Bioinformatics. Sep. 18, 2006;7:411. 12 pages.
Kim et al., Targeted genome editing in human cells with zinc finger nucleases constructed via modular assembly. Genome Res. Jul. 2009;19(7):1279-88. Epub May 21, 2009.
Knight et al., Global analysis of predicted proteomes: functional adaptation of physical properties. Proc Natl Acad Sci U S A. Jun. 1, 2004;101(22):8390-5. Epub May 18, 2004.
Krek et al., Combinatorial microRNA target predictions. Nat Genet. May 2005;37(5):495-500. Epub Apr. 3, 2005.
Krutzfeldt et al., Silencing of microRNAs in vivo with 'antagomirs'. Nature. Dec. 1, 2005;438(7068):685-9. Epub Oct. 30, 2005.
Kuhlman et al., Design of a novel globular protein fold with atomic-level accuracy. Science. Nov. 21, 2003;302(5649):1364-8.
Kumar et al., Transvascular delivery of small interfering RNA to the central nervous system. Nature. Jul. 5, 2007;448(7149):39-43. Epub Jun. 17, 2007.
Kunkel et al., Efficient site-directed mutagenesis using uracil-containing DNA. Methods Enzymol. 1991;204:125-39.
Kurreck, Antisense technologies. Improvement through novel chemical modifications. Eur J Biochem. Apr. 2003;270(8):1628-44.
Kyte et al., A simple method for displaying the hydropathic character of a protein. J Mol Biol. May 5, 1982;157(1):105-32.
Lai et al., Vault nanoparticles containing an adenovirus-derived membrane lytic protein facilitate toxin and gene transfer. ACS Nano. Mar. 24, 2009;3(3):691-9.
Lawrence et al., Supercharging proteins can impart unusual resilience. J Am Chem Soc. Aug. 22, 2007;129(33):10110-2. Epub Aug. 1, 2007.
Lee et al., The interpretation of protein structures: estimation of static accessibility. J Mol Biol. Feb. 14, 1971;55(3):379-400.
Lewis et al., Methotrexate-resistant variants of human dihydrofolate reductase with substitutions of leucine 22. Kinetics, crystallography, and potential as selectable markers. J Biol Chem. Mar. 10, 1995;270(10):5057-64.
Lewis et al., Prediction of mammalian microRNA targets. Cell. Dec. 26, 2003;115(7):787-98.
Li et al., Defining the optimal parameters for hairpin-based knockdown constructs. RNA. Oct. 2007;13(10):1765-74. Epub Aug. 13, 2007.
Liu et al., siRNA delivery into human T cells and primary cells with carbon-nanotube transporters. Angew Chem Int Ed Engl. 2007;46(12):2023-7.
Loeb, Chemical and Physical Behavior of Casein Solutions. J Gen Physiol. Mar. 20, 1921;3(4):547-555.
Löfgren et al., Antiprion properties of prion protein-derived cell-penetrating peptides. FASEB J. Jul. 2008;22(7):2177-84. Epub 2008 Feb. 22, 2008.
Loison et al., A ubiquitin-based assay for the cytosolic uptake of protein transduction domains. Mol Ther. Feb. 2005;11(2):205-14.
Loladze et al., Removal of surface charge-charge interactions from ubiquitin leaves the protein folded and very stable. Protein Sci. Jan. 2002;11(1):174-7.
Lombardo et al., Gene editing in human stem cells using zinc finger nucleases and integrase-defective lentiviral vector delivery. Nat Biotechnol. Nov. 2007;25(11):1298-306. Epub Oct. 28, 2007.
Lundberg et al., Delivery of short interfering RNA using endosomolytic cell-penetrating peptides. FASEB J. Sep. 2007;21(11):2664-71. Epub Apr. 26, 2007.
Ma et al., Non-classical nuclear localization signal peptides for high efficiency lipofection of primary neurons and neuronal cell lines. Neuroscience. 2002;112(1):1-5.
Magliery et al., Combinatorial approaches to protein stability and structure. Eur J Biochem. May 2004;271(9):1595-608.
Maher, DNA triple-helix formation: an approach to artificial gene repressors? Bioessays. Dec. 1992;14(12):807-15.
Mallery et al., Antibodies mediate intracellular immunity through tripartite motif-containing 21 (TRIM21). Proc Natl Acad Sci U S A. Nov. 16, 2010;107(46):19985-90. Epub Nov. 2, 2010.
Mani et al., Design, engineering, and characterization of zinc finger nucleases. Biochem Biophys Res Commun. Sep. 23, 2005;335(2):447-57.
Matsuda et al., Controlled expression of transgenes introduced by in vivo electroporation. Proc Natl Acad Sci U S A. Jan. 16, 2007;104(3):1027-32. Epub Jan. 5, 2007.
McInerney et al., Determinants of coactivator LXXLL motif specificity in nuclear receptor transcriptional activation. Genes Dev. Nov. 1, 1998;12(21):3357-68.
McManus et al., Small interfering RNA-mediated gene silencing in T lymphocytes. J Immunol. Nov. 15, 2002;169(10):5754-60.
McNaughton et al., Mammalian cell penetration, siRNA transfection, and DNA transfection by supercharged proteins. Proc Natl Acad U S A. Apr. 14, 2009;106(15):6111-6. Epub Mar. 23, 2009.
Meade et al., Enhancing the cellular uptake of siRNA duplexes following noncovalent packaging with protein transduction domain peptides. Adv Drug Deliv Rev. Mar. 1, 2008;60(4-5):530-6. Epub Oct. 22, 2007.
Meyer et al., Breathing life into polycations: functionalization with pH-responsive endosomolytic peptides and polyethylene glycol enables siRNA delivery. J Am Chem Soc. Mar. 19, 2008;130(11):3272-3. Epub Feb. 21, 2008.
Michienzi et al., Intracellular applications of ribozymes. Methods Enzymol. 2001;341:581-96.
Mitchell et al., Polyarginine enters cells more efficiently than other polycationic homopolymers. J Pept Res. Nov. 2000;56(5):318-25.
Mootz et al., Protein splicing triggered by a small molecule. J Am Chem Soc. Aug. 7, 2002;124(31):9044-5.
Mor-Vaknin et al., The DEK nuclear autoantigen is a secreted chemotactic factor. Mol Cell Biol. Dec. 2006;26(24):9484-96. Epub Oct. 9, 2006.
Morris et al., Lentiviral-mediated delivery of siRNAs for antiviral therapy. Gene Ther. Mar. 2006;13(6):553-8.
Muckerheide et al., Cationization of protein antigens. I. Alteration of immunogenic properties. J Immunol. Feb. 1, 1987;138(3):833-7.
Muckerheide et al., Cationization of protein antigens. II. Alteration of regulatory properties. J Immunol. May 1, 1987;138(9):2800-4.
Myers et al., Optimal alignments in linear space. CABIOS. 1989;4(1):11-17.
Myou et al., Blockade of focal clustering and active conformation in beta 2-integrin-mediated adhesion of eosinophils to intercellular adhesion molecule-1 caused by transduction of HIV TAT-dominant negative Ras. J Immunol. Sep. 1, 2002;169(5):2670-6.
Naito et al., siVirus: web-based antiviral siRNA design software for highly divergent viral sequences. Nucleic Acids Res. Jul. 1, 2006;34(Web Server issue):W448-50.
Nakamura et al., ALL-1 is a histone methyltransferase that assembles a supercomplex of proteins involved in transcriptional regulation. Mol Cell. Nov. 2002;10(5):1119-28.
Nakase et al., Methodological and cellular aspects that govern the internalization mechanisms of arginine-rich cell-penetrating peptides. Adv Drug Deliv Rev. Mar. 1, 2008;60(4-5):598-607. Epub Oct. 22, 2007.
Nolden et al., Stem cell engineering using transducible Cre recombinase. Methods Mol Med. 2007;140:17-32.
Novina et al., The RNAi revolution. Nature. Jul. 8, 2004;430(6996):161-4.

(56) References Cited

OTHER PUBLICATIONS

Okita et al., Generation of germline-competent induced pluripotent stem cells. Nature. Jul. 19, 2007;448(7151):313-7. Epub Jun. 6, 2007.
Pakula et al., Genetic analysis of protein stability and function. Annu Rev Genet. 1989;23:289-310.
Pan et al., Reprogramming human fibroblasts using HIV-1 TAT recombinant proteins OCT4, SOX2, KLF4 and c-MYC. Mol Biol Rep. Apr. 2010;37(4):2117-24. Epub Aug. 9, 2009.
Pardridge et al., Enhanced endocytosis and anti-human immunodeficiency virus type 1 activity of anti-rev antibodies after cationization. J Infect Dis. Jan. 1994;169(1):55-61.
Pawar et al., Prediction of "aggregation-prone" and "aggregation-susceptible" regions in proteins associated with neurodegenerative diseases. J Mol Biol. Jul. 8, 2005;350(2):379-92.
Payne et al., Internalization and trafficking of cell surface proteoglycans and proteoglycan-binding ligands. Traffic. Apr. 2007;8(4):389-401.
Pédelacq et al., Engineering and characterization of a superfolder green fluorescent protein. Nat Biotechnol. Jan. 2006;24(1):79-88. Epub Dec. 20, 2005.
Pédelacq et al., Engineering soluble proteins for structural genomics. Nat Biotechnol. Sep. 2002;20(9):927-32. Epub Aug. 19, 2002.
Pelletier et al., An in vivo library-versus-library selection of optimized protein-protein interactions. Nat Biotechnol. Jul. 1999;17(7):683-90.
Pelletier et al., Oligomerization domain-directed reassembly of active dihydrofolate reductase from rationally designed fragments. Proc Natl Acad Sci U S A. Oct. 13, 1998;95(21):12141-6.
Perez et al., Establishment of HIV-1 resistance in CD4+ T cells by genome editing using zinc-finger nucleases. Nat Biotechnol. Jul. 2008;26(7):808-16. Epub Jun. 29, 2008.
Phillips et al., Binding and stability determinants of the PPARgamma nuclear receptocoactivator interface as revealed by shotgun alanine scanning and in vivo selection. J Am Chem Soc. Aug. 30, 2006;128(34):11298-306.
Picard et al., Src-1 and TIF2 control energy balance between white and brown adipose tissues. Cell. Dec. 27, 2002;111(7):931-41.
Proft, Sortase-mediated protein ligation: an emerging biotechnology tool for protein modification and immobilization. Biotechnol Lett. Jan. 2010;32(1):1-10. Epub Sep. 1, 2009.
Rehmsmeier et al., Fast and effective prediction of microRNA/target duplexes. RNA. Oct. 2004;10(10):1507-17.
Reynolds et al., Rational siRNA design for RNA interference. Nat Biotechnol. Mar. 2004;22(3):326-30. Epub Feb. 1, 2004.
Richmond, Solvent accessible surface area and excluded volume in proteins. Analytical equations for overlapping spheres and implications for the hydrophobic effect. J Mol Biol. Sep. 5, 1984;178(1):63-89.
Rizk et al., An engineered substance P variant for receptor-mediated delivery of synthetic antibodies into tumor cells. Proc Natl Acad Sci U S A. Jul. 7, 2009;106(27):11011-5. Epub Jun. 22, 2009.
Rose et al., Hydrophobicity of amino acid residues in globular proteins. Science. Aug. 30, 1985;229(4716):834-8.
Rosenbluh et al., Translocation of histone proteins across lipid bilayers and Mycoplasma membranes. J Mol Biol. Jan. 14, 2005;345(2):387-400.
Rosi et al., Oligonucleotide-modified gold nanoparticles for intracellular gene regulation. Science. May 19, 2006;312(5776):1027-30.
Rozema et al., Dynamic PolyConjugates for targeted in vivo delivery of siRNA to hepatocytes. Proc Natl Acad Sci U S A. Aug. 7, 2007;104(32):12982-7. Epub Jul. 24, 2007.
Ruzza et al., Tat cell-penetrating peptide has the characteristics of a poly(proline) II helix in aqueous solution and in SDS micelles. J Pept Sci. Jul. 2004;10(7):423-6.
Ryu et al., Enhanced uptake of a heterologous protein with an HIV-1 TAT protein transduction domains (PTD) at both termini. Mol Cells. Dec. 31, 2003;16(3):385-91.
Sacchetti et al., Green fluorescent protein variants fold differentially in prokaryotic and eukaryotic cells. J Cell Biochem Suppl. 2001;Suppl 36:117-28.
Santoro et al., Unfolding free energy changes determined by the linear extrapolation method. 1. Unfolding of phenylmethanesulfonyl alpha-chymotrypsin using different denaturants. Biochemistry. Oct. 18, 1988;27(21):8063-8.
Sawano et al., Directed evolution of green fluorescent protein by a new versatile PCR strategy for site-directed and semi-random mutagenesis. Nucleic Acids Res. Aug. 15, 2000;28(16):E78.
Schlesinger et al., Molecular conservation of 74 amino acid sequence of ubiquitin between cattle and man. Nature. May 29, 1975;255(5507):423-4.
Schmid et al., Albumin-binding prodrugs of camptothecin and doxorubicin with an Ala-Leu-Ala-Leu-linker that are cleaved by cathepsin B: synthesis and antitumor efficacy. Bioconjug Chem. May-Jun. 2007;18(3):702-16. Epub Mar. 23, 2007.
Schwarze et al., In vivo protein transduction: delivery of a biologically active protein into the mouse. Science. Sep. 3, 1999;285(5433):1569-72.
Schueler-Furman et al., Conserved residue clustering and protein structure prediction. Proteins. Aug. 1, 2003;52(2):225-35.
Seale et al., Transcriptional control of brown fat determination by PRDM16. Cell Metab. Jul. 2007;6(1):38-54.
Segura et al., Synthesis and in vitro characterization of an ABC triblock copolymer for siRNA delivery. Bioconjug Chem. May-Jun. 2007;18(3):736-45. Epub Mar. 15, 2007.
Shaner et al., A guide to choosing fluorescent proteins. Nat Methods. Dec. 2005;2(12):905-9.
Shaner et al., Improved monomeric red, orange and yellow fluorescent proteins derived from *Discosoma* sp. red fluorescent protein. Nat Biotechnol. Dec. 2004;22(12):1567-72. Epub Nov. 21, 2004.
Shaw et al., Lysine acetylation can generate highly charged enzymes with increased resistance toward irreversible inactivation. Protein Sci. Aug. 2008;17(8):1446-55. Epub May 1, 2008.
Shinkai et al., A novel human CC chemokine, eotaxin-3, which is expressed in IL-4-stimulated vascular endothelial cells, exhibits potent activity toward eosinophils. J Immunol. Aug. 1, 1999;163(3):1602-10.
Smith et al., Coregulator function: a key to understanding tissue specificity of selective receptor modulators. Endocr Rev. Feb. 2004;25(1):45-71.
Smith et al., Minimally cationic cell-permeable miniature proteins via alpha-helical arginine display. J Am Chem Soc. Mar. 12, 2008;130(10):2948-9. Epub Feb. 14, 2008.
Sokolova et al., Inorganic nanoparticles as carriers of nucleic acids into cells. Angew Chem Int Ed Engl. 2008;47(8):1382-95.
Sonawane et al., Chloride accumulation and swelling in endosomes enhances DNA transfer by polyamine-DNA polyplexes. J Biol Chem. Nov. 7, 2003;278(45):44826-31. Epub Aug. 27, 2003.
Song et al., Antibody mediated in vivo delivery of small interfering RNAs via cell-surface receptors. Nat Biotechnol. Jun. 2005;23(6):709-17. Epub May 22, 2005.
Soutschek et al., Therapeutic silencing of an endogenous gene by systemic administration of modified siRNAs. Nature. Nov. 11, 2004;432(7014):173-8.
Stemmer et al., Single-step assembly of a gene and entire plasmid from large Numbers of oligodeoxyribonucleotides. Gene. Oct. 16, 1995;164(1):49-53.
Stewart et al., Lentivirus-delivered stable gene silencing by RNAi in primary cells. RNA. Apr. 2003;9(4):493-501.
Stradtfeld et al., Defining molecular cornerstones during fibroblast to iPS cell reprogramming in mouse. Cell Stem Cell. Mar. 6, 2008;2(3):230-40. Epub Feb. 14, 2008.
Strait et al, Calcium regulation of endothelin-1 synthesis in rat inner medullary collecting duct. Am J Physiol Renal Physiol. Aug. 2007;293(2):F601-6. Epub Jun. 6, 2007.
Strickler et al., Protein stability and surface electrostatics: a charged relationship. Biochemistry. Mar. 7, 2006;45(9):2761-6.
Sun et al., Catalytic nucleic acids: from lab to applications. Pharmacol Rev. Sep. 2000;52(3):325-47.
Tabara et al., The rde-1 gene, RNA interference, and transposon silencing in C. elegans. Cell. Oct. 15, 1999;99(2):123-32.

(56) References Cited

OTHER PUBLICATIONS

Takahashi et al., Induction of pluripotent stem cells from adult human fibroblasts by defined factors. Cell. Nov. 30, 2007;131(5):861-72.

Takahashi et al., Induction of pluripotent stem cells from fibroblast cultures. Nat Protoc. 2007;2(12):3081-9.

Takahashi et al., Induction of pluripotent stem cells from mouse embryonic and adult fibroblast cultures by defined factors. Cell. Aug. 25, 2006;126(4):663-76. Epub Aug. 10, 2006.

Takeuchi et al., Direct and rapid cytosolic delivery using cell-penetrating peptides mediated by pyrenebutyrate. ACS Chem Biol. Jun. 20, 2006;1(5):299-303.

Tang et al., Structural diversity of self-cleaving ribozymes. Proc Natl Acad Sci U S A. May 23, 2000;97(11):5784-9.

Thillet et al., Site-directed mutagenesis of mouse dihydrofolate reductase. Mutants with increased resistance to methotrexate and trimethoprim. J Biol Chem. Sep. 5, 1988;263(25):12500-8.

Thompson et al., Construction and expression of a synthetic streptavidin-encoding gene in *Escherichia coli*. Gene. Dec. 22, 1993;136(1-2):243-6.

Thorén et al., The antennapedia peptide penetratin translocates across lipid bilayers—the first direct observation. FEBS Lett. Oct. 6, 2000;482(3):265-8.

Triguero et al., Blood-brain barrier transport of cationized immunoglobulin G: enhanced delivery compared to native protein. Proc Natl Acad Sci U S A. Jun. 1989;86(12):4761-5.

Trouet et al., A covalent linkage between daunorubicin and proteins that is stable in serum and reversible by lysosomal hydrolases, as required for a lysosomotropic drug-carrier conjugate: in vitro and in vivo studies. Proc Natl Acad Sci U S A. Jan. 1982;79(2):626-9.

Urnov et al., Highly efficient endogenous human gene correction using designed zinc-finger nucleases. Nature. Jun. 2, 2005;435(7042):646-51. Epub Apr. 3, 2005.

Vajdos et al., Comprehensive functional maps of the antigen-binding site of an anti-ErbB2 antibody obtained with shotgun scanning mutagenesis. J Mol Biol. Jul. 5, 2002;320(2):415-28.

Vasey et al., Phase I clinical and pharmacokinetic study of PK1 [N-(2-hydroxypropypmethacrylamide copolymer doxorubicin]: first member of a new class of chemotherapeutic agents-drug-polymer conjugates. Cancer Research Campaign Phase I/II Committee. Clin Cancer Res. Jan. 1999;5(1):83-94.

Veldhoen et al., Cellular delivery of small interfering RNA by a non-covalently attached cell-penetrating peptide: quantitative analysis of uptake and biological effect. Nucleic Acids Res. 2006;34(22):6561-73. Epub Nov. 28, 2006.

Wadia et al., Modulation of cellular function by TAT mediated transduction of full length proteins. Curr Protein Pept Sci. Apr. 2003;4(2):97-104.

Wadia et al., Transducible TAT-HA fusogenic peptide enhances escape of TAT-fusion proteins after lipid raft macropinocytosis. Nat Med. Mar. 2004;10(3):310-5. Epub Feb. 8, 2004.

Waldo, Genetic screens and directed evolution for protein solubility. Curr Opin Chem Biol. Feb. 2003;7(1):33-8.

Waldo et al., Rapid protein-folding assay using green fluorescent protein. Nat Biotechnol. Jul. 1999;17(7):691-5.

Wang et al., Neutralizing antibodies to therapeutic enzymes: considerations for testing, prevention and treatment. Nat Biotechnol. Aug. 2008;26(8):901-8.

Wang et al., The functions of microRNAs in plants. Front Biosci. May 1, 2007;12:3975-82.

Weber et al., Structural origins of high-affinity biotin binding to streptavidin. Science. Jan. 6, 1989;243(4887):85-8.

Weiss et al., Rapid mapping of protein functional epitopes by combinatorial alanine scanning. Proc Natl Acad Sci U S A. Aug. 1, 2000;97(16):8950-4.

Wernig et al., In vitro reprogramming of fibroblasts into a pluripotent ES-cell-like state. Nature. Jul. 19, 2007;448(7151):318-24. Epub Jun. 6, 2007.

Wolfenden et al., Affinities of amino acid side chains for solvent water. Biochemistry. Feb. 17, 1981;20(4):849-55.

Wu et al., Ligand and coactivator identity determines the requirement of the charge clamp for coactivation of the peroxisome proliferator-activated receptor gamma. J Biol Chem. Mar. 7, 2003;278(10):8637-44. Epub Dec. 26, 2002.

Yang et al., Directed evolution approach to a structural genomics project: Rv2002 from Mycobacterium tuberculosis. Proc Natl Acad Sci U S A. Jan. 21, 2003;100(2):455-60. Epub Jan. 10, 2003.

Yin et al., Cell-penetrating peptide-conjugated antisense oligonucleotides restore systemic muscle and cardiac dystrophin expression and function. Hum Mol Genet. Dec. 15, 2008;17(24):3909-18. Epub Sep. 10, 2008.

Yiu et al., Filtering of ineffective siRNAs and improved siRNA design tool. Bioinformatics. Jan. 15, 2005;21(2):144-51. Epub Aug. 27, 2004.

Yu et al., Induced pluripotent stem cell lines derived from human somatic cells. Science. Dec. 21, 2007;318(5858):1917-20. Epub Nov. 20, 2007.

Yuen et al., Control of transcription factor activity and osteoblast differentiation in mammalian cells using an evolved small-molecule-dependent intein. J Am Chem Soc. Jul. 12, 2006;128(27):8939-46.

Zaccolo et al., An approach to random mutagenesis of DNA using mixtures of triphosphate derivatives of nucleoside analogues. J Mol Biol. Feb. 2, 1996;255(4):589-603.

Zamore et al., RNAi: double-stranded RNA directs the ATP-dependent cleavage of mRNA at 21 to 23 nucleotide intervals. Cell. Mar. 31, 2000;101(1):25-33.

Zelphati et al., Intracellular delivery of proteins with a new lipid-mediated delivery system. J Biol Chem. Sep. 14, 2001;276(37):35103-10. Epub Jul. 10, 2001.

Zhao et al., A developmental view of microRNA function. Trends Biochem Sci. Apr. 2007;32(4):189-97. Epub Mar. 9, 2007.

Zhou et al., Extreme makeover: converting one cell into another. Cell Stem Cell. Oct. 9, 2008;3(4):382-8.

Zhou et al., Generation of induced pluripotent stem cells using recombinant proteins. Cell Stem Cell. May 8, 2009;4(5):381-4. Epub Apr. 23, 2009.

Zhou et al., In vivo reprogramming of adult pancreatic exocrine cells to beta-cells. Nature. Oct. 2, 2008;455(7213):627-32. Epub Aug. 27, 2008.

Extended European Search Report for EP 12155208.7 mailed Jul. 30, 2012.

Extended European Search Report for EP 09739610.5 mailed Jul. 16, 2012.

Extended European Search Report for EP 10772365.2 mailed Dec. 5, 2012.

Office Communication, mailed Nov. 26, 2012, for U.S. Appl. No. 12/303,047.

Office Communication, mailed Mar. 26, 2013, for U.S. Appl. No. 12/989,829.

Boswell et al., Effects of charge on antibody tissue distribution and pharmacokinetics. Bioconjug Chem. Dec. 15, 2010;21(12):2153-63. doi: 10.1021/bc100261d. Epub Nov. 5, 2010.

Kwon et al., Antitumor effect of a transducible fusogenic peptide releasing multiple proapoptotic peptides by caspase-3. Mol Cancer Ther. Jun. 2008;7(6):1514-22. doi: 10.1158/1535-7163.MCT-07-2009.

Mae et al., Cell-penetrating peptides as vectors for peptide, protein and oligonucleotide delivery. Curr Opin Pharmacology. 2006;6(5):509-14.

Orange et al., Cell penetrating peptide inhibitors of nuclear factor-kappa B. Cell Mol Life Sci. Nov. 2008;65(22):3564-91. doi: 10.1007/s00018-008-8222-z.

Pace et al., Charge-charge interactions influence the denatured state ensemble and contribute to protein stability. Protein Sci. Jul. 2000;9(7):1395-8.

Rittner et al., New basic membrane-destabilizing peptides for plasmid-based gene delivery in vitro and in vivo. Mol Ther. Feb. 2002;5(2):104-14.

Sanchez-Ruiz et al., To charge or not to charge? Trends Biotechnol. Apr. 2001;19(4):132-5.

(56) References Cited

OTHER PUBLICATIONS

Simeonov et al., Surface supercharged human enteropeptidase light chain shows improved solubility and refolding yield. Protein Eng Des Sel. Mar. 2011;24(3):261-8. doi: 10.1093/protein/gzq104. Epub Nov. 16, 2010.

Thompson et al., Cellular uptake mechanisms and endosomal trafficking of supercharged proteins. Chem Biol. Jul. 27, 2012;19(7):831-43. doi: 10.1016/j.chembiol.2012.06.014.

Thompson et al., Engineering and identifying supercharged proteins for macromolecule delivery into mammalian cells. Methods Enzymol. 2012;503:293-319. doi: 10.1016/B978-0-12-396962-0.00012-4.

Office Communication, mailed Jul. 18, 2013, for U.S. Appl. No. 12/303,047.

Office Communication, mailed Dec. 4, 2013, for U.S. Appl. No. 12/989,829.

Office Communication, mailed Nov. 4, 2013, for U.S. Appl. No. 13/318,032.

Chica et al., Semi-rational approaches to engineering enzyme activity: combining the benefits of directed evolution and rational design. *Curr Opin Biotechnol.* Aug. 2005;16(4):378-84.

Devos et al., Practical limits of function prediction. *Proteins.* Oct. 1, 2000;41(1):98-107.

Haupt et al., Stage-specific conditional mutagenesis in mouse embryonic stem cell-derived neural cells and postmitotic neurons by direct delivery of biologically active Cre recombinase. *Stem Cells.* Jan. 2007;25(1):181-8. Epub Sep. 7, 2006.

Kueltzo et al., Conformational lability of herpesvirus protein VP22. *J Biol Chem.* Oct. 27, 2000;275(43):33213-21.

Lundberg et al., Positively charged DNA-binding proteins cause apparent cell membrane translocation. *Biochem Biophys Res Commun.* Feb. 22, 2002;291(2):367-71.

Mouzakitis et al., Characterization of VP22 in herpes simplex virus-infected cells. *J Virol.* Oct. 2005;79(19):12185-98.

Peitz et al., Enhanced purification of cell-permeant Cre and germline transmission after transduction into mouse embryonic stem cells. *Genesis.* Aug. 2007;45(8):508-17.

Seffernick et al., Melamine deaminase and atrazine chlorohydrolase: 98 percent identical but functionally different. *J Bacteriol.* Apr. 2001;183(8):2405-10.

Sen et al., Developments in directed evolution for improving enzyme functions. *Appl Biochem Biotechnol.* Dec. 2007;143(3):212-23.

Whisstock et al. Prediction of protein function from protein sequence and structure. *Q Rev Biophys.* Aug. 2003;36(3):307-40.

Witkowski et al., Conversion of a beta-ketoacyl synthase to a malonyl decarboxylase by replacement of the active-site cysteine with glutamine. *Biochemistry.* Sep. 7, 1999;38(36):11643-50.

Genbank Submission; NIH/NCBI, Accession No. M60748.1, Albig et al., Mar. 7, 1995, last accessed Sep. 3, 2014.

[No Author Listed] Innovage, Protein Calculator, Histone H1, accessed on Sep. 3, 2014.

Calloni et al., Investigating the effects of mutations on protein aggregation in the cell. J Biol Chem. Mar. 18, 2005;280(11):10607-13. Epub Dec. 16, 2004

Selzer et al., Rational design of faster associating and tighter binding protein complexes. Nat Struct Biol. Jul. 2000;7(7):537-41.

Wyman et al., Design, synthesis, and characterization of a cationic peptide that binds to nucleic acids and permeabilizes bilayers. Biochemistry. Mar. 11, 1997;36(10):3008-17.

[No Author Listed] Database UniProt, Accession: P02258, URL <http://www.uniprotorg/uniprot/P02258>, [Jul. 21, 1986 uploaded].

[No Author Listed] Database UniProt, Accession: P08814, URL <http://www.uniprot.org/uniprot/P08814>, [Jan. 11, 1988 uploaded].

U.S. Appl. No. 12/303,047, filed Mar. 9, 2010, Liu et al.
U.S. Appl. No. 12/989,829, filed Jan. 10, 2011, Liu et al.
U.S. Appl. No. 13/318,032, filed Oct. 28, 2011, Liu et al.

[No Author Listed] Database UniProt, Accession: O92915, Rabies Virus Glycoprotein, accessed on May 20, 2015.

[No Author Listed] Innovagen, Peptide Property Calculator, accessed on May 21, 2015.

Alves et al., Biophysical characterization of Gir2, a highly acidic protein of *Saccharomyces cerevisiae* with anomalous electrophoretic behavior. Biochem Biophys Res Commun Jan. 30, 2004;314(1):229-34.

Lee et al., Adenovirus core protein VII contains distinct sequences that mediate targeting to the nucleus and nucleolus, and colocalization with human chromosomes. J Gen Virol. Dec. 2003;84(Pt 12):3423-8.

Wierenga et al., Quantitative description of the relation between protein net charge and protein adsorption to air-water interfaces. J Phys Chem B. Sep. 8, 2005;109(35):16946-52.

\* cited by examiner

FIG. 1a

| | | |
|---|---|---|
| | FIG. 1a-1 | |
| | FIG. 1a-2 | |

GFP (−30)  MGHHHHHHGGASKGEELFDGVVPILVELDGDVNGHEFSVRGEGEGDATEG
GFP (−25)  MGHHHHHHGGASKGEELFTGVVPILVELDGDVNGHEFSVRGEGEGDATEG
sfGFP      MGHHHHHHGGASKGEELFTGVVPILVELDGDVNGHKFSVRGEGEGDATNG
GFP (+36)  MGHHHHHHGGASKGERLFRGKVPILVELDGDVNGHKFSVRGKGKGDATRG
GFP (+48)  MGHHHHHHGGRSKGRLFRGKVPILVKLKGDVNGHKFSVRGKGKGDATRG

GFP (−30)  ELTLKFICTTGELPVPWPTLVTTLTYGVQCFSDYPDHMDQHDFFKSAMPE
GFP (−25)  ELTLKFICTTGELPVPWPTLVTTLTYGVQCFSRYPDHMKQHDFFKSAMPE
sfGFP      KLTLKFICTTGKLPVPWPTLVTTLTYGVQCFSRYPDHMKQHDFFKSAMPE
GFP (+36)  KLTLKFICTTGKLPVPWPTLVTTLTYGVQCFSRYPKHMKRHDFFKSAMPK
GFP (+48)  KLTLKFICTTGKLPVPWPTLVTTLTYGVQCFSRYPKHMKRHDFFKSAMPK

GFP (−30)  GYVQERTISFKDDGTYKTRAEVKFEGDTLVNRIELKGIDFKEDGNILGHK
GFP (−25)  GYVQERTISFKDDGTYKTRAEVKFEGDTLVNRIELKGIDFKEDGNILGHK
sfGFP      GYVQERTISFKDDGTYKTRAEVKFEGDTLVNRIELKGIDFKEDGNILGHK
GFP (+36)  GYVQERTISFKDDGKYKTRAEVKFEGRTLVNRIKLKGRDFKEKGNILGHK
GFP (+48)  GYVQERTISFKKDGKYKTRAEVKFEGRTLVNRIKLKGRDFKEKGNILGHK

GFP (−30)  LEYNFNSHDVYITADKQENGIKAEFEIRHNVEDGSVQLADHYQQNTPIGD
GFP (−25)  LEYNFNSHDVYITADKQENGIKAEFEIRHNVEDGSVQLADHYQQNTPIGD
sfGFP      LEYNFNSHNVYITADKQKNGIKANFKIRHNVEDGSVQLADHYQQNTPIGD
GFP (+36)  LRYNFNSHKVYITADKRKNGIKAKFKIRHNVKDGSVQLADHYQQNTPIGR
GFP (+48)  LRYNFNSHKVYITADKRKNGIKAKFKIRHNVKDGSVQLAKHYQQNTPIGR

FIG. 1a-1

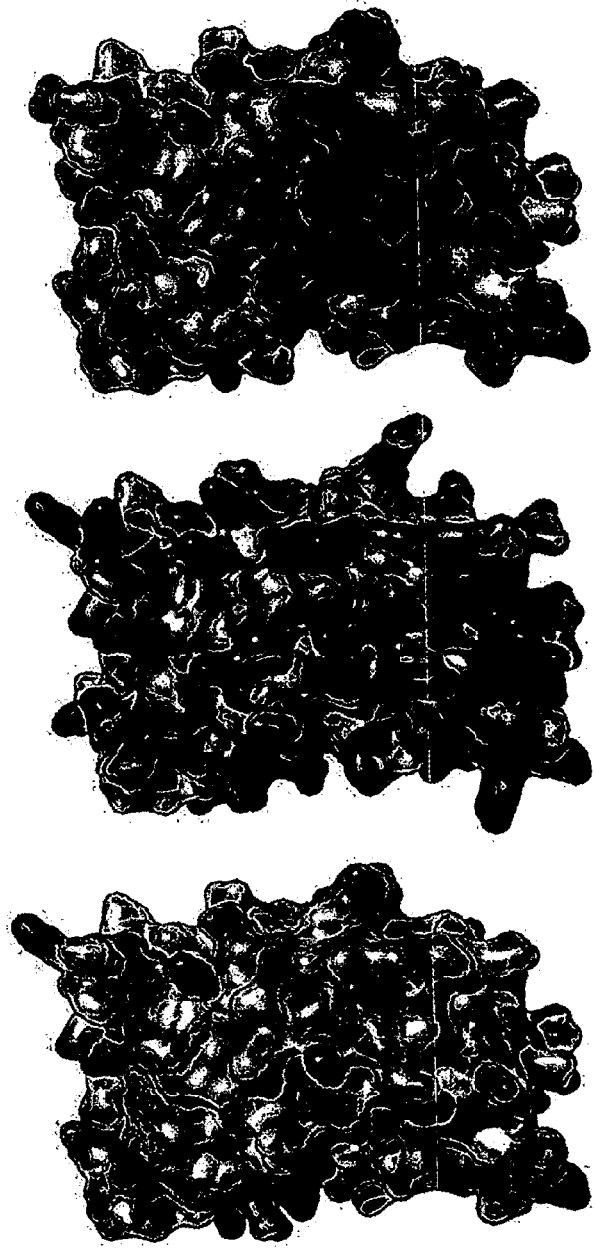

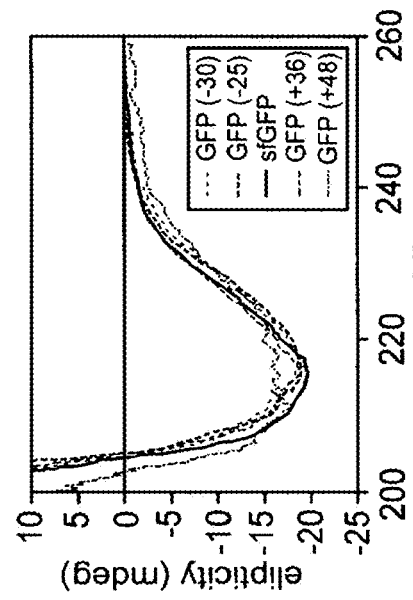
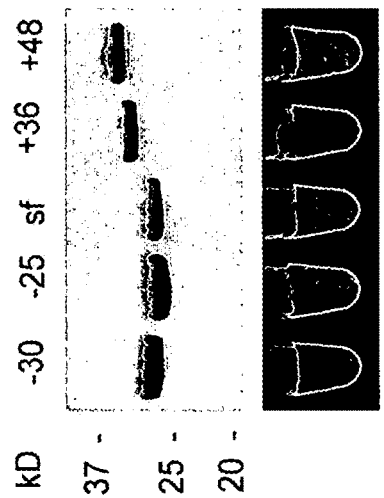
FIG. 2a
FIG. 2b
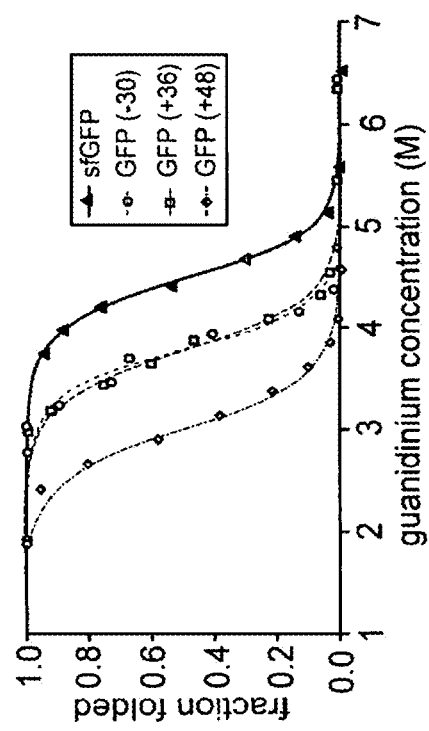
FIG. 2c

SEQUENCE LISTING

<160> NUMBER OF SEQ ID NOS: 37

<210> SEQ ID NO 1
<211> LENGTH: 238
<212> TYPE: PRT
<213> ORGANISM: Aequorea victoria

<400> SEQUENCE: 1

```
Met Ser Lys Gly Glu Glu Leu Phe Thr Gly Val Val Pro Ile Leu Val
1               5                   10                  15

Glu Leu Asp Gly Asp Val Asn Gly His Lys Phe Ser Val Ser Gly Glu
            20                  25                  30

Gly Glu Gly Asp Ala Thr Tyr Gly Lys Leu Thr Leu Lys Phe Ile Cys
        35                  40                  45

Thr Thr Gly Lys Leu Pro Val Pro Trp Pro Thr Leu Val Thr Thr Phe
    50                  55                  60

Ser Tyr Gly Val Gln Cys Phe Ser Arg Tyr Pro Asp His Met Lys Gln
65                  70                  75                  80

His Asp Phe Phe Lys Ser Ala Met Pro Glu Gly Tyr Val Gln Glu Arg
                85                  90                  95

Thr Ile Phe Phe Lys Asp Asp Gly Asn Tyr Lys Thr Arg Ala Glu Val
            100                 105                 110

Lys Phe Glu Gly Asp Thr Leu Val Asn Arg Ile Glu Leu Lys Gly Ile
        115                 120                 125

Asp Phe Lys Glu Asp Gly Asn Ile Leu Gly His Lys Leu Glu Tyr Asn
    130                 135                 140

Tyr Asn Ser His Asn Val Tyr Ile Met Ala Asp Lys Gln Lys Asn Gly
145                 150                 155                 160

Ile Lys Val Asn Phe Lys Ile Arg His Asn Ile Glu Asp Gly Ser Val
                165                 170                 175

Gln Leu Ala Asp His Tyr Gln Gln Asn Thr Pro Ile Gly Asp Gly Pro
            180                 185                 190

Val Leu Leu Pro Asp Asn His Tyr Leu Ser Thr Gln Ser Ala Leu Ser
        195                 200                 205

Lys Asp Pro Asn Glu Lys Arg Asp His Met Val Leu Leu Glu Phe Val
    210                 215                 220

Thr Ala Ala Gly Ile Thr His Gly Met Asp Glu Leu Tyr Lys
225                 230                 235
```

<210> SEQ ID NO 2
<211> LENGTH: 248
<212> TYPE: PRT
<213> ORGANISM: Artificial Sequence
<220> FEATURE:
<223> OTHER INFORMATION: Surface modified green fluorescent protein
      (GFP) from Aequorea victoria

<400> SEQUENCE: 2

```
Met Gly His His His His His His Gly Gly Ala Ser Lys Gly Glu Glu
1               5                   10                  15

Leu Phe Thr Gly Val Val Pro Ile Leu Val Glu Leu Asp Gly Asp Val
            20                  25                  30

Asn Gly His Glu Phe Ser Val Arg Gly Glu Gly Glu Gly Asp Ala Thr
        35                  40                  45

Glu Gly Glu Leu Thr Leu Lys Phe Ile Cys Thr Thr Gly Glu Leu Pro
    50                  55                  60

Val Pro Trp Pro Thr Leu Val Thr Thr Leu Thr Tyr Gly Val Gln Cys
```

```
                65                  70                  75                  80
Phe Ser Arg Tyr Pro Asp His Met Lys Gln His Asp Phe Phe Lys Ser
                    85                  90                  95
Ala Met Pro Glu Gly Tyr Val Gln Glu Arg Thr Ile Ser Phe Lys Asp
                   100                 105                 110
Asp Gly Thr Tyr Lys Thr Arg Ala Glu Val Lys Phe Glu Gly Asp Thr
                   115                 120                 125
Leu Val Asn Arg Ile Glu Leu Lys Gly Ile Asp Phe Lys Glu Asp Gly
            130                 135                 140
Asn Ile Leu Gly His Lys Leu Glu Tyr Asn Phe Asn Ser His Asp Val
145                 150                 155                 160
Tyr Ile Thr Ala Asp Lys Gln Glu Asn Gly Ile Lys Ala Glu Phe Glu
                165                 170                 175
Ile Arg His Asn Val Glu Asp Gly Ser Val Gln Leu Ala Asp His Tyr
                180                 185                 190
Gln Gln Asn Thr Pro Ile Gly Asp Gly Pro Val Leu Leu Pro Asp Asp
            195                 200                 205
His Tyr Leu Ser Thr Glu Ser Ala Leu Ser Lys Asp Pro Asn Glu Asp
        210                 215                 220
Arg Asp His Met Val Leu Leu Glu Phe Val Thr Ala Ala Gly Ile Asp
225                 230                 235                 240
His Gly Met Asp Glu Leu Tyr Lys
                245
```

<210> SEQ ID NO 3
<211> LENGTH: 248
<212> TYPE: PRT
<213> ORGANISM: Artificial Sequence
<220> FEATURE:
<223> OTHER INFORMATION: Surface modified green fluorescent protein
      (GFP) from Aequorea victoria

<400> SEQUENCE: 3

```
Met Gly His His His His His Gly Gly Ala Ser Lys Gly Glu Glu
1               5                  10                  15
Leu Phe Asp Gly Glu Val Pro Ile Leu Val Glu Leu Asp Gly Asp Val
            20                  25                  30
Asn Gly His Glu Phe Ser Val Arg Gly Glu Gly Glu Gly Asp Ala Thr
        35                  40                  45
Glu Gly Glu Leu Thr Leu Lys Phe Ile Cys Thr Thr Gly Glu Leu Pro
    50                  55                  60
Val Pro Trp Pro Thr Leu Val Thr Thr Leu Thr Tyr Gly Val Gln Cys
65                  70                  75                  80
Phe Ser Arg Tyr Pro Asp His Met Asp Gln His Asp Phe Phe Lys Ser
                    85                  90                  95
Ala Met Pro Glu Gly Tyr Val Gln Glu Arg Thr Ile Ser Phe Lys Asp
                   100                 105                 110
Asp Gly Thr Tyr Lys Thr Arg Ala Glu Val Lys Phe Glu Gly Asp Thr
                   115                 120                 125
Leu Val Asn Arg Ile Glu Leu Lys Gly Ile Asp Phe Lys Glu Asp Gly
            130                 135                 140
Asn Ile Leu Gly His Lys Leu Glu Tyr Asn Phe Asn Ser His Asp Val
145                 150                 155                 160
Tyr Ile Thr Ala Asp Lys Gln Glu Asn Gly Ile Lys Ala Glu Phe Glu
                165                 170                 175
```

```
Ile Arg His Asn Val Glu Asp Gly Ser Val Gln Leu Ala Asp His Tyr
            180                 185                 190

Gln Gln Asn Thr Pro Ile Gly Asp Gly Pro Val Leu Leu Pro Asp Asp
        195                 200                 205

His Tyr Leu Ser Thr Glu Ser Ala Leu Ser Lys Asp Pro Asn Glu Asp
        210                 215                 220

Arg Asp His Met Val Leu Leu Glu Phe Val Thr Ala Ala Gly Ile Asp
225                 230                 235                 240

His Gly Met Asp Glu Leu Tyr Lys
                245

<210> SEQ ID NO 4
<211> LENGTH: 248
<212> TYPE: PRT
<213> ORGANISM: Artificial Sequence
<220> FEATURE:
<223> OTHER INFORMATION: Surface modified green fluorescent protein
      (GFP) from Aequorea victoria

<400> SEQUENCE: 4

Met Gly His His His His His Gly Gly Ala Ser Lys Gly Glu Glu
1               5                   10                  15

Leu Phe Asp Gly Val Val Pro Ile Leu Val Glu Leu Asp Gly Asp Val
                20                  25                  30

Asn Gly His Glu Phe Ser Val Arg Gly Glu Gly Glu Gly Asp Ala Thr
            35                  40                  45

Glu Gly Glu Leu Thr Leu Lys Phe Ile Cys Thr Thr Gly Glu Leu Pro
        50                  55                  60

Val Pro Trp Pro Thr Leu Val Thr Thr Leu Thr Tyr Gly Val Gln Cys
65                  70                  75                  80

Phe Ser Asp Tyr Pro Asp His Met Asp Gln His Asp Phe Phe Lys Ser
                85                  90                  95

Ala Met Pro Glu Gly Tyr Val Gln Glu Arg Thr Ile Ser Phe Lys Asp
            100                 105                 110

Asp Gly Thr Tyr Lys Thr Arg Ala Glu Val Lys Phe Glu Gly Asp Thr
        115                 120                 125

Leu Val Asn Arg Ile Glu Leu Lys Gly Ile Asp Phe Lys Glu Asp Gly
    130                 135                 140

Asn Ile Leu Gly His Lys Leu Glu Tyr Asn Phe Asn Ser His Asp Val
145                 150                 155                 160

Tyr Ile Thr Ala Asp Lys Gln Glu Asn Gly Ile Lys Ala Glu Phe Glu
                165                 170                 175

Ile Arg His Asn Val Glu Asp Gly Ser Val Gln Leu Ala Asp His Tyr
            180                 185                 190

Gln Gln Asn Thr Pro Ile Gly Asp Gly Pro Val Leu Leu Pro Asp Asp
        195                 200                 205

His Tyr Leu Ser Thr Glu Ser Ala Leu Ser Lys Asp Pro Asn Glu Asp
        210                 215                 220

Arg Asp His Met Val Leu Leu Glu Phe Val Thr Ala Ala Gly Ile Asp
225                 230                 235                 240

His Gly Met Asp Glu Leu Tyr Lys
                245

<210> SEQ ID NO 5
<211> LENGTH: 248
<212> TYPE: PRT
<213> ORGANISM: Artificial Sequence
```

<220> FEATURE:
<223> OTHER INFORMATION: Surface modified green fluorescent protein
      (GFP) from Aequorea victoria

<400> SEQUENCE: 5

Met Gly His His His His His Gly Gly Ala Ser Lys Gly Glu Arg
1               5                   10                  15

Leu Phe Arg Gly Lys Val Pro Ile Leu Val Glu Leu Lys Gly Asp Val
                20                  25                  30

Asn Gly His Lys Phe Ser Val Arg Gly Lys Gly Lys Gly Asp Ala Thr
                35                  40                  45

Arg Gly Lys Leu Thr Leu Lys Phe Ile Cys Thr Thr Gly Lys Leu Pro
50                  55                  60

Val Pro Trp Pro Thr Leu Val Thr Thr Leu Thr Tyr Gly Val Gln Cys
65                  70                  75                  80

Phe Ser Arg Tyr Pro Lys His Met Lys Arg His Asp Phe Phe Lys Ser
                85                  90                  95

Ala Met Pro Lys Gly Tyr Val Gln Glu Arg Thr Ile Ser Phe Lys Lys
                100                 105                 110

Asp Gly Lys Tyr Lys Thr Arg Ala Glu Val Lys Phe Glu Gly Arg Thr
                115                 120                 125

Leu Val Asn Arg Ile Lys Leu Lys Gly Arg Asp Phe Lys Glu Lys Gly
                130                 135                 140

Asn Ile Leu Gly His Lys Leu Arg Tyr Asn Phe Asn Ser His Lys Val
145                 150                 155                 160

Tyr Ile Thr Ala Asp Lys Arg Lys Asn Gly Ile Lys Ala Lys Phe Lys
                165                 170                 175

Ile Arg His Asn Val Lys Asp Gly Ser Val Gln Leu Ala Asp His Tyr
                180                 185                 190

Gln Gln Asn Thr Pro Ile Gly Arg Gly Pro Val Leu Leu Pro Arg Asn
                195                 200                 205

His Tyr Leu Ser Thr Arg Ser Lys Leu Ser Lys Asp Pro Lys Glu Lys
                210                 215                 220

Arg Asp His Met Val Leu Leu Glu Phe Val Thr Ala Ala Gly Ile Lys
225                 230                 235                 240

His Gly Arg Asp Glu Arg Tyr Lys
                245

<210> SEQ ID NO 6
<211> LENGTH: 248
<212> TYPE: PRT
<213> ORGANISM: Artificial Sequence
<220> FEATURE:
<223> OTHER INFORMATION: Surface modified green fluorescent protein
      (GFP) from Aequorea victoria

<400> SEQUENCE: 6

Met Gly His His His His His Gly Gly Arg Ser Lys Gly Lys Arg
1               5                   10                  15

Leu Phe Arg Gly Lys Val Pro Ile Leu Val Glu Leu Lys Gly Asp Val
                20                  25                  30

Asn Gly His Lys Phe Ser Val Arg Gly Lys Gly Lys Gly Asp Ala Thr
                35                  40                  45

Arg Gly Lys Leu Thr Leu Lys Phe Ile Cys Thr Thr Gly Lys Leu Pro
50                  55                  60

Val Pro Trp Pro Thr Leu Val Thr Thr Leu Thr Tyr Gly Val Gln Cys
65                  70                  75                  80

```
Phe Ser Arg Tyr Pro Lys His Met Lys Arg His Asp Phe Phe Lys Ser
                85                  90                  95

Ala Met Pro Lys Gly Tyr Val Gln Glu Arg Thr Ile Ser Phe Lys Lys
            100                 105                 110

Asp Gly Lys Tyr Lys Thr Arg Ala Glu Val Lys Phe Glu Gly Arg Thr
        115                 120                 125

Leu Val Asn Arg Ile Lys Leu Lys Gly Arg Asp Phe Lys Glu Lys Gly
    130                 135                 140

Asn Ile Leu Gly His Lys Leu Arg Tyr Asn Phe Asn Ser His Lys Val
145                 150                 155                 160

Tyr Ile Thr Ala Asp Lys Arg Lys Asn Gly Ile Lys Ala Lys Phe Lys
                165                 170                 175

Ile Arg His Asn Val Lys Asp Gly Ser Val Gln Leu Ala Asp His Tyr
            180                 185                 190

Gln Gln Asn Thr Pro Ile Gly Arg Gly Pro Val Leu Leu Pro Arg Lys
        195                 200                 205

His Tyr Leu Ser Thr Arg Ser Lys Leu Ser Lys Asp Pro Lys Glu Lys
    210                 215                 220

Arg Asp His Met Val Leu Leu Glu Phe Val Thr Ala Ala Gly Ile Lys
225                 230                 235                 240

His Gly Arg Lys Glu Arg Tyr Lys
                245

<210> SEQ ID NO 7
<211> LENGTH: 248
<212> TYPE: PRT
<213> ORGANISM: Artificial Sequence
<220> FEATURE:
<223> OTHER INFORMATION: Surface modified green fluorescent protein
      (GFP) from Aequorea victoria

<400> SEQUENCE: 7

Met Gly His His His His His Gly Gly Arg Ser Lys Gly Lys Arg
1               5                   10                  15

Leu Phe Arg Gly Lys Val Pro Ile Leu Val Lys Leu Lys Gly Asp Val
            20                  25                  30

Asn Gly His Lys Phe Ser Val Arg Gly Lys Gly Lys Gly Asp Ala Thr
        35                  40                  45

Arg Gly Lys Leu Thr Leu Lys Phe Ile Cys Thr Thr Gly Lys Leu Pro
    50                  55                  60

Val Pro Trp Pro Thr Leu Val Thr Thr Leu Thr Tyr Gly Val Gln Cys
65                  70                  75                  80

Phe Ser Arg Tyr Pro Lys His Met Lys Arg His Asp Phe Phe Lys Ser
                85                  90                  95

Ala Met Pro Lys Gly Tyr Val Gln Glu Arg Thr Ile Ser Phe Lys Lys
            100                 105                 110

Asp Gly Lys Tyr Lys Thr Arg Ala Glu Val Lys Phe Glu Gly Arg Thr
        115                 120                 125

Leu Val Asn Arg Ile Lys Leu Lys Gly Arg Asp Phe Lys Glu Lys Gly
    130                 135                 140

Asn Ile Leu Gly His Lys Leu Arg Tyr Asn Phe Asn Ser His Lys Val
145                 150                 155                 160

Tyr Ile Thr Ala Asp Lys Arg Lys Asn Gly Ile Lys Ala Lys Phe Lys
                165                 170                 175

Ile Arg His Asn Val Lys Asp Gly Ser Val Gln Leu Ala Lys His Tyr
```

```
                180                 185                 190
Gln Gln Asn Thr Pro Ile Gly Arg Gly Pro Val Leu Leu Pro Arg Lys
                    195                 200                 205

His Tyr Leu Ser Thr Arg Ser Lys Leu Ser Lys Asp Pro Lys Glu Lys
        210                 215                 220

Arg Asp His Met Val Leu Lys Glu Phe Val Thr Ala Ala Gly Ile Lys
225                 230                 235                 240

His Gly Arg Lys Glu Arg Tyr Lys
                245

<210> SEQ ID NO 8
<211> LENGTH: 747
<212> TYPE: DNA
<213> ORGANISM: Artificial Sequence
<220> FEATURE:
<223> OTHER INFORMATION: Surface modified green fluorescent protein
      (GFP) from Aequorea victoria

<400> SEQUENCE: 8
atggggcatc accatcatca tcatggcggt gcgtctaagg gggaggagtt atttacgggt      60
gtggtgccga tcctggtgga gcttgatggc gatgttaacg ccatgaatt ttctgtccgc     120 ggtgaagggg agggtgatgc cacggaaggg gagctgacac ttaaatttat ttgcaccacc    180
ggtgaactcc cggtcccgtg gccgacccctg gtgaccaccc tgacctacgg cgttcaatgc   240
ttttcacgtt atccggatca catgaagcaa cacgacttct ttaaaagcgc gatgcctgaa    300
ggctatgttc aagaacgtac aattagtttt aaagatgacg gcacctacaa gacccgtgcg    360
gaagtaaaat ttgaagggga cactttagtg aaccgcatcg agctgaaagg gatcgatttt    420
aaagaagatg gaatatcct gggcacacaaa cttgaataca actttaatag tcatgacgtc     480
tatatcacgg cggacaaaca ggaaaacgga attaaggcag aatttgagat tcggcataat    540
gtcgaagatg gctcggtaca gttggctgat cactatcagc agaatacgcc gattggagat    600
ggtccggttt tattaccaga cgatcactat ctgtccaccg aatccgccct gagcaaagat    660
ccgaatgaag accgggacca tatggttctg ctggaatttg ttacggcggc tggtattgac    720
catggcatgg atgagctgta taagtag                                        747

<210> SEQ ID NO 9
<211> LENGTH: 747
<212> TYPE: DNA
<213> ORGANISM: Artificial Sequence
<220> FEATURE:
<223> OTHER INFORMATION: Surface modified green fluorescent protein
      (GFP) from Aequorea victoria

<400> SEQUENCE: 9
atggggcatc accatcatca tcatggcggt gcgtctaagg gggaggagtt atttgatggt     60
gaagtgccga tcctggtgga gcttgatggc gatgttaacg ccatgaatt ttctgtccgc    120 ggtgaagggg agggtgatgc cacggaaggg gagctgacac ttaaatttat ttgcaccacc   180
ggtgaactcc cggtcccgtg gccgacccctg gtgaccaccc tgacctacgg cgttcaatgc  240
ttttcacgtt atccggatca catggaccaa cacgacttct ttaaaagcgc gatgcctgaa   300
ggctatgttc aagaacgtac aattagtttt aaagatgacg gcacctacaa gacccgtgcg   360
gaagtaaaat ttgaagggga cactttagtg aaccgcatcg agctgaaagg gatcgatttt   420
aaagaagatg gaatatcct gggcacacaaa cttgaataca actttaatag tcatgacgtc    480
tatatcacgg cggacaaaca ggaaaacgga attaaggcag aatttgagat tcggcataat   540
```

```
gtcgaagatg gctcggtaca gttggctgat cactatcagc agaatacgcc gattggagat    600
ggtccggttt tattaccaga cgatcactat ctgtccaccg aatccgccct gagcaaagat    660
ccgaatgaag accgggacca tatggttctg ctggaatttg ttacggcggc tggtattgac    720
catggcatgg atgagctgta taagtag                                        747
```

```
<210> SEQ ID NO 10
<211> LENGTH: 747
<212> TYPE: DNA
<213> ORGANISM: Artificial Sequence
<220> FEATURE:
<223> OTHER INFORMATION: Surface modified green fluorescent protein
      (GFP) from Aequorea victoria

<400> SEQUENCE: 10
atggggcatc accatcatca tcatggcggt gcgtctaagg gggaggagtt atttgatggt     60
gtggtgccga tcctggtgga gcttgatggc gatgttaacg gccatgaatt ttctgtccgc    120
ggtgaagggg agggtgatgc cacgaagggg agctgacac ttaaatttat ttgcaccacc     180
ggtgaactcc cggtcccgtg gccgaccctg gtgaccaccc tgacctacgg cgttcaatgc    240
ttttcagatt atccggatca catggaccaa cacgacttct ttaaaagcgc gatgcctgaa    300
ggctatgttc aagaacgtac aattagtttt aaagatgacg gcacctacaa gacccgtgcg    360
gaagtaaaat ttgaagggga cactttagtg aaccgcatcg agctgaaagg gatcgatttt    420
aaagaagatg gaatatcct gggacacaaa cttgaataca actttaatag tcatgacgtc     480
tatatcacgg cggacaaaca ggaaaacgga attaaggcag aatttgagat tcggcataat    540
gtcgaagatg gctcggtaca gttggctgat cactatcagc agaatacgcc gattggagat    600
ggtccggttt tattaccaga cgatcactat ctgtccaccg aatccgccct gagcaaagat    660
ccgaatgaag accgggacca tatggttctg ctggaatttg ttacggcggc tggtattgac    720
catggcatgg atgagctgta taagtag                                        747
```

```
<210> SEQ ID NO 11
<211> LENGTH: 747
<212> TYPE: DNA
<213> ORGANISM: Artificial Sequence
<220> FEATURE:
<223> OTHER INFORMATION: Surface modified green fluorescent protein
      (GFP) from Aequorea victoria

<400> SEQUENCE: 11
atggggcatc atcatcatca ccacggcggg gcgtctaagg gagagcgctt gtttcgcggc     60
aaagtcccga ttcttgtgga gctcaaaggt gatgtaaatg gtcataaatt tagtgtgcgc    120
gggaaaggga aggagatgc tacgcggggc aagctcaccc tgaaatttat ttgcacaacc     180
ggcaaactgc cagtgccgtg gcctacatta gtcactactc tgacgtacgg tgttcagtgc    240
ttttctcgct atcccaaaca catgaaacgc atgatttct tcaagagcgc gatgccaaaa     300
ggttatgtgc aggaacgcac catcagcttt aaaaaagacg gcaaatataa acccgtgca    360 gaagttaaat tcgaaggccg caccctggtc aaccgcatta aactgaaagg tcgtgacttc    420
aaagagaaag gtaatattct tggtcacaaa ctgcgctata atttcaactc tcacaaagtt    480
tatattacgg cggataaacg taaaaacggg attaaagcga aatttaagat tcgtcataat    540
gttaaagacg gcagtgtgca gttagcggat cattatcagc agaataccc aattggtcgc    600 ggtccagtgc tgctgccgcg taaccattat ctgtcgaccc gcagcaaact cagcaaagac    660
```

```
ccgaaagaaa aacgtgacca catggtatta ctggaatttg tgaccgcagc aggcattaaa    720
catggccgcg atgaacgtta caaatag                                        747
```

<210> SEQ ID NO 12
<211> LENGTH: 747
<212> TYPE: DNA
<213> ORGANISM: Artificial Sequence
<220> FEATURE:
<223> OTHER INFORMATION: Surface modified green fluorescent protein
      (GFP) from Aequorea victoria

<400> SEQUENCE: 12

```
atgggccatc atcatcacca ccacggcggc cgctcaaaag gtaaacgctt gttccgtggt     60
aaagtaccga tcttagtgga gctcaaaggg gatgtgaatg ccataagtt ctcggttcgt    120 ggcaaaggta agggagatgc gacgcgcggc aaattaacgc tgaaattcat ttgtactaca    180
ggtaaactgc cggtgccatg gcctactctc gtcaccacgt tgacctatgg ggttcaatgc    240
ttcagccggt accctaaaca catgaagcgc acgatttct tcaaatcggc gatgccaaag    300
gggtatgtcc aggaacgcac tatcagcttc aaaaaagacg gtaagtataa aactcgtgct    360
gaagttaaat tcgaaggacg cacactggta aatcgcatta aattgaaggg gcgcgacttt    420
aaggaaaaag gtaatatctt aggtcacaaa ttgcgctaca acttcaactc tcataaagtt    480
tacattacag cagataagcg taaaaatggc atcaaagcga aattcaaaat tcgtcacaat    540
gtgaaagatg gtagcgtgca attagccgat cattaccagc agaatacgcc gatcggtcgc    600
ggcccagtac tgttgccgcg caaacattac ttatctaccc ggagtaaaact gtctaaagac    660 ccaaaagaga gcgcgacca tatggttctc ctggagtttg tcaccgccgc cggaattaaa    720
cacggccgca aagagcgcta taaatag                                        747
```

<210> SEQ ID NO 13
<211> LENGTH: 747
<212> TYPE: DNA
<213> ORGANISM: Artificial Sequence
<220> FEATURE:
<223> OTHER INFORMATION: Surface modified green fluorescent protein
      (GFP) from Aequorea victoria

<400> SEQUENCE: 13

```
atgggccacc atcatcatca ccacgggga cgctctaaag gtaaacgtct gtttcgtgga     60
aaggtgccca ttctggttaa actcaaaggt gatgtcaacg ccataagtt ttcggttcgt    120 ggcaaaggta aggtgatgc gacgcgcggg aaattaacac tgaaatttat ttgcacaacc    180
ggaaaactcc ctgtgccgtg gccgactttg gtgaccacat taacctatgg tgttcaatgc    240
ttctcacgtt atccgaagca tatgaaacgt catgattttt tcaaatcggc tatgccgaaa    300
ggttacgtcc aggagcgcac catctcattt aagaaagacg gtaagtataa acccgtgct    360 gaagtaaaat tcaaaggacg caccctggtg aatcgcatta aactgaaagg tcgtgatttc    420
aaagaaaagg gaaatatttt agggcataag ctccgttata attttaacag tcataaggtg    480
tatattaccg ctgataaacg caaaaacgga atcaaagcga atttaagat ccgtcataat    540 gtaaaagatg gctcagtcca actggcaaaa cattaccagc agaatacccc gatcggccgc    600
ggtcctgtgc ttctgccgcg taaacactac ttgtcgaccc ggtcaaaatt gagtaaagat    660
ccgaaggaaa agcgtgatca catggtcttg aaggaatttg taactgcagc aggtattaaa    720
cacgggcgca aagaacgtta caaatag                                        747
```

```
<210> SEQ ID NO 14
<211> LENGTH: 128
<212> TYPE: PRT
<213> ORGANISM: Artificial Sequence
<220> FEATURE:
<223> OTHER INFORMATION: Wild type streptavidin

<400> SEQUENCE: 14

Ala Ala Glu Ala Gly Ile Thr Gly Thr Trp Tyr Asn Gln Leu Gly Ser
1               5                   10                  15

Thr Phe Ile Val Thr Ala Gly Ala Asp Gly Ala Leu Thr Gly Thr Tyr
            20                  25                  30

Glu Ser Ala Val Gly Asn Ala Glu Ser Arg Tyr Val Leu Thr Gly Arg
        35                  40                  45

Tyr Asp Ser Ala Pro Ala Thr Asp Gly Ser Gly Thr Ala Leu Gly Trp
    50                  55                  60

Thr Val Ala Trp Lys Asn Asn Tyr Arg Asn Ala His Ser Ala Thr Thr
65                  70                  75                  80

Trp Ser Gly Gln Tyr Val Gly Gly Ala Glu Ala Arg Ile Asn Thr Gln
                85                  90                  95

Trp Leu Leu Thr Ser Gly Thr Thr Glu Ala Asn Ala Trp Lys Ser Thr
            100                 105                 110

Leu Val Gly His Asp Thr Phe Thr Lys Val Lys Pro Ser Ala Ala Ser
        115                 120                 125

<210> SEQ ID NO 15
<211> LENGTH: 137
<212> TYPE: PRT
<213> ORGANISM: Artificial Sequence
<220> FEATURE:
<223> OTHER INFORMATION: Surface modified streptavidin (SAV-NEG40)

<400> SEQUENCE: 15

Met Gly His His His His His His Gly Gly Ala Glu Ala Gly Ile Thr
1               5                   10                  15

Gly Thr Trp Tyr Asn Gln Leu Gly Ser Thr Phe Ile Val Thr Ala Gly
            20                  25                  30

Ala Asp Gly Ala Leu Thr Gly Thr Tyr Glu Ser Ala Val Gly Asp Ala
        35                  40                  45

Glu Ser Glu Tyr Val Leu Thr Gly Arg Tyr Asp Ser Ala Pro Ala Thr
    50                  55                  60

Asp Gly Ser Gly Thr Ala Leu Gly Trp Thr Val Ala Trp Lys Asn Asp
65                  70                  75                  80

Tyr Glu Asn Ala His Ser Ala Thr Thr Trp Ser Gly Gln Tyr Val Gly
                85                  90                  95

Gly Ala Glu Ala Arg Ile Asn Thr Gln Trp Leu Leu Thr Ser Gly Thr
            100                 105                 110

Thr Glu Ala Asp Ala Trp Lys Ser Thr Leu Val Gly His Asp Thr Phe
        115                 120                 125

Thr Lys Val Glu Pro Ser Ala Ala Ser
    130                 135

<210> SEQ ID NO 16
<211> LENGTH: 137
<212> TYPE: PRT
<213> ORGANISM: Artificial Sequence
<220> FEATURE:
<223> OTHER INFORMATION: Surface modifid streptavidin (SAV-POS52)

<400> SEQUENCE: 16
```

```
Met Gly His His His His His Gly Gly Ala Lys Ala Gly Ile Thr
1               5                   10                  15

Gly Thr Trp Tyr Asn Gln Leu Gly Ser Thr Phe Ile Val Thr Ala Gly
            20                  25                  30

Ala Lys Gly Ala Leu Thr Gly Thr Tyr Glu Ser Ala Val Gly Asn Ala
        35                  40                  45

Lys Ser Arg Tyr Val Leu Thr Gly Arg Tyr Asp Ser Ala Pro Ala Thr
    50                  55                  60

Lys Gly Ser Gly Thr Ala Leu Gly Trp Thr Val Ala Trp Lys Asn Lys
65                  70                  75                  80

Tyr Arg Asn Ala His Ser Ala Thr Thr Trp Ser Gly Gln Tyr Val Gly
                85                  90                  95

Gly Ala Lys Ala Arg Ile Asn Thr Gln Trp Leu Leu Thr Ser Gly Thr
            100                 105                 110

Thr Lys Ala Lys Ala Trp Lys Ser Thr Leu Val Gly His Asp Thr Phe
        115                 120                 125

Thr Lys Val Lys Pro Ser Ala Ala Ser
    130                 135
```

<210> SEQ ID NO 17
<211> LENGTH: 442
<212> TYPE: DNA
<213> ORGANISM: Artificial Sequence
<220> FEATURE:
<223> OTHER INFORMATION: Surface modified streptavidin (SAV-NEG40)

<400> SEQUENCE: 17

```
ggttcagcca tgggtcatca ccaccaccat cacggtggcg ccgaagcagg tattaccggt    60
acctggtata accagttagg ctcaacctttt attgtgaccg cggagcgga cggcgcctta   120
accggtacct acgaatcagc tgtaggtgac gcggaatcag agtacgtatt aaccggtcgt   180
tatgatagcg cgccggcgac tgacggtagc ggtactgctt taggttggac cgtagcgtgg   240
aagaatgatt atgaaaacgc acatagcgca acaacgtggt cagggcagta cgttggcgga   300
gctgaggcgc gcattaacac gcagtggtta ttaactagcg gcaccactga agctgatgcc   360
tggaagagca cgttagtggg tcatgatacc ttcactaaag tggaaccttc agctgcgtca   420
taataatgac tcgagacctg ca                                            442
```

<210> SEQ ID NO 18
<211> LENGTH: 442
<212> TYPE: DNA
<213> ORGANISM: Artificial Sequence
<220> FEATURE:
<223> OTHER INFORMATION: Surface modified streptavidin (SAV-POS52)

<400> SEQUENCE: 18

```
ggttcagcca tgggtcatca ccaccaccat cacggtggcg ccaaagcagg tattaccggt    60
acctggtata accagttagg ctcaacctttt attgtgaccg cgggagcgaa aggcgcctta   120
accggtacct acgaatcagc tgtaggaaac gcaaaatcac gctacgtatt aaccggtcgt   180
tatgatagcg cgccggcgac taaaggtagc ggtactgctt taggttggac cgtagcgtgg   240
aagaataagt atcgtaatgc gcacagtgct accacttggt cagggcagta cgtaggggga   300
gccaaagcac gtatcaacac gcagtggtta ttaacatcag gtaccaccaa agcgaaagcc   360
tggaagagca cgttagtggg tcatgatacc ttcactaaag tgaaaccttc agctgcgtca   420
taataatgac tcgagacctg ca                                            442
```

<210> SEQ ID NO 19
<211> LENGTH: 217
<212> TYPE: PRT
<213> ORGANISM: Artificial Sequence
<220> FEATURE:
<223> OTHER INFORMATION: Wild Type glutathione-S-transferase (GST)

<400> SEQUENCE: 19

```
Met Gly His His His His His Gly Gly Pro Pro Tyr Thr Ile Thr
1               5                   10                  15

Tyr Phe Pro Val Arg Gly Arg Cys Glu Ala Met Arg Met Leu Leu Ala
                20                  25                  30

Asp Gln Asp Gln Ser Trp Lys Glu Glu Val Val Thr Met Glu Thr Trp
            35                  40                  45

Pro Pro Leu Lys Pro Ser Cys Leu Phe Arg Gln Leu Pro Lys Phe Gln
        50                  55                  60

Asp Gly Asp Leu Thr Leu Tyr Gln Ser Asn Ala Ile Leu Arg His Leu
65                  70                  75                  80

Gly Arg Ser Phe Gly Leu Tyr Gly Lys Asp Gln Lys Glu Ala Ala Leu
                85                  90                  95

Val Asp Met Val Asn Asp Gly Val Glu Asp Leu Arg Cys Lys Tyr Ala
            100                 105                 110

Thr Leu Ile Tyr Thr Asn Tyr Glu Ala Gly Lys Glu Lys Tyr Val Lys
        115                 120                 125

Glu Leu Pro Glu His Leu Lys Pro Phe Glu Thr Leu Leu Ser Gln Asn
    130                 135                 140

Gln Gly Gly Gln Ala Phe Val Val Gly Ser Gln Ile Ser Phe Ala Asp
145                 150                 155                 160

Tyr Asn Leu Leu Asp Leu Leu Arg Ile His Gln Val Leu Asn Pro Ser
                165                 170                 175

Cys Leu Asp Ala Phe Pro Leu Leu Ser Ala Tyr Val Ala Arg Leu Ser
            180                 185                 190

Ala Arg Pro Lys Ile Lys Ala Phe Leu Ala Ser Pro Glu His Val Asn
        195                 200                 205

Arg Pro Ile Asn Gly Asn Gly Lys Gln
    210                 215
```

<210> SEQ ID NO 20
<211> LENGTH: 217
<212> TYPE: PRT
<213> ORGANISM: Artificial Sequence
<220> FEATURE:
<223> OTHER INFORMATION: Surface modified glutathione-S-transferase (GST-NEG40)

<400> SEQUENCE: 20

```
Met Gly His His His His His Gly Gly Pro Pro Tyr Thr Ile Thr
1               5                   10                  15

Tyr Phe Pro Val Arg Gly Arg Cys Glu Ala Met Arg Met Leu Leu Ala
                20                  25                  30

Asp Gln Asp Gln Ser Trp Glu Glu Glu Val Val Thr Met Glu Thr Trp
            35                  40                  45

Pro Pro Leu Lys Pro Ser Cys Leu Phe Arg Gln Leu Pro Lys Phe Gln
        50                  55                  60

Asp Gly Asp Leu Thr Leu Tyr Gln Ser Asn Ala Ile Leu Arg His Leu
65                  70                  75                  80
```

```
Gly Arg Ser Phe Gly Leu Tyr Gly Glu Asp Glu Glu Ala Ala Leu
                 85                  90                  95

Val Asp Met Val Asn Asp Gly Val Glu Asp Leu Arg Cys Lys Tyr Ala
            100                 105                 110

Thr Leu Ile Tyr Thr Asp Tyr Glu Ala Gly Lys Glu Glu Tyr Val Glu
            115                 120                 125

Glu Leu Pro Glu His Leu Lys Pro Phe Glu Thr Leu Leu Ser Glu Asn
130                 135                 140

Glu Gly Gly Glu Ala Phe Val Val Gly Ser Glu Ile Ser Phe Ala Asp
145                 150                 155                 160

Tyr Asn Leu Leu Asp Leu Leu Arg Ile His Gln Val Leu Asn Pro Ser
                165                 170                 175

Cys Leu Asp Ala Phe Pro Leu Leu Ser Ala Tyr Val Ala Arg Leu Ser
            180                 185                 190

Ala Arg Pro Glu Ile Glu Ala Phe Leu Ala Ser Pro Glu His Val Asp
            195                 200                 205

Arg Pro Ile Asn Gly Asn Gly Lys Gln
            210                 215

<210> SEQ ID NO 21
<211> LENGTH: 217
<212> TYPE: PRT
<213> ORGANISM: Artificial Sequence
<220> FEATURE:
<223> OTHER INFORMATION: Surface modified glutathione-S-transferase
      (GST-POS50)

<400> SEQUENCE: 21

Met Gly His His His His His His Gly Gly Pro Pro Tyr Thr Ile Thr
1               5                   10                  15

Tyr Phe Pro Val Arg Gly Arg Cys Glu Ala Met Arg Met Leu Leu Ala
                20                  25                  30

Asp Gln Lys Gln Ser Trp Lys Glu Val Val Thr Met Lys Thr Trp
        35                  40                  45

Pro Pro Leu Lys Pro Ser Cys Leu Phe Arg Gln Leu Pro Lys Phe Gln
50                  55                  60

Asp Gly Lys Leu Thr Leu Tyr Gln Ser Asn Ala Ile Leu Arg His Leu
65                  70                  75                  80

Gly Arg Ser Phe Gly Leu Tyr Gly Lys Lys Lys Glu Ala Ala Leu
                85                  90                  95

Val Asp Met Val Asn Asp Gly Val Glu Asp Leu Arg Cys Lys Tyr Ala
            100                 105                 110

Thr Leu Ile Tyr Thr Lys Tyr Lys Ala Gly Lys Lys Tyr Val Lys
            115                 120                 125

Lys Leu Pro Lys His Leu Lys Pro Phe Glu Thr Leu Leu Ser Lys Asn
130                 135                 140

Lys Gly Gly Lys Ala Phe Val Val Gly Ser Lys Ile Ser Phe Ala Asp
145                 150                 155                 160

Tyr Asn Leu Leu Asp Leu Leu Arg Ile His Gln Val Leu Asn Pro Ser
                165                 170                 175

Cys Leu Lys Ala Phe Pro Leu Leu Ser Ala Tyr Val Ala Arg Leu Ser
            180                 185                 190

Ala Arg Pro Lys Ile Lys Ala Phe Leu Ala Ser Pro Glu His Val Lys
            195                 200                 205

Arg Pro Ile Asn Gly Asn Gly Lys Gln
            210                 215
```

<210> SEQ ID NO 22
<211> LENGTH: 682
<212> TYPE: DNA
<213> ORGANISM: Artificial Sequence
<220> FEATURE:
<223> OTHER INFORMATION: Surface modified glutathione-S-transferase
      (GST-NEG40)

<400> SEQUENCE: 22

```
ggttcagcca tgggtcatca ccaccaccat cacggtggcc cgccgtacac cattacatac      60
tttccggtac gtggtcgttg tgaagcgatg cgtatgttat tagcggacca ggaccaatca     120
tgggaagaag aagtagtgac aatggaaacc tggccgccgt taaagcctag ctgtttattc     180
cgtcaattac cgaagtttca ggatggtgat ttaaccttat accagtctaa cgcgatctta     240
cgtcatttag gtcgctcatt tggtttatac ggtgaagatg aagaagaagc agccttagtg     300
gatatggtga atgatggcgt ggaagactta cgttgtaaat acgcgacgtt aatttacact     360
gattatgaag ccggtaaaga ggagtacgtg aagaattac  ctgaacacct gaagccgttt     420
gaaacattac tgagcgaaaa tgaaggaggt gaggcgttcg tagttggtag cgaaattagc     480
ttcgctgatt ataacttatt agacttatta cgcattcacc aggttttaaa tcctagctgt     540
ttagacgctt tcccgttact gagcgcatat gtagcgcgcc tgagcgcccg tccggaaatt     600
gaagctttct tagcgtcacc tgaacacgta gaccgcccga ttaacggaaa cggcaagcag     660
taataatgag gtaccacctg ca                                              682
```

<210> SEQ ID NO 23
<211> LENGTH: 682
<212> TYPE: DNA
<213> ORGANISM: Artificial Sequence
<220> FEATURE:
<223> OTHER INFORMATION: Surface modified glutathione-S-transferase
      (GST-POS50)

<400> SEQUENCE: 23

```
ggttcagcca tgggtcatca ccaccaccat cacggtggcc cgccgtacac cattacatac      60
tttccggtac gtggtcgttg tgaagcgatg cgtatgttat tagcggacca gaaacaatca     120
tggaaagaag aagtagtgac aatgaagacc tggccgccgt taaagcctag ctgtttattc     180
cgtcaattac cgaagtttca ggatggtaaa ttaaccttat accagtctaa cgcgatctta     240
cgtcatttag gtcgctcatt tggtttatac ggtaagaagc agaaagaagc agccttagtg     300
gatatggtga atgatggcgt ggaagactta cgttgtaaat acgcgacgtt aatttacact     360
aaatataaag ccggtaaaaa gaagtacgtg aaaaaattac ctaaacacct gaagccgttt     420
gaaacattac tgagcaaaaa taaggaggt aaggcgttcg tagttggtag caagattagc     480
ttcgctgatt ataacttatt agacttatta cgcattcacc aggttttaaa tcctagctgt     540
ttaaaggctt tcccgttact gagcgcatat gtagcgcgcc tgagcgcccg tccgaagatc     600
aaagctttct tagcgtcacc tgaacacgtg aagcgcccga ttaacggaaa cggcaagcag     660
taataatgag gtaccacctg ca                                              682
```

<210> SEQ ID NO 24
<211> LENGTH: 248
<212> TYPE: PRT
<213> ORGANISM: Artificial Sequence
<220> FEATURE:
<223> OTHER INFORMATION: Synthetic Polypeptide

```
<400> SEQUENCE: 24

Met Gly His His His His His Gly Gly Ala Ser Lys Gly Glu Glu
1               5                   10                  15

Leu Phe Asp Gly Val Val Pro Ile Leu Val Glu Leu Asp Gly Asp Val
            20                  25                  30

Asn Gly His Glu Phe Ser Val Arg Gly Glu Gly Glu Gly Asp Ala Thr
        35                  40                  45

Glu Gly Glu Leu Thr Leu Lys Phe Ile Cys Thr Thr Gly Glu Leu Pro
    50                  55                  60

Val Pro Trp Pro Thr Leu Val Thr Thr Leu Thr Tyr Gly Val Gln Cys
65                  70                  75                  80

Phe Ser Asp Tyr Pro Asp His Met Asp Gln His Asp Phe Phe Lys Ser
                85                  90                  95

Ala Met Pro Glu Gly Tyr Val Gln Glu Arg Thr Ile Ser Phe Lys Asp
            100                 105                 110

Asp Gly Thr Tyr Lys Thr Arg Ala Glu Val Lys Phe Glu Gly Asp Thr
        115                 120                 125

Leu Val Asn Arg Ile Glu Leu Lys Gly Ile Asp Phe Lys Glu Asp Gly
    130                 135                 140

Asn Ile Leu Gly His Lys Leu Glu Tyr Asn Phe Asn Ser His Asp Val
145                 150                 155                 160

Tyr Ile Thr Ala Asp Lys Gln Glu Asn Gly Ile Lys Ala Glu Phe Glu
                165                 170                 175

Ile Arg His Asn Val Glu Asp Gly Ser Val Gln Leu Ala Asp His Tyr
            180                 185                 190

Gln Gln Asn Thr Pro Ile Gly Asp Gly Pro Val Leu Leu Pro Asp Asp
        195                 200                 205

His Tyr Leu Ser Thr Glu Ser Ala Leu Ser Lys Asp Pro Asn Glu Asp
    210                 215                 220

Arg Asp His Met Val Leu Leu Glu Phe Val Thr Ala Ala Gly Ile Asp
225                 230                 235                 240

His Gly Met Asp Glu Leu Tyr Lys
                245

<210> SEQ ID NO 25
<211> LENGTH: 248
<212> TYPE: PRT
<213> ORGANISM: Artificial Sequence
<220> FEATURE:
<223> OTHER INFORMATION: Synthetic Polypeptide

<400> SEQUENCE: 25

Met Gly His His His His His Gly Gly Ala Ser Lys Gly Glu Glu
1               5                   10                  15

Leu Phe Thr Gly Val Val Pro Ile Leu Val Glu Leu Asp Gly Asp Val
            20                  25                  30

Asn Gly His Glu Phe Ser Val Arg Gly Glu Gly Glu Gly Asp Ala Thr
        35                  40                  45

Glu Gly Glu Leu Thr Leu Lys Phe Ile Cys Thr Thr Gly Glu Leu Pro
    50                  55                  60

Val Pro Trp Pro Thr Leu Val Thr Thr Leu Thr Tyr Gly Val Gln Cys
65                  70                  75                  80

Phe Ser Arg Tyr Pro Asp His Met Lys Gln His Asp Phe Phe Lys Ser
                85                  90                  95

Ala Met Pro Glu Gly Tyr Val Gln Glu Arg Thr Ile Ser Phe Lys Asp
```

```
                    100                 105                 110
Asp Gly Thr Tyr Lys Thr Arg Ala Glu Val Lys Phe Glu Gly Asp Thr
                115                 120                 125

Leu Val Asn Arg Ile Glu Leu Lys Gly Ile Asp Phe Lys Glu Asp Gly
            130                 135                 140

Asn Ile Leu Gly His Lys Leu Glu Tyr Asn Phe Asn Ser His Asp Val
145                 150                 155                 160

Tyr Ile Thr Ala Asp Lys Gln Glu Asn Gly Ile Lys Ala Glu Phe Glu
                165                 170                 175

Ile Arg His Asn Val Glu Asp Gly Ser Val Gln Leu Ala Asp His Tyr
            180                 185                 190

Gln Gln Asn Thr Pro Ile Gly Asp Gly Pro Val Leu Leu Pro Asp Asp
                195                 200                 205

His Tyr Leu Ser Thr Glu Ser Ala Leu Ser Lys Asp Pro Asn Glu Asp
            210                 215                 220

Arg Asp His Met Val Leu Leu Glu Phe Val Thr Ala Ala Gly Ile Asp
225                 230                 235                 240

His Gly Met Asp Glu Leu Tyr Lys
                245

<210> SEQ ID NO 26
<211> LENGTH: 248
<212> TYPE: PRT
<213> ORGANISM: Artificial Sequence
<220> FEATURE:
<223> OTHER INFORMATION: Synthetic Polypeptide

<400> SEQUENCE: 26

Met Gly His His His His His His Gly Gly Ala Ser Lys Gly Glu Glu
1               5                   10                  15

Leu Phe Thr Gly Val Val Pro Ile Leu Val Glu Leu Asp Gly Asp Val
                20                  25                  30

Asn Gly His Lys Phe Ser Val Arg Gly Glu Gly Glu Gly Asp Ala Thr
            35                  40                  45

Asn Gly Lys Leu Thr Leu Lys Phe Ile Cys Thr Thr Gly Lys Leu Pro
        50                  55                  60

Val Pro Trp Pro Thr Leu Val Thr Thr Leu Thr Tyr Gly Val Gln Cys
65                  70                  75                  80

Phe Ser Arg Tyr Pro Asp His Met Lys Gln His Asp Phe Phe Lys Ser
                85                  90                  95

Ala Met Pro Glu Gly Tyr Val Gln Glu Arg Thr Ile Ser Phe Lys Asp
                100                 105                 110

Asp Gly Thr Tyr Lys Thr Arg Ala Glu Val Lys Phe Glu Gly Asp Thr
                115                 120                 125

Leu Val Asn Arg Ile Glu Leu Lys Gly Ile Asp Phe Lys Glu Asp Gly
            130                 135                 140

Asn Ile Leu Gly His Lys Leu Glu Tyr Asn Phe Asn Ser His Asn Val
145                 150                 155                 160

Tyr Ile Thr Ala Asp Lys Gln Lys Asn Gly Ile Lys Ala Asn Phe Lys
                165                 170                 175

Ile Arg His Asn Val Glu Asp Gly Ser Val Gln Leu Ala Asp His Tyr
            180                 185                 190

Gln Gln Asn Thr Pro Ile Gly Asp Gly Pro Val Leu Leu Pro Asp Asn
                195                 200                 205

His Tyr Leu Ser Thr Gln Ser Ala Leu Ser Lys Asp Pro Asn Glu Lys
```

```
                210                 215                 220

Arg Asp His Met Val Leu Leu Glu Phe Val Thr Ala Ala Gly Ile Thr
225                 230                 235                 240

His Gly Met Asp Glu Leu Tyr Lys
                245

<210> SEQ ID NO 27
<211> LENGTH: 248
<212> TYPE: PRT
<213> ORGANISM: Artificial Sequence
<220> FEATURE:
<223> OTHER INFORMATION: Synthetic Polypeptide

<400> SEQUENCE: 27

Met Gly His His His His His His Gly Gly Arg Ser Lys Gly Lys Arg
1               5                   10                  15

Leu Phe Arg Gly Lys Val Pro Ile Leu Val Lys Leu Lys Gly Asp Val
                20                  25                  30

Asn Gly His Lys Phe Ser Val Arg Gly Lys Gly Lys Gly Asp Ala Thr
            35                  40                  45

Arg Gly Lys Leu Thr Leu Lys Phe Ile Cys Thr Thr Gly Lys Leu Pro
50                  55                  60

Val Pro Trp Pro Thr Leu Val Thr Thr Leu Thr Tyr Gly Val Gln Cys
65                  70                  75                  80

Phe Ser Arg Tyr Pro Lys His Met Lys Arg His Asp Phe Phe Lys Ser
                85                  90                  95

Ala Met Pro Lys Gly Tyr Val Gln Glu Arg Thr Ile Ser Phe Lys Lys
            100                 105                 110

Asp Gly Lys Tyr Lys Thr Arg Ala Glu Val Lys Phe Lys Gly Arg Thr
        115                 120                 125

Leu Val Asn Arg Ile Lys Leu Lys Gly Arg Asp Phe Lys Glu Lys Gly
130                 135                 140

Asn Ile Leu Gly His Lys Leu Arg Tyr Asn Phe Asn Ser His Lys Val
145                 150                 155                 160

Tyr Ile Thr Ala Asp Lys Arg Lys Asn Gly Ile Lys Ala Lys Phe Lys
                165                 170                 175

Ile Arg His Asn Val Lys Asp Gly Ser Val Gln Leu Ala Lys His Tyr
            180                 185                 190

Gln Gln Asn Thr Pro Ile Gly Arg Gly Pro Val Leu Leu Pro Arg Lys
        195                 200                 205

His Tyr Leu Ser Thr Arg Ser Lys Leu Ser Lys Asp Pro Lys Glu Lys
210                 215                 220

Arg Asp His Met Val Leu Leu Glu Phe Val Thr Ala Ala Gly Ile Lys
225                 230                 235                 240

His Gly Arg Lys Glu Arg Tyr Lys
                245

<210> SEQ ID NO 28
<211> LENGTH: 128
<212> TYPE: PRT
<213> ORGANISM: Artificial Sequence
<220> FEATURE:
<223> OTHER INFORMATION: Synthetic Polypeptide

<400> SEQUENCE: 28

Ala Ala Glu Ala Gly Ile Thr Gly Thr Trp Tyr Asn Gln Leu Gly Ser
1               5                   10                  15
```

```
Thr Phe Ile Val Thr Ala Gly Ala Asp Gly Ala Leu Thr Gly Thr Tyr
            20                  25                  30

Glu Ser Ala Val Gly Asn Ala Glu Ser Arg Tyr Val Leu Thr Gly Arg
            35                  40                  45

Tyr Asp Ser Ala Pro Ala Thr Asp Gly Ser Gly Thr Ala Leu Gly Trp
 50                  55                  60

Thr Val Ala Trp Lys Asn Asn Tyr Arg Asn Ala His Ser Ala Thr Thr
 65                  70                  75                  80

Trp Ser Gly Gln Tyr Val Gly Gly Ala Glu Ala Arg Ile Asn Thr Gln
                85                  90                  95

Trp Leu Leu Thr Ser Gly Thr Glu Ala Asn Ala Trp Lys Ser Thr
                100                 105                 110

Leu Val Gly His Asp Thr Phe Thr Lys Val Lys Pro Ser Ala Ala Ser
            115                 120                 125

<210> SEQ ID NO 29
<211> LENGTH: 137
<212> TYPE: PRT
<213> ORGANISM: Artificial Sequence
<220> FEATURE:
<223> OTHER INFORMATION: Synthetic Polypeptide

<400> SEQUENCE: 29

Met Gly His His His His His His Gly Gly Ala Glu Ala Gly Ile Thr
1               5                   10                  15

Gly Thr Trp Tyr Asn Gln Leu Gly Ser Thr Phe Ile Val Thr Ala Gly
            20                  25                  30

Ala Asp Gly Ala Leu Thr Gly Thr Tyr Glu Ser Ala Val Gly Asp Ala
            35                  40                  45

Glu Ser Glu Tyr Val Leu Thr Gly Arg Tyr Asp Ser Ala Pro Ala Thr
 50                  55                  60

Asp Gly Ser Gly Thr Ala Leu Gly Trp Thr Val Ala Trp Lys Asn Asp
 65                  70                  75                  80

Tyr Glu Asn Ala His Ser Ala Thr Thr Trp Ser Gly Gln Tyr Val Gly
                85                  90                  95

Gly Ala Glu Ala Arg Ile Asn Thr Gln Trp Leu Leu Thr Ser Gly Thr
                100                 105                 110

Thr Glu Ala Asp Ala Trp Lys Ser Thr Leu Val Gly His Asp Thr Phe
            115                 120                 125

Thr Lys Val Glu Pro Ser Ala Ala Ser
        130                 135

<210> SEQ ID NO 30
<211> LENGTH: 137
<212> TYPE: PRT
<213> ORGANISM: Artificial Sequence
<220> FEATURE:
<223> OTHER INFORMATION: Synthetic Polypeptide

<400> SEQUENCE: 30

Met Gly His His His His His His Gly Gly Ala Lys Ala Gly Ile Thr
1               5                   10                  15

Gly Thr Trp Tyr Asn Gln Leu Gly Ser Thr Phe Ile Val Thr Ala Gly
            20                  25                  30

Ala Lys Gly Ala Leu Thr Gly Thr Tyr Glu Ser Ala Val Gly Asn Ala
            35                  40                  45

Lys Ser Arg Tyr Val Leu Thr Gly Arg Tyr Asp Ser Ala Pro Ala Thr
 50                  55                  60
```

Lys Gly Ser Gly Thr Ala Leu Gly Trp Thr Val Ala Trp Lys Asn Lys
65                  70                  75                  80

Tyr Arg Asn Ala His Ser Ala Thr Thr Trp Ser Gly Gln Tyr Val Gly
                85                  90                  95

Gly Ala Lys Ala Arg Ile Asn Thr Gln Trp Leu Leu Thr Ser Gly Thr
            100                 105                 110

Thr Lys Ala Lys Ala Trp Lys Ser Thr Leu Val Gly His Asp Thr Phe
        115                 120                 125

Thr Lys Val Lys Pro Ser Ala Ala Ser
    130                 135

<210> SEQ ID NO 31
<211> LENGTH: 442
<212> TYPE: DNA
<213> ORGANISM: Artificial Sequence
<220> FEATURE:
<223> OTHER INFORMATION: Synthetic Polynucleotide

<400> SEQUENCE: 31
ggttcagcca tgggtcatca ccaccaccat cacggtggcg ccgaagcagg tattaccggt    60
acctggtata accagttagg ctcaacccttt attgtgaccg cgggagcgga cggcgcctta   120
accggtacct acgaatcagc tgtaggtgac gcggaatcag agtacgtatt aaccggtcgt   180
tatgatagcg cgccggcgac tgacggtagc ggtactgctt taggttggac cgtagcgtgg   240
aagaatgatt atgaaaacgc acatagcgca acaacgtggt cagggcagta cgttggcgga   300
gctgaggcgc gcattaacac gcagtggtta ttaactagcg gcaccactga agctgatgcc   360
tggaagagca cgttagtggg tcatgatacc ttcactaaag tggaaccttc agctgcgtca   420
taataatgac tcgagacctg ca                                            442

<210> SEQ ID NO 32
<211> LENGTH: 442
<212> TYPE: DNA
<213> ORGANISM: Artificial Sequence
<220> FEATURE:
<223> OTHER INFORMATION: Synthetic Polynucleotide

<400> SEQUENCE: 32
ggttcagcca tgggtcatca ccaccaccat cacggtggcg ccaaagcagg tattaccggt    60
acctggtata accagttagg ctcaacccttt attgtgaccg cgggagcgaa aggcgcctta   120
accggtacct acgaatcagc tgtaggaaac gcaaaatcac gctacgtatt aaccggtcgt   180
tatgatagcg cgccggcgac taaaggtagc ggtactgctt taggttggac cgtagcgtgg   240
aagaataagt atcgtaatgc gcacagtgct accacttggt cagggcagta cgtaggggga   300
gccaaagcac gtatcaacac gcagtggtta ttaacatcag gtaccaccaa agcgaaagcc   360
tggaagagca cgttagtggg tcatgatacc ttcactaaag tgaaaccttc agctgcgtca   420
taataatgac tcgagacctg ca                                            442

<210> SEQ ID NO 33
<211> LENGTH: 217
<212> TYPE: PRT
<213> ORGANISM: Artificial Sequence
<220> FEATURE:
<223> OTHER INFORMATION: Synthetic Polypeptide

<400> SEQUENCE: 33

Met Gly His His His His His His Gly Gly Pro Pro Tyr Thr Ile Thr

```
  1               5                  10                 15
Tyr Phe Pro Val Arg Gly Arg Cys Glu Ala Met Arg Met Leu Leu Ala
            20                  25                 30

Asp Gln Asp Gln Ser Trp Lys Glu Glu Val Val Thr Met Glu Thr Trp
            35                  40                 45

Pro Pro Leu Lys Pro Ser Cys Leu Phe Arg Gln Leu Pro Lys Phe Gln
 50                  55                  60

Asp Gly Asp Leu Thr Leu Tyr Gln Ser Asn Ala Ile Leu Arg His Leu
 65                  70                  75                  80

Gly Arg Ser Phe Gly Leu Tyr Gly Lys Asp Gln Lys Glu Ala Ala Leu
                85                  90                  95

Val Asp Met Val Asn Asp Gly Val Glu Asp Leu Arg Cys Lys Tyr Ala
            100                 105                110

Thr Leu Ile Tyr Thr Asn Tyr Glu Ala Gly Lys Glu Lys Tyr Val Lys
            115                 120                125

Glu Leu Pro Glu His Leu Lys Pro Phe Glu Thr Leu Leu Ser Gln Asn
130                 135                 140

Gln Gly Gly Gln Ala Phe Val Val Gly Ser Gln Ile Ser Phe Ala Asp
145                 150                 155                 160

Tyr Asn Leu Leu Asp Leu Leu Arg Ile His Gln Val Leu Asn Pro Ser
                165                 170                 175

Cys Leu Asp Ala Phe Pro Leu Leu Ser Ala Tyr Val Ala Arg Leu Ser
            180                 185                 190

Ala Arg Pro Lys Ile Lys Ala Phe Leu Ala Ser Pro Glu His Val Asn
            195                 200                 205

Arg Pro Ile Asn Gly Asn Gly Lys Gln
            210                 215
```

<210> SEQ ID NO 34
<211> LENGTH: 217
<212> TYPE: PRT
<213> ORGANISM: Artificial Sequence
<220> FEATURE:
<223> OTHER INFORMATION: Synthetic Polypeptide

<400> SEQUENCE: 34

```
Met Gly His His His His His His Gly Gly Pro Pro Tyr Thr Ile Thr
 1               5                  10                 15

Tyr Phe Pro Val Arg Gly Arg Cys Glu Ala Met Arg Met Leu Leu Ala
            20                  25                 30

Asp Gln Asp Gln Ser Trp Glu Glu Glu Val Val Thr Met Glu Thr Trp
            35                  40                 45

Pro Pro Leu Lys Pro Ser Cys Leu Phe Arg Gln Leu Pro Lys Phe Gln
 50                  55                  60

Asp Gly Asp Leu Thr Leu Tyr Gln Ser Asn Ala Ile Leu Arg His Leu
 65                  70                  75                  80

Gly Arg Ser Phe Gly Leu Tyr Gly Glu Asp Glu Glu Ala Ala Leu
                85                  90                  95

Val Asp Met Val Asn Asp Gly Val Glu Asp Leu Arg Cys Lys Tyr Ala
            100                 105                110

Thr Leu Ile Tyr Thr Asp Tyr Glu Ala Gly Lys Glu Glu Tyr Val Glu
            115                 120                125

Glu Leu Pro Glu His Leu Lys Pro Phe Glu Thr Leu Leu Ser Glu Asn
130                 135                 140

Glu Gly Gly Glu Ala Phe Val Val Gly Ser Glu Ile Ser Phe Ala Asp
```

```
                 145                 150                 155                 160
Tyr Asn Leu Leu Asp Leu Leu Arg Ile His Gln Val Leu Asn Pro Ser
                     165                 170                 175
Cys Leu Asp Ala Phe Pro Leu Leu Ser Ala Tyr Val Ala Arg Leu Ser
                 180                 185                 190
Ala Arg Pro Glu Ile Glu Ala Phe Leu Ala Ser Pro Glu His Val Asp
             195                 200                 205
Arg Pro Ile Asn Gly Asn Gly Lys Gln
         210                 215

<210> SEQ ID NO 35
<211> LENGTH: 217
<212> TYPE: PRT
<213> ORGANISM: Artificial Sequence
<220> FEATURE:
<223> OTHER INFORMATION: Synthetic Polypeptide

<400> SEQUENCE: 35

Met Gly His His His His His His Gly Gly Pro Pro Tyr Thr Ile Thr
1               5                  10                  15
Tyr Phe Pro Val Arg Gly Arg Cys Glu Ala Met Arg Met Leu Leu Ala
             20                  25                  30
Asp Gln Lys Gln Ser Trp Lys Glu Val Val Thr Met Lys Thr Trp
         35                  40                  45
Pro Pro Leu Lys Pro Ser Cys Leu Phe Arg Gln Leu Pro Lys Phe Gln
50                  55                  60
Asp Gly Lys Leu Thr Leu Tyr Gln Ser Asn Ala Ile Leu Arg His Leu
65                  70                  75                  80
Gly Arg Ser Phe Gly Leu Tyr Gly Lys Lys Gln Lys Glu Ala Ala Leu
                 85                  90                  95
Val Asp Met Val Asn Asp Gly Val Glu Asp Leu Arg Cys Lys Tyr Ala
                100                 105                 110
Thr Leu Ile Tyr Thr Lys Tyr Lys Ala Gly Lys Lys Tyr Val Lys
             115                 120                 125
Lys Leu Pro Lys His Leu Lys Pro Phe Glu Thr Leu Leu Ser Lys Asn
130                 135                 140
Lys Gly Gly Lys Ala Phe Val Val Gly Ser Lys Ile Ser Phe Ala Asp
145                 150                 155                 160
Tyr Asn Leu Leu Asp Leu Leu Arg Ile His Gln Val Leu Asn Pro Ser
                     165                 170                 175
Cys Leu Lys Ala Phe Pro Leu Leu Ser Ala Tyr Val Ala Arg Leu Ser
                 180                 185                 190
Ala Arg Pro Lys Ile Lys Ala Phe Leu Ala Ser Pro Glu His Val Lys
             195                 200                 205
Arg Pro Ile Asn Gly Asn Gly Lys Gln
         210                 215

<210> SEQ ID NO 36
<211> LENGTH: 682
<212> TYPE: DNA
<213> ORGANISM: Artificial Sequence
<220> FEATURE:
<223> OTHER INFORMATION: Synthetic Polynucleotide

<400> SEQUENCE: 36
ggttcagcca tgggtcatca ccaccaccat cacggtggcc cgccgtacac cattacatac      60
tttccggtac gtggtcgttg tgaagcgatg cgtatgttat agcggaccag gaccaatca     120
```

```
tgggaagaag aagtagtgac aatggaaacc tggccgccgt taaagcctag ctgtttattc        180
cgtcaattac cgaagtttca ggatggtgat ttaaccttat accagtctaa cgcgatctta        240
cgtcatttag gtcgctcatt tggtttatac ggtgaagatg aagaagaagc agccttagtg        300
gatatggtga atgatggcgt ggaagactta cgttgtaaat acgcgacgtt aatttacact        360
gattatgaag ccggtaaaga ggagtacgtg gaagaattac ctgaacacct gaagccgttt        420
gaaacattac tgagcgaaaa tgaaggaggt gaggcgttcg tagttggtag cgaaattagc        480
ttcgctgatt ataacttatt agacttatta cgcattcacc aggttttaaa tcctagctgt        540
ttagacgctt tcccgttact gagcgcatat gtagcgcgcc tgagcgcccg tccggaaatt        600
gaagctttct tagcgtcacc tgaacacgta gaccgcccga ttaacggaaa cggcaagcag        660
taataatgag gtaccacctg ca                                                 682

<210> SEQ ID NO 37
<211> LENGTH: 682
<212> TYPE: DNA
<213> ORGANISM: Artificial Sequence
<220> FEATURE:
<223> OTHER INFORMATION: Synthetic Polynucleotide

<400> SEQUENCE: 37
ggttcagcca tgggtcatca ccaccaccat cacggtggcc cgccgtacac cattacatac         60
tttccggtac gtggtcgttg tgaagcgatg cgtatgttat tagcggacca gaaacaatca        120 tggaagaag aagtagtgac aatgaagacc tggccgccgt taaagcctag ctgtttattc        180
cgtcaattac cgaagtttca ggatggtaaa ttaaccttat accagtctaa cgcgatctta        240
cgtcatttag gtcgctcatt tggtttatac ggtaagaagc agaaagaagc agccttagtg        300
gatatggtga atgatggcgt ggaagactta cgttgtaaat acgcgacgtt aatttacact        360
aaatataaag ccggtaaaaa gaagtacgtg aaaaaattac ctaaacacct gaagccgttt        420
gaaacattac tgagcaaaaa taaggaggt aaggcgttcg tagttggtag caagattagc         480
ttcgctgatt ataacttatt agacttatta cgcattcacc aggttttaaa tcctagctgt        540
ttaaaggctt tcccgttact gagcgcatat gtagcgcgcc tgagcgcccg tccgaagatc        600
aaagctttct tagcgtcacc tgaacacgtg aagcgcccga ttaacggaaa cggcaagcag        660
taataatgag gtaccacctg ca                                                 682
```

PROTEIN SURFACE REMODELING

RELATED APPLICATIONS

The present application claims priority under 35 U.S.C. §120 to and is a continuation of U.S. patent application, U.S. Ser. No. 12/303,047, filed Mar. 9, 2010, which is a national stage filing under 35 U.S.C. §371 of international PCT application, PCT/US2007/070254, filed Jun. 1, 2007, which claims priority under 35 U.S.C. §119(e) to U.S. provisional patent applications, U.S. Ser. No. 60/810,364, filed Jun. 2, 2006, and U.S. Ser. No. 60/836,607, filed Aug. 9, 2006; each of which is incorporated herein by reference.

GOVERNMENT SUPPORT

The work described herein was supported, in part, by grants from the National Institutes of Health (GM065400). The United States government may have certain rights in the invention.

BACKGROUND OF THE INVENTION

Proteins are the workhorses of the cell. Proteins catalyze chemical reactions, transduce signals in biological systems, provide structural elements in cells and the extracellular matrix, act as messengers, etc. One of the major causes of misbehavior of proteins is aggregation. This is not only a problem in the laboratory but also a problem in many diseases such as Alzheimer's disease. Aggregation is a particularly vexing problem when it comes to computationally designed proteins. For example, TOP7 is a computationally designed protein with a novel fold. A longer version of TOP7, TOP7 extended, is very prone to aggregation. TOP7ex is expressed predominantly as insoluble aggregates.

As more proteins are either designed or modified to be used a tools to study biological systems or as more proteins—wild type or modified—are used as therapeutic agents, there needs to be a system for routinely modifying these proteins to be more stable and/or to prevent aggregation.

SUMMARY OF THE INVENTION

The present invention provides a system for modifying proteins to make them more stable. The invention stems from the recognition that modifying the hydrophobic areas on the surface of a protein can improve the extrathermodynamic properties of the protein. The inventive system is particularly useful in improving the solubility of a protein of interest, improving the protein's resistance to aggregation, and/or improving the protein's ability to renature. All of these properties are particularly useful in protein production, protein purification, and the use of proteins as therapeutic agents and research tools.

In one aspect, the invention provides a method of altering the primary sequence of a protein in order to increase the protein's resistance to aggregation, solubility, ability to refold, and/or general stability under a wide range of conditions. The activity of the modified protein is preferably approximately or substantially the same as the protein without modification. In certain embodiments, the modified protein retains at least 50%, 75%, 90%, or 95% of the wild type protein's activity. In one embodiments, the method includes the steps of (a) identifying the surface residues of a protein of interest; (b) identifying the particular surface residues that are not highly conserved among other proteins related to the protein of interest (i.e., determining which amino acids are not essential for the activity or function of the protein); (c) determining the hydrophobicity of the identified non-conserved surface residues; and (e) replacing at least one or more of the identified hydrophobic, non-conserved residues with an amino acid that is more polar or is charged at physiological pH. Each of the above steps may be carried out using any technique, computer software, algorithm, paradigm, etc. known in the art. After the modified protein is created, it may be tested for its activity and/or the desired property being sought. In certain embodiments, the modified protein is more stable. In certain embodiments, the modified protein is less susceptible to aggregation. The inventive method typically increases the net charge (positive or negative) on the protein at physiological pH.

In another aspect, the invention provides a method of altering the primary sequence of a protein in order to increase the protein's resistance to aggregation, solubility, ability to refold, and/or general stability under a wide range of conditions by "supercharging" the protein. That is, the overall net charge on the modified protein is increased (either positive charge or negative charge) compared to the wild type protein. Preferably, the activity of the modified protein is approximately or substantially the same as the protein without modification. In certain embodiments, the method includes the steps of (a) identifying the surface residues of a protein of interest; (b) identifying the particular surface residues that are not highly conserved among other proteins related to the protein of interest (i.e., determining which amino acids are not essential for the activity or function of the protein); (c) determining the hydrophilicity of the identified non-conserved surface residues; and (e) replacing at least one or more of the identified charged or polar, solvent-exposed, non-conserved residues with a charged amino acid that is charged at physiological pH. In certain embodiments, to make a negatively charged "supercharged" protein, the residues identified for modification are mutated either to aspartate (Asp) or glutamate (Glu) residues. In certain other embodiments, to make a positively charged "supercharged" protein, the residues identified for modification are mutated either to lysine (Lys) or arginine (Arg) residues. Each of the above steps may be carried out using any technique, computer software, algorithm, paradigm, etc. known in the art. After the modified protein is created, it may be tested for its activity and/or the desired property being sought. In certain embodiments, the modified protein ("supercharged protein") is more stable. In certain embodiments, the modified protein is less susceptible to aggregation. The inventive method typically increases the net charge (positive or negative) on the protein at physiological pH.

The theoretical net charge on over 80% of the proteins catalogued in the Protein Data Bank (PDB) fall within ±10. The modified protein created by the present invention typically have a net charge less than −10 or greater than +10. In certain embodiments, the modified protein has a net charge less than −20 or greater than +20. In certain embodiments, the modified protein has a net charge less than −30 or greater than +30. In certain embodiments, the modified protein has a net charge less than −40 or greater than +40. In certain embodiments, the modified protein has a net charge less than −50 or greater than +50. The modified proteins are able to fold correctly and retain their biological activity.

Any protein may be modified using the inventive system, and protein variants created by the inventive system are considered to be part of the present invention, as well as polynucleotides or vectors encoding the variant protein and cells expressing the variant protein. The inventive system has been used to create several new variants of green fluorescent protein (GFP). These variants retain their fluorescence; however, they are more stable than current versions of GFP under a wide range of environments. The inventive GFPs are immune to aggregation even over long periods of time and in environments that induce aggregation and are capable of refolding into a fluorescent protein even after being denatured by boiling. The inventive system has also been used to create new variants of streptavidin and glutathione-S-transferase (GST). These variants retain their biological activity and remain soluble when heated. The invention also includes polynucleotide sequences encoding the inventive GFP, streptavidin, and GST protein sequences, vectors including any of these nucleotide sequences, and cells that include such a polynucleotide sequence or vector, or express the inventive variants. In certain embodiments, the invention includes bacteria or other cells that overexpress an inventive variant. The inventive variants may be used in a variety of biological assays known in the art. For example, supercharged GFPs may be used in any assay that currently uses GFP as a reporter protein.

In another aspect, the invention provides other proteins that have been modified by the inventive system. These modified proteins preferably retain a significant portion of their original activity. In certain embodiments, the modified protein retains at least 99%, 98%, 95%, or 90% of the activity of the unmodified version. The modified protein may be more soluble, resistant to aggregation, have a increased ability to refold, and/or have greater stability under a variety of conditions. The proteins modified by the inventive system include hydrophobic proteins, recombinant proteins, membrane proteins, structural proteins, enzymes, extracellular proteins, therapeutic proteins (e.g., insulin, cytokines, immunoglobulins, fragments of immunoglobulins, etc.), receptors, cell signaling proteins, cytoplasmic proteins, nuclear proteins, transcription factors, etc. In certain specific embodiments, the proteins are therapeutic proteins for use in human or veterinary medicine. In certain embodiments, the proteins are unnatural proteins, for example, computationally designed proteins. In other embodiments, the proteins are hybrid proteins, fusion proteins, altered proteins, mutated proteins, genetically engineered proteins, or any other protein that has been altered by the hands of man.

Kits are also provided for the practice of the invention. The kits may include the reagents needed to modify a protein of interest to make it more resistant to aggregation, increase its ability to renature, or increase its stability overall. Such kits may include all or some of the following: polynucleotides, computer software, nucleotides, primers, vectors, cell lines, instructions, plates, media, buffers, enzymes, Eppendorf tubes, site-directed mutagenesis kits, etc. Preferably, the kit is conveniently packaged for use in a laboratory setting. The researcher typically provides the DNA coding sequence of the protein to be modified using the inventive technique.

DEFINITIONS

"Amino acid": The term "amino acid" refers to the basic structural subunits of proteins. An alpha-amino acid consists of an amino group, a carboxyl group, a hydrogen atom, and a side chain (i.e., R group) all bonded to a central carbon atom. This central carbon atom is referred to as the alpha carbon because it is adjacent to the carboxyl group. There are twenty natural amino acids including glycine, alanine, valine, leucine, isoleucine, phenylalanine, tyrosine, trypotphan, cysteine, methionine, serine, threonine, lysine, arginine, histidine, aspartate, glutamate, asparagine, glutamate, and proline. Hydrophobic amino acids include alanine, valine, leucine, isoleucine, and phenylalanine. Aromatic amino acids includes phenylalanine, tyrosine, tryptophan, and histine. Polar amino acids include tyrosine, cysteine, serine, threonine, lysine, arginine, histidine, aspartate, glutamate, asparagine, and glutamine. Sulfur-containing amino acids include cysteine and methionine. Basic amino acids include lysine, arginine, and histidine. Acidic amino acids include aspartate and glutamate. Unnatural amino acids have also been inserted into proteins. In certain embodiments, the twenty natural amino acids are referred to when the term "amino acid" is used.

"Antibody": The term "antibody" refers to an immunoglobulin, whether natural or wholly or partially synthetically produced. All derivatives thereof which maintain specific binding ability are also included in the term. The term also covers any protein having a binding domain which is homologous or largely homologous to an immunoglobulin binding domain. These proteins may be derived from natural sources, or partly or wholly synthetically produced. An antibody may be monoclonal or polyclonal. The antibody may be a member of any immunoglobulin class, including any of the human classes: IgG, IgM, IgA, IgD, and IgE.

"Conserved": The term "conserved" refers nucleotides or amino acid residues of a polynucleotide sequence or amino acid sequence, respectively, that are those that occur unaltered in the same position of two or more related sequences being compared. Nucleotides or amino acids that are relatively conserved are those that are conserved amongst more related sequences than nucleotides or amino acids appearing elsewhere in the sequences.

"Homologous": The term "homologous", as used herein is an art-understood term that refers to nucleic acids or proteins that are highly related at the level of nucleotide or amino acid sequence. Nucleic acids or proteins that are homologous to each other are termed homologues. Homologous may refer to the degree of sequence similarity between two sequences (i.e., nucleotide sequence or amino acid). The homology percentage figures referred to herein reflect the maximal homology possible between two sequences, i.e., the percent homology when the two sequences are so aligned as to have the greatest number of matched (homologous) positions. Homology can be readily calculated by known methods such as those described in: Computational Molecular Biology, Lesk, A. M., ed., Oxford University Press, New York, 1988; Biocomputing: Informatics and Genome Projects, Smith, D. W., ed., Academic Press, New York, 1993; Sequence Analysis in Molecular Biology, von Heinje, G., Academic Press, 1987; Computer Analysis of Sequence Data, Part I, Griffin, A. M., and Griffin, H. G., eds., Humana Press, New Jersey, 1994; and Sequence Analysis Primer, Gribskov, M. and Devereux, J., eds., M Stockton Press, New York, 1991; each of which is incorporated herein by reference. Methods commonly employed to determine homology between sequences include, but are not limited to those disclosed in Carillo, H., and Lipman, D., SIAM J Applied Math., 48:1073 (1988); incorporated herein by reference. Techniques for determining homology are codified in publicly available computer programs. Exemplary computer software to determine homology between two sequences include, but are not limited to, GCG program package, Devereux, J., et al., Nucleic Acids Research, 12(1), 387 (1984)), BLASTP, BLASTN, and FASTA Atschul, S. F. et al., J Molec. Biol., 215, 403 (1990)).

The term "homologous" necessarily refers to a comparison between at least two sequences (nucleotides sequences or amino acid sequences). In accordance with the invention, two nucleotide sequences are considered to be homologous if the polypeptides they encode are at least about 50-60% identical, preferably about 70% identical, for at least one stretch of at least 20 amino acids. Preferably, homologous nucleotide sequences are also characterized by the ability to encode a stretch of at least 4-5 uniquely specified amino acids. Both the identity and the approximate spacing of these amino acids relative to one another must be considered for nucleotide sequences to be considered homologous. For nucleotide sequences less than 60 nucleotides in length, homology is determined by the ability to encode a stretch of at least 4-5 uniquely specified amino acids.

"Peptide" or "protein": According to the present invention, a "peptide" or "protein" comprises a string of at least three amino acids linked together by peptide bonds. The terms "protein" and "peptide" may be used interchangeably. Inventive peptides preferably contain only natural amino acids, although non-natural amino acids (i.e., compounds that do not occur in nature but that can be incorporated into a polypeptide chain) and/or amino acid analogs as are known in the art may alternatively be employed. Also, one or more of the amino acids in an inventive peptide may be modified, for example, by the addition of a chemical entity such as a carbohydrate group, a phosphate group, a farnesyl group, an isofarnesyl group, a fatty acid group, a linker for conjugation, functionalization, or other modification (e.g., alpha amindation), etc. In a preferred embodiment, the modifications of the peptide lead to a more stable peptide (e.g., greater half-life in vivo). These modifications may include cyclization of the peptide, the incorporation of D-amino acids, etc. None of the modifications should substantially interfere with the desired biological activity of the peptide. In certain embodiments, the modifications of the peptide lead to a more biologically active peptide.

"Polynucleotide" or "oligonucleotide": Polynucleotide or oligonucleotide refers to a polymer of nucleotides. Typically, a polynucleotide comprises at least three nucleotides. The polymer may include natural nucleosides (i.e., adenosine, thymidine, guanosine, cytidine, uridine, deoxyadenosine, deoxythymidine, deoxyguanosine, and deoxycytidine), nucleoside analogs (e.g., 2-aminoadenosine, 2-thiothymidine, inosine, pyrrolo-pyrimidine, 3-methyl adenosine, C5-propynylcytidine, C5-propynyluridine, C5-bromouridine, C5-fluorouridine, C5-iodouridine, C5-methylcytidine, 7-deazaadenosine, 7-deazaguanosine, 8-oxoadenosine, 8-oxoguanosine, O(6)-methylguanine, and 2-thiocytidine), chemically modified bases, biologically modified bases (e.g., methylated bases), intercalated bases, modified sugars (e.g., 2'-fluororibose, ribose, 2'-deoxyribose, arabinose, and hexose), and/or modified phosphate groups (e.g., phosphorothioates and 5'-N-phosphoramidite linkages).

"Small molecule": The term "small molecule," as used herein, refers to a non-peptidic, non-oligomeric organic compound either prepared in the laboratory or found in nature. Small molecules, as used herein, can refer to compounds that are "natural product-like," however, the term "small molecule" is not limited to "natural product-like" compounds. Rather, a small molecule is typically characterized in that it contains several carbon-carbon bonds, and has a molecular weight of less than 1500, although this characterization is not intended to be limiting for the purposes of the present invention. In certain other preferred embodiments, natural-product-like small molecules are utilized.

"Stable": The term "stable" as used herein to refer to a protein refers to any aspect of protein stability. The stable modified protein as compared to the original wild type protein possesses any one or more of the following characteristics: more soluble, more resistant to aggregation, more resistant to denaturation, more resistant to unfolding, more resistant to improper or undesired folding, greater ability to renature, increased thermal stability, increased stability in a variety of environments (e.g., pH, salt concentration, presence of detergents, presence of denaturing agents, etc.), and increased stability in non-aqueous environments. In certain embodiments, the stable modified protein exhibits at least two of the above characteristics. In certain embodiments, the stable modified protein exhibits at least three of the above characteristics. Such characteristics may allow the active protein to be produced at higher levels. For example, the modified protein can be overexpressed at a higher level without aggregation than the unmodified version of the protein. Such characteristics may also allow the protein to be used as a therapeutic agent or a research tool.

BRIEF DESCRIPTION OF THE DRAWING

FIG. 1. Supercharged green fluorescent proteins (GFPs). (a) Protein sequences of GFP variants, with fluorophore-forming residues highlighted green, negatively charged residues highlighted red, and positively charged residues highlighted blue. GFP-30 (SEQ ID NO: 24); GFP-25 (SEQ ID NO: 25); sfGFP (SEQ ID NO: 26); GFP+36 (SEQ ID NO: 5); GFP+48 (SEQ ID NO: 27). (b) Electrostatic surface potentials of sfGFP (left), GFP(+36) (middle), and GFP(−30) (right), colored from −25 kT/e (red) to +25 kT/e (blue).

FIG. 2. Intramolecular properties of GFP variants. (a) Staining and UV fluorescence of purified GFP variants. Each lane and tube contains 0.2 μg of protein. (b) Circular dichroism spectra of GFP variants. (c) Thermodynamic stability of GFP variants, measured by guanidinium-induced unfolding.

DETAILED DESCRIPTION OF CERTAIN PREFERRED EMBODIMENTS OF THE INVENTION

Figure 3A:
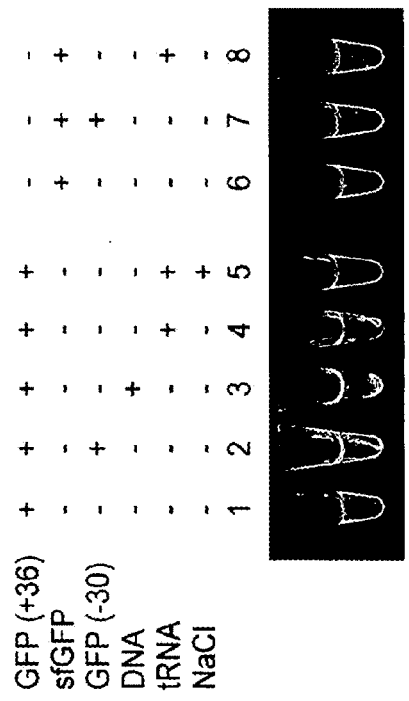
FIG. 3. Intermolecular properties of supercharged proteins. (a) UV-illuminated samples of purified GFP variants ("native"), those samples heated 1 min at 100° C. ("boiled"), and those samples subsequently cooled for 2 h at 25° C. ("cooled"). (b) Aggregation of GFP variants was induced with 40% TFE at 25° C. and monitored by right-angle light scattering. (c) Supercharged GFPs adhere reversibly to oppositely charged macromolecules. Sample 1: 6 μg of GFP(+36) in 30 μl of 25 mM Tris pH 7.0 and 100 mM NaCl. Sample 2: 6 μg of GFP(−30) added to sample 1. Sample 3: 30 μg of salmon sperm DNA added to sample 1. Sample 4: 20 μg of E. coli tRNA added to sample 1. Sample 5: Addition of NaCl to 1 M to sample 4. Samples 6-8: identical to samples 1, 2, and 4, respectively, except using sfGFP instead of GFP(+36). All samples were spun briefly in a microcentrifuge and visualized under UV light. (d) Enzymatic assays of GST variants. Reactions contained 0.5 mg/mL of GST variant, 20 mM chlorodinitrobenzene, 20 mM glutathione, and 100 mM potassium phosphate pH 6.5. Product formation was monitored at 340 nm, resulting in observed reaction rates ($k_{obs}$) of 6 $min^{-1}$ for wild-type GST, 2.2 $min^{-1}$ for GST(−40), and 0.9 $min^{-1}$ for GST(−40) after being boiled and cooled.

The invention provides a system for modifying proteins to be more stable. The system is thought to work by changing non-conserved amino acids on the surface of a protein to more polar or charged amino acid residues. The amino acids residues to be modified may be hydrophobic, hydrophilic, charged, or a combination thereof. Any protein may be modified using the inventive system to produce a more stable variant. These modifications of surface residues have been found to improve the extrathermodynamic properties of proteins. As proteins are increasingly used as therapeutic agents and as they continue to be used as research tools, a system for altering a protein to make it more stable is important and useful. Proteins modified by the inventive method typically are resistant to aggregation, have an increased ability to refold, resist improper folding, have improved solubility, and are generally more stable under a wide range of conditions including denaturing conditions such as heat or the presence of a detergent.

Any protein may be modified to create a more stable variant using the inventive system. Natural as well as unnatural proteins (e.g., engineered proteins) may be modified. Example of proteins that may be modified include receptors, membrane bound proteins, transmembrane proteins, enzymes, transcription factors, extracellular proteins, therapeutic proteins, cytokines, messenger proteins, DNA-binding proteins, RNA-binding proteins, proteins involved in signal transduction, structural proteins, cytoplasmic proteins, nuclear proteins, hydrophobic proteins, hydrophilic proteins, etc. The protein to be modified may be derived from any species of plant, animal, or microorganism. In certain embodiments, the protein is a mammalian protein. In certain embodiments, the protein is a human protein. In certain embodiments, the proteins is derived from an organism typically used in research. For example, the protein to be modified may be from a primate (e.g., ape, monkey), rodent (e.g., rabbit, hamster, gerbil), pig, dog, cat, fish (e.g., zebrafish), nematode (e.g., *C. elegans*), yeast (e.g., *Saccharomyces cervisiae*), or bacteria (e.g., *E. coli*).

The inventive system is particularly useful in modifying proteins that are susceptible to aggregation or have stability issues. The system may also be used to modify proteins that are being overexpressed. For example, therapeutic proteins that are being produced recombinantly may benefit from being modified by the inventive system. Such modified therapeutic proteins are not only easier to produce and purify but also may be more stable with respect to storage and use of the protein.

The inventive system involves identifying non-conserved surface residues of a protein of interest and replacing some of those residues with a residue that is hydrophilic, polar, or charged at physiological pH. The inventive system includes not only methods for modifying a protein but also reagents and kits that are useful in modifying a protein to make it more stable.

The surface residues of the protein to be modified are identified using any method(s) known in the art. In certain embodiments, the surface residues are identified by computer modeling of the protein. In certain embodiments, the three-dimensional structure of the protein is known and/or determined, and the surface residues are identified by visualizing the structure of the protein. In other embodiments, the surface residues are predicted using computer software. In certain particular embodiments, Average Neighbor Atoms per Sidechain Atom (AvNAPSA) is used to predict surface exposure. AvNAPSA is an automated measure of surface exposure which has been implemented as a computer program. See Appendix A. A low AvNAPSA value indicates a surface exposed residue, whereas a high value indicates a residue in the interior of the protein. In certain embodiments, the software is used to predict the secondary structure and/or tertiary structure of a protein and the surface residues are identified based on this prediction. In other embodiments, the prediction of surface residues is based on hydrophobicity and hydrophilicity of the residues and their clustering in the primary sequence of the protein. Besides in silico methods, the surface residues of the protein may also be identified using various biochemical techniques, for example, protease cleavage, surface modification, etc.

Of the surface residues, it is then determined which are conserved or important to the functioning of the protein. The identification of conserved residues can be determined using any method known in the art. In certain embodiments, the conserved residues are identified by aligning the primary sequence of the protein of interest with related proteins. These related proteins may be from the same family of proteins. For example, if the protein is an immunoglobulin, other immunoglobulin sequences may be used. The related proteins may also be the same protein from a different species. For example, the conserved residues may be identified by aligning the sequences of the same protein from different species. To give but another example, proteins of similar function or biological activity may be aligned. Preferably, 2, 3, 4, 5, 6, 7, 8, 9, or 10 different sequences are used to determine the conserved amino acids in the protein. In certain embodiments, the residue is considered conserved if over 50%, 60%, 70%, 75%, 80%, or 90% of the sequences have the same amino acid in a particular position. In other embodiments, the residue is considered conserved if over 50%, 60%, 70%, 75%, 80%, or 90% of the sequences have the same or a similar (e.g., valine, leucine, and isoleucine; glycine and alanine; glutamine and asparagine; or aspartate and glutamate) amino acid in a particular position. Many software packages are available for aligning and comparing protein sequences as described herein. As would be appreciated by one of skill in the art, either the conserved residues may be determined first or the surface residues may be determined first. The order does not matter. In certain embodiments, a computer software package may determine surface residues and conserved residues simultaneously. Important residues in the protein may also be identified by mutagenesis of the protein. For example, alanine scanning of the protein can be used to determine the important amino acid residues in the protein. In other embodiments, site-directed mutagenesis may be used.

Once non-conserved surface residues of the protein have been identified, each of the residues is identified as hydrophobic or hydrophilic. In certain embodiments, the residues is assigned a hydrophobicity score. For example, each non-conserved surface residue may be assigned an octanol/water log P value. Other hydrophobicity parameters may also be used. Such scales for amino acids have been discussed in: Janin, "Surface and Inside Volumes in Globular Proteins," *Nature* 277:491-92, 1979; Wolfenden et al., "Affinities of Amino Acid Side Chains for Solvent Water," *Biochemistry* 20:849-855, 1981; Kyte et al., "A Simple Method for Displaying the Hydropathic Character of a Protein," *J. Mol. Biol.* 157:105-132, 1982; Rose et al., "Hydrophobicity of Amino Acid Residues in Globular Proteins," *Science* 229:834-838, 1985; Cornette et al., "Hydrophobicity Scales and Computational Techniques for Detecting Amphipathic Structures in Proteins," *J. Mol. Biol.* 195:659-685, 1987; Charton and Charton, "The Structure Dependence of Amino Acid Hydrophobicity Parameters," *J. Theor. Biol.* 99:629-644, 1982; each of which is incorporated by reference. Any of these hydrophobicity parameters may be used in the inventive method to determine which non-conserved residues to modify. In certain embodiments, hydrophilic or charged residues are identified for modification.

At least one identified non-conserved or non-vital surface residue is then chosen for modification. In certain embodiments, hydrophobic residue(s) are chosen for modification. In other embodiments, hydrophilic and/or charged residue(s) are chosen for modification. In certain embodiments, more than one residue is chosen for modification. In certain embodiments, 1, 2, 3, 4, 5, 6, 7, 8, 9, or 10 of the identified residues are chosen for modification. In certain embodiments, over 10, over 15, or over 20 residues are chosen for modification. As would be appreciated by one of skill in the art, the larger the protein the more residues that will need to be modified. Also, the more hydrophobic or susceptible to aggregation or precipitation the protein is, the more residues will need to be modified. In certain embodiments, multiple variants of the protein, each with different modifications, are produced and tested to determine the best variant in terms of biological activity and stability.

In certain embodiments, the residues chosen for modification are mutated into more hydrophilic residues (including charged residues). Typically, the residues are mutated into more hydrophilic natural amino acids. In certain embodiments, the residues are mutated into amino acids that are charged at physiological pH. For example, the residue may be changed to an arginine, aspartate, glutamate, histidine, or lysine. In certain embodiments, all the residues to be modified are changed into the same different residue. For example, all the chosen residues are changed to a glutamate residue. In other embodiments, the chosen residues are changed into different residues; however, all the final residues may be either positively charged or negatively charged at physiological pH. In certain embodiments, to create a negatively charged protein, all the residues to be mutated are converted to glutamate and/or aspartate residues. In certain embodiments, to create a positively charged protein, all the residues to be mutated are converted to lysine residues. For example, all the chosen residues for modification are asparagine, glutamine, lysine, and/or arginine, and these residues are mutated into aspartate or glutamate residues. To give but another example, all the chosen residues for modification are aspartate, glutamate, asparagine, and/or glutamine, and these residues are mutated into lysine. This approach allows for modifying the net charge on the protein to the greatest extent.

In other embodiments, the protein may be modified to keep the net charge on the modified protein the same as on the unmodified protein. In still other embodiments, the protein may be modified to decrease the overall net charge on the protein while increasing the total number of charged residues on the surface. In certain embodiments, the theoretical net charge is increased by at least +1, +2, +3, +4, +5, +10, +15, +20, +25, +30, or +35. In certain embodiments, the theoretical net charge is decreased by at least −1, −2, −3, −4, −5, −10, −15, −20, −25, −30, or −35. In certain embodiments, the chosen amino acids are changed into non-ionic, polar residues (e.g., cysteine, serine, threonine, tyrosine, glutamine, asparagine).

These modification or mutations in the protein may be accomplished using any technique known in the art. Recombinant DNA techniques for introducing such changes in a protein sequence are well known in the art. In certain embodiments, the modifications are made by site-directed mutagenesis of the polynucleotide encoding the protein. Other techniques for introducing mutations are discussed in *Molecular Cloning: A Laboratory Manual,* 2nd Ed., ed. by Sambrook, Fritsch, and Maniatis (Cold Spring Harbor Laboratory Press: 1989); the treatise, *Methods in Enzymology* (Academic Press, Inc., N.Y.); Ausubel et al. *Current Protocols in Molecular Biology* (John Wiley & Sons, Inc., New York, 1999); each of which is incorporated herein by reference. The modified protein is expressed and tested. In certain embodiments, a series of variants is prepared and each variant is tested to determine its biological activity and its stability. The variant chosen for subsequent use may be the most stable one, the most active one, or the one with the greatest overall combination of activity and stability. After a first set of variants is prepared an additional set of variants may be prepared based on what is learned from the first set. The variants are typically created and overexpressed using recombinant techniques known in the art.

The inventive system has been used to created variants of GFP. These variants have been shown to be more stable and to retain their fluorescence. A GFP from *Aequorea victoria* is described in GenBank Accession Number P42212, incorporated herein by reference. The amino acid sequence of this wild type GFP is as follows:

(SEQ ID NO: 1)
MSKGEELFTGVVPILVELDGDVNGHKFSVSGEGEGDATYGKLTLKFICTT

GKLPVPWPTLVTTFSYGVQCFSRYPDHMKQHDFFKSAMPEGYVQERTIFF

KDDGNYKTRAEVKFEGDTLVNRIELKGIDFKEDGNILGHKLEYNYNSHNV

YIMADKQKNGIKVNFKIRHNIEDGSVQLADHYQQNTPIGDGPVLLPDNHY

LSTQSALSKDPNEKRDHMVLLEFVTAAGITHGMDELYK

Wild type GFP has a theoretical net charge of −7. Using the inventive system, variants with a theoretical net charge of −29, −30, −25, +36, +48, and +49 have been created. Even after heating the +36 GFP to 95° C., 100% of the variant protein is soluble and the protein retains ≥70% of its fluorescence.

The amino acid sequences of the variants of GFP that have been created include:

GFP-NEG25

(SEQ ID NO: 2)
MGHHHHHHGGASKGEELFTGVVPILVELDGDVNGHEFSVRGEGEGDATEG

ELTLKFICTTGELPVPWPTLVTTLTYGVQCFSRYPDHMKQHDFFKSAMPE

GYVQERTISFKDDGTYKTRAEVKFEGDTLVNRIELKGIDFKEDGNILGHK

LEYNFNSHDVYITADKQENGIKAEFEIRHNVEDGSVQLADHYQQNTPIGD

GPVLLPDDHYLSTESALSKDPNEDRDHMVLLEFVTAAGIDHGMDELYK

GFP-NEG29
(SEQ ID NO: 3)
MGHHHHHHGGASKGEELFDGEVPILVELDGDVNGHEFSVRGEGEGDATEG

ELTLKFICTTGELPVPWPTLVTTLTYGVQCFSRYPDHMDQHDFFKSAMPE

GYVQERTISFKDDGTYKTRAEVKFEGDTLVNRIELKGIDFKEDGNILGHK

LEYNFNSHDVYITADKQENGIKAEFEIRHNVEDGSVQLADHYQQNTPIGD

GPVLLPDDHYLSTESALSKDPNEDRDHMVLLEFVTAAGIDHGMDELYK

GFP-NEG30
(SEQ ID NO: 4)
MGHHHHHHGGASKGEELFDGVVPILVELDGDVNGHEFSVRGEGEGDATEG

ELTLKFICTTGELPVPWPTLVTTLTYGVQCFSDYPDHMDQHDFFKSAMPE

GYVQERTISFKDDGTYKTRAEVKFEGDTLVNRIELKGIDFKEDGNILGHK

LEYNFNSHDVYITADKQENGIKAEFEIRHNVEDGSVQLADHYQQNTPIGD

GPVLLPDDHYLSTESALSKDPNEDRDHMVLLEFVTAAGIDHGMDELYK

GFP-POS36)
(SEQ ID NO: 5)
MGHHHHHHGGASKGERLFRGKVPILVELKGDVNGHKFSVRGKGKGDATRG

KLTLKFICTTGKLPVPWPTLVTTLTYGVQCFSRYPKHMKRHDFFKSAMPK

GYVQERTISFKKDGKYKTRAEVKFEGRTLVNRIKLKGRDFKEKGNILGHK

LRYNFNSHKVYITADKRKNGIKAKFKIRHNVKDGSVQLADHYQQNTPIGR

GPVLLPRNHYLSTRSKLSKDPKEKRDHMVLLEFVTAAGIKHGRDERYK

GFP-POS42
(SEQ ID NO: 6)
MGHHHHHHGGRSKGKRLFRGKVPILVELKGDVNGHKFSVRGKGKGDATRG

KLTLKFICTTGKLPVPWPTLVTTLTYGVQCFSRYPKHMKRHDFFKSAMPK

GYVQERTISFKKDGKYKTRAEVKFEGRTLVNRIKLKGRDFKEKGNILGHK

LRYNFNSHKVYITADKRKNGIKAKFKIRHNVKDGSVQLADHYQQNTPIGR

GPVLLPRKHYLSTRSKLSKDPKEKRDHMVLLEFVTAAGIKHGRKERYK

GFP-POS49
(SEQ ID NO: 7)
MGHHHHHHGGRSKGKRLFRGKVPILVKLKGDVNGHKFSVRGKGKGDATRG

KLTLKFICTTGKLPVPWPTLVTTLTYGVQCFSRYPKHMKRHDFFKSAMPK

GYVQERTISFKKDGKYKTRAEVKFKGRTLVNRIKLKGRDFKEKGNILGHK

LRYNFNSHKVYITADKRKNGIKAKFKIRHNVKDGSVQLAKHYQQNTPIGR

GPVLLPRKHYLSTRSKLSKDPKEKRDHMVLKEFVTAAGIKHGRKERYK

As would be appreciated by one of skill in the art, homologous proteins are also considered to be within the scope of this invention. For example, any protein that includes a stretch of 20, 30, 40, 50, or 100 amino acids which are 60%, 70%, 80%, 90%, 95%, or 100% homologous to any of the above sequences is considered part of the invention. In addition, addition and deletion variants are also contemplated by the invention. In certain embodiments, any GFP with a mutated residue as shown in any of the above sequences is considered part of the invention. In certain embodiments, the sequence includes 2, 3, 4, 5, 6, 7, 8, 9, 10, or more mutations as shown in any of the sequences above.

Any DNA sequence that encodes the above GFP variants is also include within the scope of the invention. Exemplary DNA sequences which encode each of the variants above are as follows:

GFP-NEG25
(SEQ ID NO: 8)
ATGGGGCATCACCATCATCATCATGGCGGTGCGTCTAAGGGGGAGGAGTT

ATTTACGGGTGTGGTGCCGATCCTGGTGGAGCTTGATGGCGATGTTAACG

GCCATGAATTTTCTGTCCGCGGTGAAGGGGAGGGTGATGCCACGGAAGGG

GAGCTGACACTTAAATTTATTTGCACCACCGGTGAACTCCCGGTCCCGTG

GCCGACCCTGGTGACCACCCTGACCTACGGCGTTCAATGCTTTTCACGTT

ATCCGGATCACATGAAGCAACACGACTTCTTTAAAAGCGCGATGCCTGAA

GGCTATGTTCAAGAACGTACAATTAGTTTTAAAGATGACGGCACCTACAA

GACCCGTGCGGAAGTAAAATTTGAAGGGGACACTTTAGTGAACCGCATCG

AGCTGAAAGGGATCGATTTTAAAGAAGATGGGAATATCCTGGGACACAAA

CTTGAATACAACTTTAATAGTCATGACGTCTATATCACGGCGGACAAACA

GGAAAACGGAATTAAGGCAGAATTTGAGATTCGGCATAATGTCGAAGATG

GCTCGGTACAGTTGGCTGATCACTATCAGCAGAATACGCCGATTGGAGAT

GGTCCGGTTTTATTACCAGACGATCACTATCTGTCCACCGAATCCGCCCT

GAGCAAAGATCCGAATGAAGACCGGGACCATATGGTTCTGCTGGAATTTG

TTACGGCGGCTGGTATTGACCATGGCATGGATGAGCTGTATAAGTAG

GFP-NEG29
(SEQ ID NO: 9)
ATGGGGCATCACCATCATCATCATGGCGGTGCGTCTAAGGGGGAGGAGTT

ATTTGATGGTGAAGTGCCGATCCTGGTGGAGCTTGATGGCGATGTTAACG

GCCATGAATTTTCTGTCCGCGGTGAAGGGGAGGGTGATGCCACGGAAGGG

GAGCTGACACTTAAATTTATTTGCACCACCGGTGAACTCCCGGTCCCGTG

GCCGACCCTGGTGACCACCCTGACCTACGGCGTTCAATGCTTTTCACGTT

ATCCGGATCACATGGACCAACACGACTTCTTTAAAAGCGCGATGCCTGAA

GGCTATGTTCAAGAACGTACAATTAGTTTTAAAGATGACGGCACCTACAA

GACCCGTGCGGAAGTAAAATTTGAAGGGGACACTTTAGTGAACCGCATCG

AGCTGAAAGGGATCGATTTTAAAGAAGATGGGAATATCCTGGGACACAAA

CTTGAATACAACTTTAATAGTCATGACGTCTATATCACGGCGGACAAACA

GGAAAACGGAATTAAGGCAGAATTTGAGATTCGGCATAATGTCGAAGATG

GCTCGGTACAGTTGGCTGATCACTATCAGCAGAATACGCCGATTGGAGAT

GGTCCGGTTTTATTACCAGACGATCACTATCTGTCCACCGAATCCGCCCT

GAGCAAAGATCCGAATGAAGACCGGGACCATATGGTTCTGCTGGAATTTG

TTACGGCGGCTGGTATTGACCATGGCATGGATGAGCTGTATAAGTAG

GFP-NEG30
(SEQ ID NO: 10)
ATGGGGCATCACCATCATCATCATGGCGGTGCGTCTAAGGGGGAGGAGTT

ATTTGATGGTGTGGTGCCGATCCTGGTGGAGCTTGATGGCGATGTTAACG

GCCATGAATTTTCTGTCCGCGGTGAAGGGGAGGGTGATGCCACGGAAGGG

GAGCTGACACTTAAATTTATTTGCACCACCGGTGAACTCCCGGTCCCGTG

GCCGACCCTGGTGACCACCCTGACCTACGGCGTTCAATGCTTTTCAGATT

-continued

ATCCGGATCACATGGACCAACACGACTTCTTTAAAAGCGCGATGCCTGAA

GGCTATGTTCAAGAACGTACAATTAGTTTTAAAGATGACGGCACCTACAA

GACCCGTGCGGAAGTAAAATTTGAAGGGGACACTTTAGTGAACCGCATCG

AGCTGAAAGGGATCGATTTTAAAGAAGATGGGAATATCCTGGGACACAAA

CTTGAATACAACTTTAATAGTCATGACGTCTATATCACGGCGGACAAACA

GGAAAACGGAATTAAGGCAGAATTTGAGATTCGGCATAATGTCGAAGATG

GCTCGGTACAGTTGGCTGATCACTATCAGCAGAATACGCCGATTGGAGAT

GGTCCGGTTTTATTACCAGACGATCACTATCTGTCCACCGAATCCGCCT

GAGCAAAGATCCGAATGAAGACCGGGACCATATGGTTCTGCTGGAATTTG

TTACGGCGGCTGGTATTGACCATGGCATGGATGAGCTGTATAAGTAG

GFP-POS36

(SEQ ID NO: 11)
ATGGGGCATCATCATCATCACCACGGCGGGGCGTCTAAGGGAGAGCGCTT

GTTTCGCGGCAAAGTCCCGATTCTTGTGGAGCTCAAAGGTGATGTAAATG

GTCATAAATTTAGTGTGCGCGGGAAAGGGAAAGGAGATGCTACGCGGGGC

AAGCTCACCCTGAAATTTATTTGCACAACCGGCAAACTGCCAGTGCCGTG

GCCTACATTAGTCACTACTCTGACGTACGGTGTTCAGTGCTTTTCTCGCT

ATCCCAAACACATGAAACGCCATGATTTCTTCAAGAGCGCGATGCCAAAA

GGTTATGTGCAGGAACGCACCATCAGCTTTAAAAAAGACGGCAAATATAA

AACCCGTGCAGAAGTTAAATTCGAAGGCCGCACCCTGGTCAACCGCATTA

AACTGAAAGGTCGTGACTTCAAAGAGAAAGGTAATATTCTTGGTCACAAA

CTGCGCTATAATTTCAACTCTCACAAAGTTTATATTACGCGGATAAACG

TAAAAACGGATTAAAGCGAAATTTAAGATTCGTCATAATGTTAAAGACG

GCAGTGTGCAGTTAGCGGATCATTATCAGCAGAATACCCCAATTGGTCGC

GGTCCAGTGCTGCTGCCGCGTAACCATTATCTGTCGACCCGCAGCAAACT

CAGCAAAGACCCGAAAGAAAAACGTGACCACATGGTATTACTGGAATTTG

TGACCGCAGCAGGCATTAAACATGGCCGCGATGAACGTTACAAATAG

GFP-POS42

(SEQ ID NO: 12)
ATGGGCCATCATCATCACCACCACGGCGGCCGCTCAAAAGGTAAACGCTT

GTTCCGTGGTAAAGTACCGATCTTAGTGGAGCTCAAAGGGGATGTGAATG

GCCATAAGTTCTCGGTTCGTGGCAAAGGTAAGGGAGATGCGACGCGCGGC

AAATTAACGCTGAAATTCATTTGTACTACAGGTAAACTGCCGGTGCCATG

GCCTACTCTCGTCACCACGTTGACCTATGGGTTCAATGCTTCAGCCGGT

ACCCTAAACACATGAAGCGCCACGATTTCTTCAAATCGGCGATGCCAAAG

GGGTATGTCCAGGAACGCACTATCAGCTTCAAAAAAGACGGTAAGTATAA

AACTCGTGCTGAAGTTAAATTCGAAGGACGCACACTGGTAAATCGCATTA

AATTGAAGGGGCGCGACTTTAAGGAAAAAGGTAATATCTTAGGTCACAAA

TTGCGCTACAACTTCAACTCTCATAAAGTTTACATTACAGCAGATAAGCG

TAAAAATGGCATCAAAGCGAAATTCAAAATTCGTCACAATGTGAAAGATG

GTAGCGTGCAATTAGCCGATCATTACCAGCAGAATACGCCGATCGGTCGC

GGCCCAGTACTGTTGCCGCGCAAACATTACTTATCTACCCGGAGTAAACT

-continued

GTCTAAAGACCCAAAAGAGAAGCGCGACCATATGGTTCTCCTGGAGTTTG

TCACCGCCGCCGGAATTAAACACGGCCGCAAAGAGCGCTATAAATAG

GFP-POS49

(SEQ ID NO: 13)
ATGGGCCACCATCATCATCACCACGGGGGACGCTCTAAAGGTAAACGTCT

GTTTCGTGGAAAGGTGCCCATTCTGGTTAAACTCAAAGGTGATGTCAACG

GCCATAAGTTTTCGGTTCGTGGCAAAGGTAAAGGTGATGCGACGCGCGGG

AAATTAACACTGAAATTTATTTGCACAACCGGAAAACTCCCTGTGCCGTG

GCCGACTTTGGTGACCACATTAACCTATGGTGTTCAATGCTTCTCACGTT

ATCCGAAGCATATGAAACGTCATGATTTTTTCAAATCGGCTATGCCGAAA

GGTTACGTCCAGGAGCGCACCATCTCATTTAAGAAAGACGGTAAGTATAA

AACCCGTGCTGAAGTAAAATTCAAAGGACGCACCCTGGTGAATCGCATTA

AACTGAAAGGTCGTGATTTCAAAGAAAAGGGAAATATTTTAGGGCATAAG

CTCCGTTATAATTTTAACAGTCATAAGGTGTATATTACCGCTGATAAACG

CAAAAACGGAATCAAAGCGAAATTTAAGATCCGTCATAATGTAAAAGATG

GCTCAGTCCAACTGGCAAAACATTACCAGCAGAATACCCCGATCGGCCGC

GGTCCTGTGCTTCTGCCGCGTAAACACTACTTGTCGACCCGGTCAAAATT

GAGTAAAGATCCGAAGGAAAAGCGTGATCACATGGTCTTGAAGGAATTTG

TAACTGCAGCAGGTATTAAACACGGGCGCAAAGAACGTTACAAATAG

Polynucleotide sequence homologous to the above sequences are also within the scope of the present invention. In certain embodiments, the polynucleotide sequence include a stretch of 50, 100, or 150 nucleotides that are 60%, 70%, 80%, 90%, 95%, 98%, 99%, or 100% homologous to any one of the above sequence. The present invention also includes sequence where one or more nucleotides is inserted or deleted from one of the above sequences. Any polynucleotide sequence with a mutation as shown in any of the sequences above is considered part of the invention. In certain embodiments, the sequence includes 2, 3, 4, 5, 6, 7, 8, 9, 10, or more mutations as shown in any of the sequences above.

The present invention also provides vector (e.g., plasmids, cosmids, viruses, etc.) that comprise any of the inventive sequences herein or any other sequence (DNA or protein) modified using the inventive system. In certain embodiments, the vector includes elements such as promoter, enhancer, ribosomal binding sites, etc. sequences useful in overexpressing the inventive GFP variant in a cell. The invention also includes cells comprising the inventive sequences or vectors. In certain embodiments, the cells overexpress the variant GFP. The cells may be bacterial cells (e.g., *E. coli*), fungal cells (e.g., *P. pastoris*), yeast cells (e.g., *S. cerevisiae*), mammalian cells (e.g., CHO cells), or human cells.

The inventive system has been used to created variants of streptavidin. These variants have been shown to form soluble tetramers that bind biotin. The amino acid sequence of this wild type streptavidin is as follows:

(SEQ ID NO: 28)
AAEAGITGTWYNQLGSTFIVTAGADGALTGTYESAVGNAESRYVLTGRYD

SAPATDGSGTALGWTVAWKNNYRNAHSATTWSGQYVGGAEARINTQWLLT

SGTTEANAWKSTLVGHDTFTKVKPSAAS

Wild type streptavidin has a theoretical net charge of −4. Using the inventive system, variants with a theoretical net charge of −40 and +52 have been created. Even after heating the variants to 100° C., the proteins remained soluble.

The amino acid sequences of the variants of streptavidin that have been created include:

SAV-NEG40
(SEQ ID NO: 29)
MGHHHHHHGGAEAGITGTWYNQLGSTFIVTAGADGALTGTYESAVGDAES

EYVLTGRYDSAPATDGSGTALGWTVAWKNDYENAHSATTWSGQYVGGAEA

RINTQWLLTSGTTEADAWKSTLVGHDTFTKVEPSAAS

SAV-POS52
(SEQ ID NO: 30)
MGHHHHHHGGAKAGITGTWYNQLGSTFIVTAGAKGALTGTYESAVGNAKS

RYVLTGRYDSAPATKGSGTALGWTVAWKNKYRNAHSATTWSGQYVGGAKA

RINTQWLLTSGTTKAKAWKSTLVGHDTFTKVKPSAAS

As would be appreciated by one of skill in the art, homologous proteins are also considered to be within the scope of this invention. For example, any protein that includes a stretch of 20, 30, 40, 50, or 100 amino acids which are 60%, 70%, 80%, 90%, 95%, or 100% homologous to any of the above sequences is considered part of the invention. In addition, addition and deletion variants are also contemplated by the invention. In certain embodiments, any streptavidin with a mutated residue as shown in any of the above sequences is considered part of the invention. In certain embodiments, the sequence includes 2, 3, 4, 5, 6, 7, 8, 9, 10, or more mutations as shown in any of the sequences above.

Any DNA sequence that encodes the above streptavidin variants is also included within the scope of the invention. Exemplary DNA sequences which encode each of the variants above are as follows:

SAV-NEG40
(SEQ ID NO: 31)
GGTTCAGCCATGGGTCATCACCACCACCATCACGGTGGCGCCGAAGCAGG

TATTACCGGTACCTGGTATAACCAGTTAGGCTCAACCTTTATTGTGACCG

CGGGAGCGGACGGCGCCTTAACCGGTACCTACGAATCAGCTGTAGGTGAC

GCGGAATCAGAGTACGTATTAACCGGTCGTTATGATAGCGCGCCGGCGAC

TGACGGTAGCGGTACTGCTTTAGGTTGGACCGTAGCGTGGAAGAATGATT

ATGAAAACGCACATAGCGCAACAACGTGGTCAGGGCAGTACGTTGGCGGA

GCTGAGGCGCGCATTAACACGCAGTGGTTATTAACTAGCGGCACCACTGA

AGCTGATGCCTGGAAGAGCACGTTAGTGGGTCATGATACCTTCACTAAAG

TGGAACCTTCAGCTGCGTCATAATAATGACTCGAGACCTGCA

SAV-POS52
(SEQ ID NO: 32)
GGTTCAGCCATGGGTCATCACCACCACCATCACGGTGGCGCCAAAGCAGG

TATTACCGGTACCTGGTATAACCAGTTAGGCTCAACCTTTATTGTGACCG

CGGGAGCGAAAGGCGCCTTAACCGGTACCTACGAATCAGCTGTAGGAAAC

GCAAAATCACGCTACGTATTAACCGGTCGTTATGATAGCGCGCCGGCGAC

TAAAGGTAGCGGTACTGCTTTAGGTTGGACCGTAGCGTGGAAGAATAAGT

ATCGTAATGCGCACAGTGCTACCACTTGGTCAGGGCAGTACGTAGGGGGA

GCCAAAGCACGTATCAACACGCAGTGGTTATTAACATCAGGTACCACCAA

AGCGAAAGCCTGGAAGAGCACGTTAGTGGGTCATGATACCTTCACTAAAG

TGAAACCTTCAGCTGCGTCATAATAATGACTCGAGACCTGCA

Polynucleotide sequence homologous to the above sequences are also within the scope of the present invention. In certain embodiments, the polynucleotide sequence include a stretch of 50, 100, or 150 nucleotides that are 60%, 70%, 80%, 90%, 95%, 98%, 99%, or 100% homologous to any one of the above sequence. The present invention also includes sequence where one or more nucleotides is inserted or deleted from one of the above sequences. Any polynucleotide sequence with a mutation as shown in any of the sequences above is considered part of the invention. In certain embodiments, the sequence includes 2, 3, 4, 5, 6, 7, 8, 9, 10, or more mutations as shown in any of the sequences above.

The present invention also provides vector (e.g., plasmids, cosmids, viruses, etc.) that comprise any of the inventive sequences herein or any other sequence (DNA or protein) modified using the inventive system. In certain embodiments, the vector includes elements such as promoter, enhancer, ribosomal binding sites, etc. sequences useful in overexpressing the inventive streptavidin variant in a cell. The invention also includes cells comprising the inventive sequences or vectors. In certain embodiments, the cells overexpress the variant streptavidin. The cells may be bacterial cells (e.g., E. coli), fungal cells (e.g., P. pastoris), yeast cells (e.g., S. cerevisiae), mammalian cells (e.g., CHO cells), or human cells.

The inventive system has been used to created variants of glutathione-S-transferase (GST). These variants have been shown to retain the catalytic activity of wild type GST. The amino acid sequence of this wild type GST is as follows:

(SEQ ID NO: 33)
MGHHHHHHGGPPYTITYFPVRGRCEAMRMLLADQDQSWKEEVVTMETWPP

LKPSCLFRQLPKFQDGDLTLYQSNAILRHLGRSFGLYGKDQKEAALVDMV

NDGVEDLRCKYATLIYTNYEAGKEKYVKELPEHLKPFETLLSQNQGGQAF

VVGSQISFADYNLLDLLRIHQVLNPSCLDAFPLLSAYVARLSARPKIKAF

LASPEHVNRPINGNGKQ

Wild type GST has a theoretical net charge of +2. Using the inventive system, a variant with a theoretical net charge of −40 has been created. This variant catalyzes the addition of glutathione to chloronitrobenzene with a specific activity only 2.7-fold lower than that of wild type GST. Even after heating the variant to 100° C., the protein remained soluble, and the protein recovered 40% of its catalytic activity upon cooling.

The amino acid sequences of variants of GST include:

```
GST-NEG40
                                              (SEQ ID NO: 34)
MGHHHHHHGGPPYTITYFPVRGRCEAMRMLLADQDQSWEEEVVTMETWPP

LKPSCLFRQLPKFQDGDLTLYQSNAILRHLGRSFGLYGEDEEEAALVDMV

NDGVEDLRCKYATLIYTDYEAGKEEYVEELPEHLKPFETLLSENEGGEAF

VVGSEISFADYNLLDLLRIHQVLNPSCLDAFPLLSAYVARLSARPEIEAF

LASPEHVDRPINGNGKQ

GST-POS50
                                              (SEQ ID NO: 35)
MGHHHHHHGGPPYTITYFPVRGRCEAMRMLLADQKQSWKEEVVTMKTWPP

LKPSCLFRQLPKFQDGKLTLYQSNAILRHLGRSFGLYGKKQKEAALVDMV

NDGVEDLRCKYATLIYTKYKAGKKKYVKKLPKHLKPFETLLSKNKGGKAF

VVGSKISFADYNLLDLLRIHQVLNPSCLKAFPLLSAYVARLSARPKIKAF

LASPEHVKRPINGNGKQ
```

As would be appreciated by one of skill in the art, homologous proteins are also considered to be within the scope of this invention. For example, any protein that includes a stretch of 20, 30, 40, 50, or 100 amino acids which are 60%, 70%, 80%, 90%, 95%, or 100% homologous to any of the above sequences is considered part of the invention. In addition, addition and deletion variants are also contemplated by the invention. In certain embodiments, any streptavidin with a mutated residue as shown in any of the above sequences is considered part of the invention. In certain embodiments, the sequence includes 2, 3, 4, 5, 6, 7, 8, 9, 10, or more mutations as shown in any of the sequences above.

Any DNA sequence that encodes the above GST variants is also included within the scope of the invention. Exemplary DNA sequences which encode each of the variants above are as follows:

```
GST-NEG40
                                              (SEQ ID NO: 36)
GGTTCAGCCATGGGTCATCACCACCACCATCACGGTGGCCCGCCGTACAC

CATTACATACTTTCCGGTACGTGGTCGTTGTGAAGCGATGCGTATGTTAT

TAGCGGACCAGGACCAATCATGGGAAGAAGAAGTAGTGACAATGGAAACC

TGGCCGCCGTTAAAGCCTAGCTGTTTATTCCGTCAATTACCGAAGTTTCA

GGATGGTGATTTAACCTTATACCAGTCTAACGCGATCTTACGTCATTTAG

GTCGCTCATTTGGTTTATACGGTGAAGATGAAGAAGAAGCAGCCTTAGTG

GATATGGTGAATGATGGCGTGGAAGACTTACGTTGTAAATACGCGACGTT

AATTTACACTGATTATGAAGCCGGTAAAGAGGAGTACGTGGAAGAATTAC

CTGAACACCTGAAGCCGTTTGAAACATTACTGAGCGAAAATGAAGGAGGT

GAGGCGTTCGTAGTTGGTAGCGAAATTAGCTTCGCTGATTATAACTTATT

AGACTTATTACGCATTCACCAGGTTTTAAATCCTAGCTGTTTAGACGCTT

TCCCGTTACTGAGCGCATATGTAGCGCGCCTGAGCGCCCGTCCGAAATT

GAAGCTTTCTTAGCGTCACCTGAACACGTAGACCGCCCGATTAACGGAAA

CGGCAAGCAGTAATAATGAGGTACCACCTGCA

GST-POS50
                                              (SEQ ID NO: 37)
GGTTCAGCCATGGGTCATCACCACCACCATCACGGTGGCCCGCCGTACAC

CATTACATACTTTCCGGTACGTGGTCGTTGTGAAGCGATGCGTATGTTAT

TAGCGGACCAGAAACAATCATGGAAAGAAGAAGTAGTGACAATGAAGACC

TGGCCGCCGTTAAAGCCTAGCTGTTTATTCCGTCAATTACCGAAGTTTCA

GGATGGTAAATTAACCTTATACCAGTCTAACGCGATCTTACGTCATTTAG

GTCGCTCATTTGGTTTATACGGTAAGAAGCAGAAAGAAGCAGCCTTAGTG

GATATGGTGAATGATGGCGTGGAAGACTTACGTTGTAAATACGCGACGTT

AATTTACACTAAATATAAAGCCGGTAAAAAGAAGTACGTGAAAAAATTAC

CTAAACACCTGAAGCCGTTTGAAACATTACTGAGCAAAAATAAAGGAGGT

AAGGCGTTCGTAGTTGGTAGCAAGATTAGCTTCGCTGATTATAACTTATT

AGACTTATTACGCATTCACCAGGTTTTAAATCCTAGCTGTTTAAAGGCTT

TCCCGTTACTGAGCGCATATGTAGCGCGCCTGAGCGCCCGTCCGAAGATC

AAAGCTTTCTTAGCGTCACCTGAACACGTGAAGCGCCCGATTAACGGAAA

CGGCAAGCAGTAATAATGAGGTACCACCTGCA
```

The present invention also provides vector (e.g., plasmids, cosmids, viruses, etc.) that comprise any of the inventive sequences herein or any other sequence (DNA or protein) modified using the inventive system. In certain embodiments, the vector includes elements such as promoter, enhancer, ribosomal binding sites, etc. sequences useful in overexpressing the inventive GST variant in a cell. The invention also includes cells comprising the inventive sequences or vectors. In certain embodiments, the cells overexpress the variant GST. The cells may be bacterial cells (e.g., *E. coli*), fungal cells (e.g., *P. pastoris*), yeast cells (e.g., *S. cerevisiae*), mammalian cells (e.g., CHO cells), or human cells.

The present invention also includes kits for modifying proteins of interest to produce more stable variants of the protein. These kits typically include all or most of the reagents needed create a more stable variant of a protein. In certain embodiments, the kit includes computer software to aid a researcher in designing the more stable variant protein based on the inventive method. The kit may also include all of some of the following: reagents, primers, oligonucleotides, nucleotides, enzymes, buffers, cells, media, plates, tubes, instructions, vectors, etc. The research using the kit typically provides the DNA sequence for mutating to create the more stable variant. The contents are typically packaged for convenience use in a laboratory.

These and other aspects of the present invention will be further appreciated upon consideration of the following Examples, which are intended to illustrate certain particular embodiments of the invention but are not intended to limit its scope, as defined by the claims.

EXAMPLES

Example 1

Supercharging Proteins can Impart Extraordinary Resilience

Protein aggregation, a well known culprit in human disease (Cohen, F. E.; Kelly, J. W., *Nature* 2003, 426, (6968), 905-9; Chiti, F.; Dobson, C. M., *Annu Rev Biochem* 2006, 75, 333-66; each of which is incorporated herein by reference), is also a major problem facing the use of proteins as therapeutic or diagnostic agents (Frokjaer, S.; Otzen, D. E.,

*Nat Rev Drug Discov* 2005, 4, (4), 298-306; Fowler, S. B.; Poon, S.; Muff, R.; Chiti, F.; Dobson, C. M.; Zurdo, J., *Proc Natl Acad Sci USA* 2005, 102, (29), 10105-10; each of which is incorporated herein by reference). Insights into the protein aggregation problem have been garnered from the study of natural proteins. It has been known for some time that proteins are least soluble at their isoelectric point, where they bear a net charge of zero (Loeb, J., *J Gen Physiol* 1921, 4, 547-555; incorporated herein by reference). More recently, small differences in net charge (±3 charge units) have been shown to predict aggregation tendencies among variants of a globular protein (Chiti, F.; Stefani, M.; Taddei, N.; Ramponi, G.; Dobson, C. M., *Nature* 2003, 424, (6950), 805-8; incorporated herein by reference), and also among intrinsically disordered peptides (Pawar, A. P.; Dubay, K. F.; Zurdo, J.; Chiti, F.; Vendruscolo, M.; Dobson, C. M., *J Mol Biol* 2005, 350, (2), 379-92; incorporated herein by reference). Together with recent evidence that some proteins can tolerate significant changes in net charge (for example, the finding that carbonic anhydrase retains catalytic activity after exhaustive chemical acetylation of its surface lysines (Gudiksen et al., *J Am Chem Soc* 2005, 127, (13), 4707-14; incorporated herein by reference)), these observations led us to conclude that the solubility and aggregation resistance of some proteins might be significantly enhanced, without abolishing their folding or function, by extensively mutating their surfaces to dramatically increase their net charge, a process we refer to herein as "supercharging".

We began with a recently reported state-of-the-art variant of green fluorescent protein (GFP) called "superfolder GFP" (sfGFP), which has been highly optimized for folding efficiency and resistance to denaturants (Pedelacq et al., *Nat Biotechnol* 2006, 24, (1), 79-88; incorporated herein by reference). Superfolder GFP has a net charge of −7, similar to that of wild-type GFP. Guided by a simple algorithm to calculate solvent exposure of amino acids (see Materials and Methods), we designed a supercharged variant of GFP having a theoretical net charge of +36 by mutating 29 of its most solvent-exposed residues to positively charged amino acids (FIG. 1). The expression of genes encoding either sfGFP or GFP(+36) yielded intensely green-fluorescent bacteria. Following protein purification, the fluorescence properties of GFP(+36) were measured and found to be very similar to those of sfGFP. Encouraged by this finding, we designed and purified additional supercharged GFPs having net charges of +48, −25, and −30, all of which were also found to exhibit sfGFP-like fluorescence (FIG. 2a). All supercharged GFP variants showed circular dichroism spectra similar to that of sfGFP, indicating that the proteins have similar secondary structure content (FIG. 2b). The thermodynamic stabilities of the supercharged GFP variants were only modestly lower than that of sfGFP (1.0-4.1 kcal/mol, FIG. 2c and Table 1) despite the presence of as many as 36 mutations.

Although sfGFP is the product of a long history of GFP optimization (Giepmans et al., *Science* 2006, 312, (5771), 217-24; incorporated herein by reference), it remains susceptible to aggregation induced by thermal or chemical unfolding. Heating sfGFP to 100° C. induced its quantitative precipitation and the irreversible loss of fluorescence (FIG. 3a). In contrast, supercharged GFP(+36) and GFP(−30) remained soluble when heated to 100° C., and recovered significant fluorescence upon cooling (FIG. 3a). Importantly, while 40% 2,2,2-trifluoroethanol (TFE) induced the complete aggregation of sfGFP at 25° C. within minutes, the +36 and −30 supercharged GFP variants suffered no significant aggregation or loss of fluorescence under the same conditions for hours (FIG. 3b).

Figure 3C:
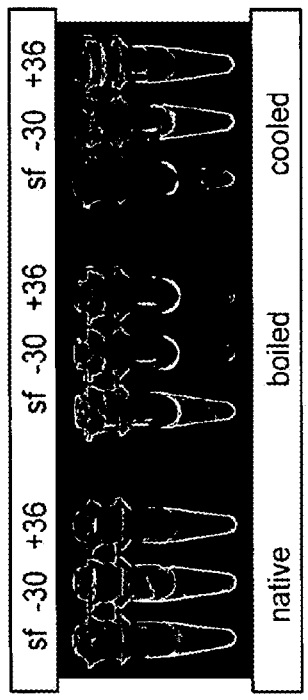
Figure 3B:
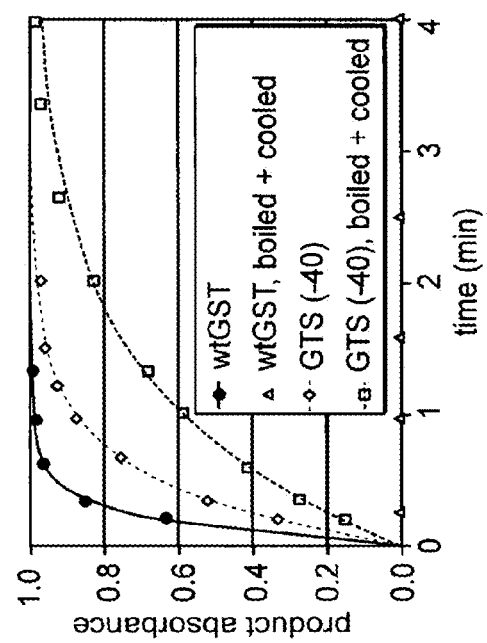

In addition to this remarkable aggregation resistance, supercharged GFP variants show a strong, reversible avidity for highly charged macromolecules of the opposite charge (FIG. 3c). When mixed together in 1:1 stoichiometry, GFP (+36) and GFP(−30) immediately formed a green fluorescent co-precipitate, indicating the association of folded proteins. GFP(+36) similarly co-precipitated with high concentrations of RNA or DNA. The addition of NaCl was sufficient to dissolve these complexes, consistent with the electrostatic basis of their formation. In contrast, sfGFP was unaffected by the addition of GFP(−30), RNA, or DNA (FIG. 3c).

We next sought to determine whether the supercharging principle could apply to proteins other than GFP, which is monomeric and has a well-shielded fluorophore. To this end, we applied the supercharging process to two proteins unrelated to GFP. Streptavidin is a tetramer with a total net charge of −4. Using the solvent-exposure algorithm, we designed two supercharged streptavidin variants with net charges of −40 or +52. Both supercharged streptavidin variants were capable of forming soluble tetramers that bind biotin, albeit with reduced affinity.

Figure 3D:
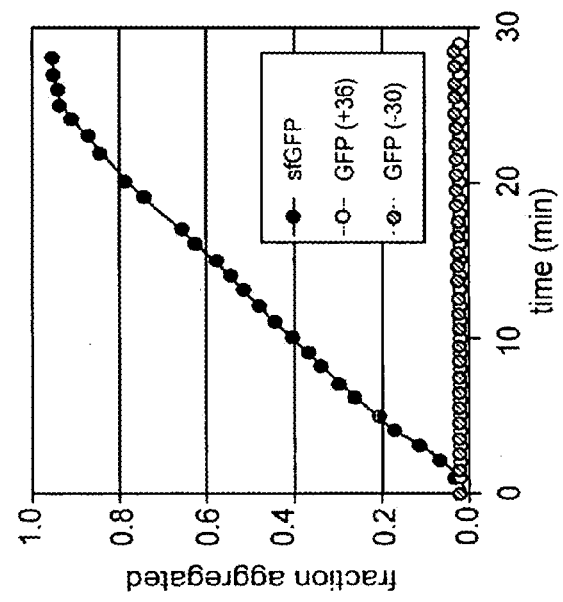
Figure 4B:
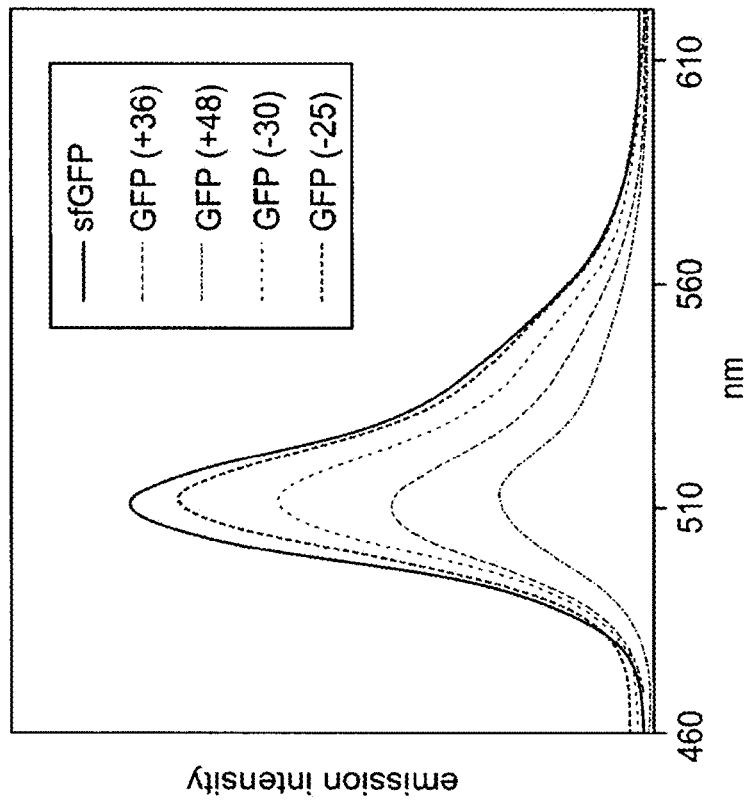
FIG. 4. (a) Excitation and (b) emission spectra of GFP variants. Each sample contained an equal amount of protein as quantitated by chromophore absorbance at 490 nm.
Figure 4A:
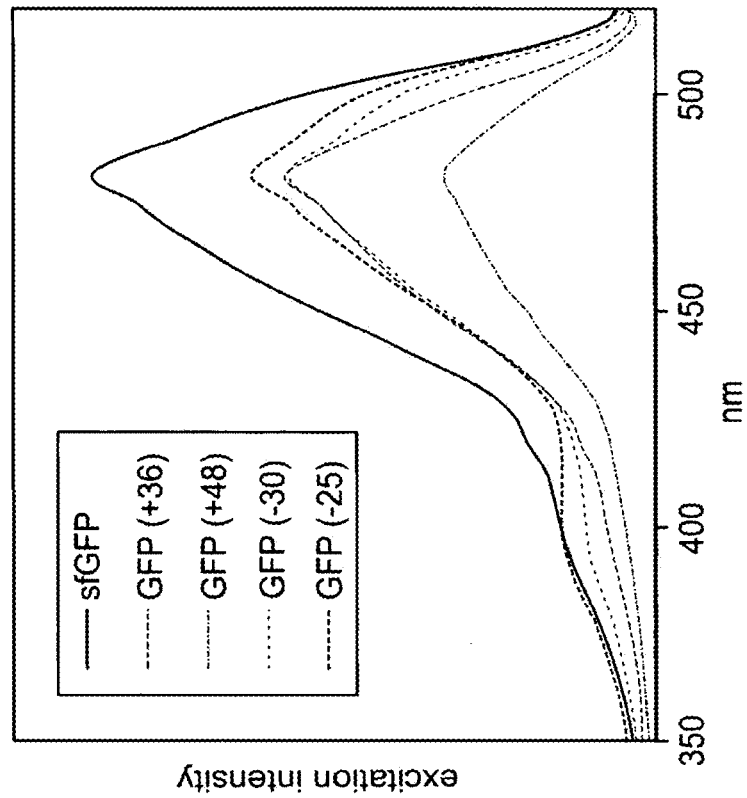
Figure 5:
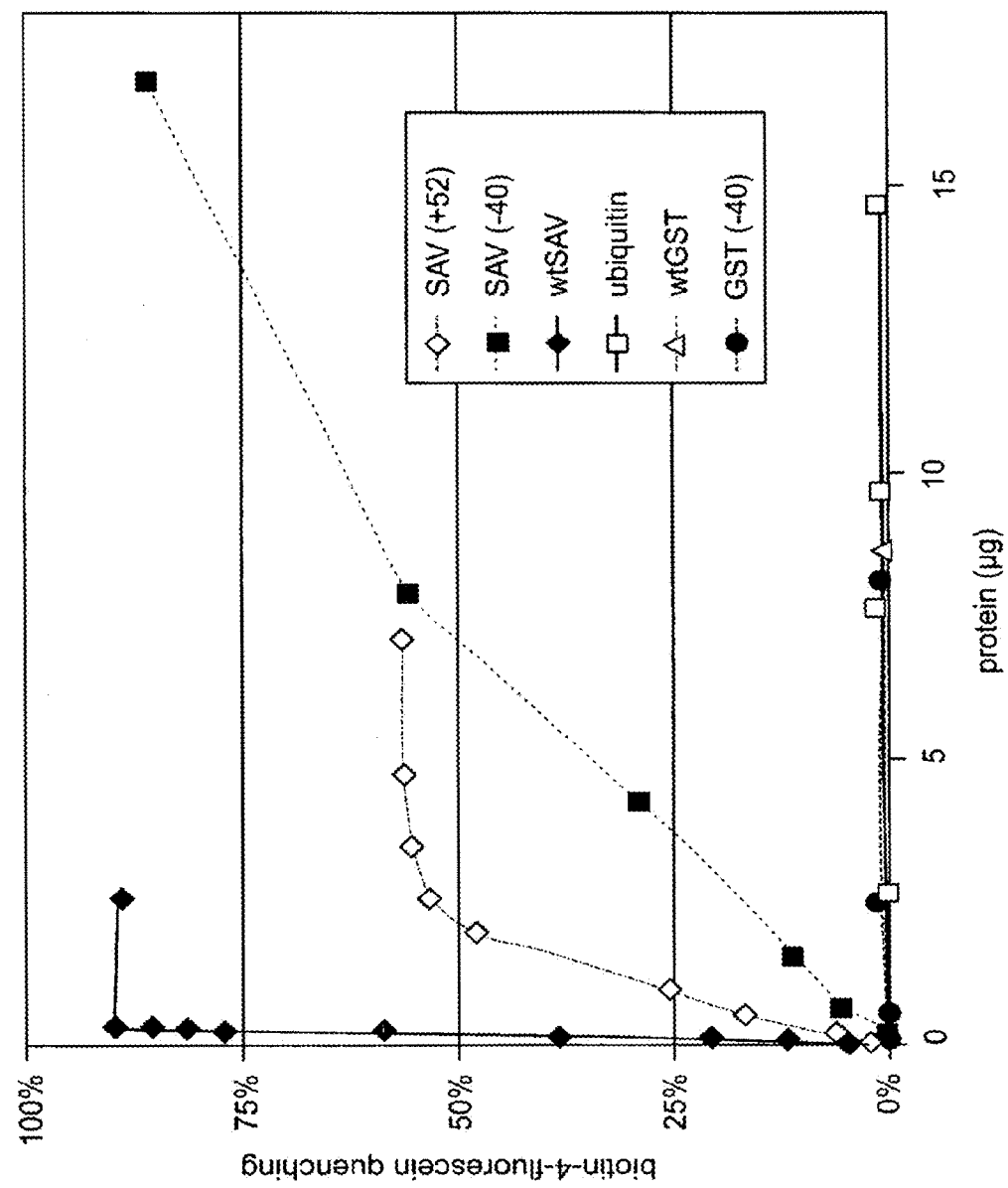
FIG. 5. Biotin-binding activity of streptavidin variants, measured as described previously (Kada et al., Rapid estimation of avidin and streptavidin by fluorescence quenching or fluorescence polarization. *Biochim. Biophys. Acta* 1427, 44-48 (1999); incorporated herein by reference) by monitoring binding-dependent of biotin-4-fluorescein (Invitrogen). Protein samples were titrated into 0.3 µM biotin-4-fluorescein (B4F), 100 mM NaCl, 1 mM EDTA, 0.1 mg/mL bovine serum albumin (BSA), 50 mM potassium phosphate pH 7.5. Quenching of fluorescence at 526 nm was measured on a Perkin-Elmer LS50B luminescence spectrometer with excitation at 470 nm. Measurements were normalized to control titrations that contained a 600-fold excess of non-fluorescent biotin. The three proteins in the bottom of the legend are included as negative controls.

Glutathione-S-transferase (GST), a dimer with a total net charge of +2, was supercharged to yield a dimer with net charge of −40 that catalyzed the addition of glutathione to chlorodinitrobenzene with a specific activity only 2.7-fold lower than that of wild-type GST (FIG. 3d). Moreover, the supercharged streptavidins and supercharged GST remained soluble when heated to 100° C., in contrast to their wild-type counterparts, which, like sfGFP, precipitated quantitatively and irreversibly (Table 1). In addition, GST(−40) recovered 40% of its catalytic activity upon cooling (FIG. 3d).

In summary, we have demonstrated that monomeric and multimeric proteins of varying structures and functions can be "supercharged" by simply replacing their most solvent-exposed residues with like-charged amino acids. Supercharging profoundly alters the intermolecular properties of proteins, imparting remarkable aggregation resistance and the ability to associate in folded form with oppositely charged macromolecules like "molecular Velcro." We note that these unusual intermolecular properties arise from high net charge, rather than from the total number of charged amino acids, which was not significantly changed by the supercharging process (Table 1).

In contrast to these dramatic intermolecular effects, the intramolecular properties of the seven supercharged proteins studied here, including folding, fluorescence, ligand binding, and enzymatic catalysis, remained largely intact. Supercharging therefore may represent a useful approach for reducing the aggregation tendency and improving the solubility of proteins without abolishing their function. These principles may be particularly useful in de novo protein design efforts, where unpredictable protein handling properties including aggregation remain a significant challenge. In light of the above results of supercharging natural proteins, it is tempting to speculate that the aggregation resistance of designed proteins could also be improved by biasing the design process to increase the frequency of like-charged amino acids at positions predicted to lie on the outside of the folded protein.

Protein supercharging illustrates the remarkable plasticity of protein surfaces and highlights the opportunities that arise from the mutational tolerance of solvent-exposed residues. For example, it was recently shown that the thermodynamic stability of some proteins can be enhanced by rationally engineering charge-charge interactions (Strickler et al., *Biochemistry* 2006, 45, (9), 2761-6; incorporated herein by reference). Protein supercharging demonstrates how this plasticity can be exploited in a different way to impart extraordinary resistance to protein aggregation. Our findings are consistent with the results of a complementary study in which removal of all charges from ubiquitin left its folding intact but significantly impaired its solubility (Loladze et al, *Protein Sci* 2002, 11, (1), 174-7; incorporated herein by reference).

These observations may also illuminate the modest net-charge distribution of natural proteins (Knight et al., *Proc Natl Acad Sci USA* 2004, 101, (22), 8390-5; Gitlin et al., *Angew Chem Int Ed Engl* 2006, 45, (19), 3022-60; each of which is incorporated herein by reference): the net charge of 84% of Protein Data Bank (PDB) polypeptides, for example, falls within ±10. Our results argue against the hypothesis that high net charge creates sufficient electrostatic repulsion to force unfolding. Indeed, GFP(+48) has a higher positive net charge than any polypeptide currently in the PDB, yet retains the ability to fold and fluoresce. Instead, our findings suggest that nonspecific intermolecular adhesions may have disfavored the evolution of too many highly charged natural proteins. Almost all natural proteins with very high net charge, such as ribosomal proteins L3 (+36) and L15 (+44), which bind RNA, or calsequestrin (−80), which binds calcium cations, associate with oppositely charged species as part of their essential cellular functions.

Materials and Methods

Design Procedure and Supercharged Protein Sequences.

Solvent-exposed residues (shown in grey below) were identified from published structural data (Weber, P. C., Ohlendorf, D. H., Wendoloski, J. J. & Salemme, F. R. Structural origins of high-affinity biotin binding to streptavidin. *Science* 243, 85-88 (1989); Dirr, H., Reinemer, P. & Huber, R. Refined crystal structure of porcine class Pi glutathione S-transferase (pGST P1-1) at 2.1 A resolution. *J Mol Biol* 243, 72-92 (1994); Pedelacq, J. D., Cabantous, S., Tran, T., Terwilliger, T. C. & Waldo, G. S. Engineering and characterization of a superfolder green fluorescent protein. *Nat Biotechnol* 24, 79-88 (2006); each of which is incorporated herein by reference) as those having AvNAPSA<150, where AvNAPSA is average neighbor atoms (within 10 Å) per sidechain atom. Charged or highly polar solvent-exposed residues (DERKNQ) were mutated either to Asp or Glu, for negative-supercharging (red); or to Lys or Arg, for positive-supercharging (blue). Additional surface-exposed positions to mutate in green fluorescent protein (GFP) variants were chosen on the basis of sequence variability at these positions among GFP homologues. The supercharging design process for streptavidin (SAV) and glutathione-S-transferase (GST) was fully automated: residues were first sorted by solvent exposure, and then the most solvent-exposed charged or highly polar residues were mutated either to Lys for positive supercharging, or to Glu (unless the starting residue was Asn, in which case to Asp) for negative supercharging.

```
              1
SAV(-40)   MGHHHHHHGGAEAGITGTWYNQLGSTFIVTAGADGALTGTYESAVGAES VLTGRYDSAPATDGSGTA
wtSAV               AAEAGITGTWYNQLGSTFIVTAGADGALTGTYESAVGNAESRYVLTGRYDSAPATDGSGTA
SAV(+52)   MGHHHHHHGGA AGITGTWYNQLGSTFIVTAGA GALTGTYESAVGNA RYVLTGRYDSAPAT SGTA

71
SAV(-40)   LGWTVAWKN Y NAHSATTWSGQYVGGAEARINTQWLLTSGTTEA AWKSTLVGHDTFTKV PSAAS
wtSAV      LGWTVAWKNNYRNAHSATTWSGQYVGGAEARINTQWLLTSGTTEANAWKSTLVGHDTFTKVKPSAAS
SAV(+52)   LGWTVAWKN YRNAHSATTWSGQYVGGA ARINTQWLLTSGTT A AWKSTLVGHDTFTKVKPSAAS

SAV(-40) (SEQ ID NO: 29); wtSAV (SEQ ID NO: 28); and SAV(+52) (SEQ ID NO: 30).

1
GST(-40)   MGHHHHHHGGPPYTITYFPVRGRCEAMRMLLADQDQSW EEVVTMETWPPLKPSCLFRQLPKFQDGDLTLYQSNA
wtGST      MGHHHHHHGGPPYTITYFPVRGRCEAMRMLLADQDQSWKEEVVTMETWPPLKPSCLFRQLPKFQDGDLTLYQSNA
GST(+50)   MGHHHHHHGGPPYTITYFPVRGRCEAMRMLLADQ QSWKEEVVTM TWPPLKPSCLFRQLPKFQDG TLYQSNA

75
GST(-40)   ILRHLGRSFGLYG D  EAALVDMVNDGVEDLRCKYATLIYT YEAGKE YV ELPEHLKPFETLLS N GG AF
wtGST      ILRHLGRSFGLYGKDQKEAALVDMVNDGVEDLRCKYATLIYTNYEAGKEKYVKELPEHLKPFETLLSQNQGGQAF
GST(+50)   ILRHLGRSFGLYGK QKEAALVDMVNDGVEDLRCKYATLIYT Y AGK KYVK P HLKPFETLLS N G AF

151
GST(-40)   VVGS ISFADYNLLDLLRIHQVLNPSCLDAFPLLSAYVARLSARP  AFLASPEHV RPINGNGKQ
wtGST      VVGSQISFADYNLLDLLRIHQVLNPSCLDAFPLLSAYVARLSARPKIKAFLASPEHVNRPINGNGKQ
GST(+50)   VVGS ISFADYNLLDLLRIHQVLNPSCL AFPLLSAYVARLSARPKIKAFLASPEHV PINGNGKQ

GST(-40) (SEQ ID NO: 34); wtGST (SEQ ID NO: 33); and GST(+50) (SEQ ID NO: 35).
```

Protein Expression and Purification.

Synthetic genes optimized for *E. coli* codon usage were purchased from DNA 2.0, cloned into a pET expression vector (Novagen), and overexpressed in *E. coli* BL21(DE3) pLysS for 5-10 hours at 15° C. Cells were harvested by centrifugation and lysed by sonication. Proteins were purified by Ni-NTA agarose chromotography (Qiagen), buffer-exchanged into 100 mM NaCl, 50 mM potassium phosphate pH 7.5, and concentrated by ultrafiltration (Millipore). All GFP variants were purified under native conditions. Wild-type streptavidin was purchased from Promega. Supercharged streptavidin variants were purified under denaturing conditions and refolded as reported previously for wild-type streptavidin (Thompson et al. Construction and expression of a synthetic streptavidin-encoding gene in *Escherichia coli. Gene* 136, 243-246 (1993); incorporated herein by reference), as was supercharged GST. Wild-type GST was purified under either native or denaturing conditions, yielding protein of comparable activity.

Electrostatic Surface Potential Calculations (FIG. 1b).

Models of −30 and +48 supercharged GFP variants were based on the crystal structure of superfolder GFP (Pedelacq et al., Engineering and characterization of a superfolder green fluorescent protein. *Nat Biotechnol* 24, 79-88 (2006); incorporated herein by reference). Electrostatic potentials were calculated using APBS (Baker et al., Electrostatics of nanosystems: application to microtubules and the ribosome. *Proc Natl Acad Sci USA* 98, 10037-10041 (2001); incorporated herein by reference) and rendered with PyMol (Delano, W. L., The PyMOL Molecular Graphics System, www[dot]pymol[dot]org (2002); incorporated herein by reference) using a scale of −25 kT/e (red) to +25 kT/e (blue).

Protein Staining and UV-Induced Fluorescence (FIG. 2a).

0.2 μg of each GFP variant was analyzed by electrophoresis in a 10% denaturing polyacrylamide gel and stained with Coomassie brilliant blue dye. 0.2 μg of the same protein samples in 25 mM Tris pH 8.0 with 100 mM NaCl was placed in a 0.2 mL Eppendorf tube and photographed under UV light (360 nm).

Thermal Denaturation and Aggregation (FIG. 3a).

Purified GFP variants were diluted to 2 mg/mL in 25 mM Tris pH 8.0, 100 mM NaCl, and 10 mM beta-mercaptoethanol (BME), then photographed under UV illumination ("native"). The samples were heated to 100° C. for 1 minute, then photographed again under UV illumination ("boiled"). Finally, the samples were cooled 2 h at room temperature and photographed again under UV illumination ("cooled").

Chemically Induced Aggregation (FIG. 3b).

2,2,2-trifluoroethanol (TFE) was added to produce solutions with 1.5 mg/mL protein, 25 mM Tris pH 7.0, 10 mM BME, and 40% TFE. Aggregation at 25° C. was monitored by right-angle light scattering.

Size-Exclusion Chromatography (Table 1).

The multimeric state of SAV and GST variants was determined by analyzing 20-50 μg of protein on a Superdex 75 gel-filtration column. Buffer was 100 mM NaCl, 50 mM potassium phosphate pH 7.5. Molecular weights were determined by comparison with a set of monomeric protein standards of known molecular weights analyzed separately under identical conditions.

TABLE 1

Calculated and experimentally determined protein properties.

| name | MW (kD) | length (aa) | $n_{pos}$ | $n_{neg}$ | $n_{charged}$ | $Q_{net}$ | pI | ΔG (kcal/mol)[a] | native MW (kD)[b] | % soluble after boiling[c] |
|---|---|---|---|---|---|---|---|---|---|---|
| GFP (−30) | 27.8 | 248 | 19 | 49 | 68 | −30 | 4.8 | 10.2 | n.d. | 98 |
| GFP (−25) | 27.8 | 248 | 21 | 46 | 67 | −25 | 5.0 | n.d. | n.d. | n.d. |
| sfGFP | 27.8 | 248 | 27 | 34 | 61 | −7 | 6.6 | 11.2 | n.d. | 4 |
| GFP (+36) | 28.5 | 248 | 56 | 20 | 76 | +36 | 10.4 | 8.8 | n.d. | 97 |
| GFP (+48) | 28.6 | 248 | 63 | 15 | 78 | +48 | 10.8 | 7.1 | n.d. | n.d. |
| SAV (−40) | 14.3 | 137 | 5 | 15 | 20 | −10 | 5.1 | n.d. | 55 ± 5 (tetramer) | 99 |
| wtSAV | 13.3 | 128 | 8 | 9 | 17 | −1 | 6.5 | n.d. | 50 ± 5 (tetramer) | 7 |
| SAV (+52) | 14.5 | 137 | 16 | 3 | 19 | +13 | 10.3 | n.d. | 55 ± 5 (tetramer) | 97 |
| GST (−40) | 24.7 | 217 | 17 | 37 | 54 | −20 | 4.8 | n.d. | 50 ± 5 (dimer) | 96 |
| wtGST | 24.6 | 217 | 24 | 23 | 47 | +1 | 7.9 | n.d. | 50 ± 5 (dimer) | 3 |
| GST (+50)[d] | 24.7 | 217 | 39 | 14 | 53 | +25 | 10.0 | n.d. | n.d. | n.d. |

$n_{pos}$, number of positively charged amino acids (per monomer)
$n_{neg}$, number of negatively charged amino acids
$n_{charged}$, total number of charged amino acids
$Q_{net}$, theroretical net charge at neutral pH
pI, calculated isoelectric point
n.d., not determined
[a]measured by guanidinium denaturation (FIG. 2c).
[b]measured by size-exclusion chromatography.
[c]percent protein remaining in supernatant after 5 min at 100° C., cooling to 25° C., and brief centrifugation.
[d]protein failed to express in *E. coli*.

OTHER EMBODIMENTS

Those of ordinary skill in the art will readily appreciate that the foregoing represents merely certain preferred embodiments of the invention. Various changes and modifications to the procedures and compositions described above can be made without departing from the spirit or scope of the present invention, as set forth in the following claims.

APPENDIX A

```
#!/usr/local/bin/perl
###############################################################

# avnapsa

# prints list of AvNAPSA values for the specified PDB

# Mike Lawrence/Kevin Phillips  3/17/2006

###############################################################
```

APPENDIX A-continued

```
sub show_usage
{
print "\n",
"Usage: avnapsa <start_pdb> [params]\n",
"   -3    use 3-letter aa abbreviations (default)\n",
"   -1    use 1-letter aa abbreviations\n",
"   -onecol   print one column only (i.e. only the AvNAPSA results)\n\n";
}
########## global variables ################################
@atoms;
    # fields loaded from PDB:
        # type
        # atomNum
        # atomName
        # resName
        # chain
        # resNum
        # x, y, z
    # computed fields
        # neighborCount
@distances;
@residues;
    # fields copied from PDB
        # resNum (PDB numbering)
        # resName
    # computed fields
        # avNapsa
#######################################################################
parse command line
$use3or1 = 3;
$onecol_flag = 0;
$start_pdb = $ARGV[0];
for (my $a = 1; $a < @ARGV; ++$a)
{
        if ($ARGV[$a] eq "-1") { $use3or1 = 1; }
    elsif ($ARGV[$a] eq "-3") { $use3or1 = 3; }
    elsif ($ARGV[$a] eq "-onecol") { $onecol_flag = 1; }
    else { show_usage( ); die "Invalid argument $ARGV[$a]\n"; }
}
unless (lc $start_pdb =~ /\.pdb/) { show_usage( ); die "No starting pdb
specified.\n"; }
read PDB and compute molecular parameters
read_PDB($start_pdb);
tabulate_residues( );
$nres = @residues;
compute_distances( );
compute_neighbor_counts( );
compute_residue_avNapsa( );
print_residues( );
exit;

# print_residues

sub print_residues
{
    for (my $r = 0; $r < @residues; $r++)
    {
      my $name = $residues[$r]{resName};
        $name = toggle31($name) if ($use3or1 == 1);
        printf "%d %s AvNAPSA ", $residues[$r]{resNum}, $name unless
$onecol_flag;
        printf "%.0f\n", $residues[$r]{avNapsa};
    }
    print "\nNum residues = ", $#residues+1, "\n\n" unless $onecol_flag;
}

# tabulate_residues

# goes through list of atoms and makes a list of amino acid residues
# and stores it in global variable @residues

sub tabulate_residues
{
    for ($a = 0; $a < @atoms; $a++)
    {
      $resNum = $atoms[$a]{resNum};
        if ( ! resNum_exists($resNum) )
        {
            push @residues,
```

APPENDIX A-continued

```perl
            {
                    resNum => $resNum,
                    resName => $atoms[$a]{resName}
            };
        }
    }
}

# resNum_exists

# returns 1 if resNum is contained in @residues

sub resNum_exists($)
{
    my ($resNum) = @_;
    for ($r = 0; $r < @residues; $r++)
    {
        return 1 if ($residues[$r]{resNum} == $resNum);
    }
    return 0;
}

# resNum_to_resindex

# converts PDB numbering to index in @residues

sub resNum_to_resindex($)
{
    my ($resNum) = @_;
    for ($r = 0; $r < @residues; $r++)
    {
        return $r if ($residues[$r]{resNum} == $resNum);
    }
    return "none";
}

# readPDB(filename)

# reads the atoms from a PDB and returns them as an array of hashes

sub read_PDB($)
{
    my ($filename) = @_;
    open (PDB, $filename) or die("Could not open $filename\n");
    $#atoms = -1;         # clear atoms storage
# read the file
    foreach (<PDB>) {
        my $type = trim(substr($_, 0,6));          # RTyp field is columns 1-6
          next unless ($type eq "ATOM" || $type eq "HETATM");
        my $resName = trim(substr($_, 17, 3));     # Res field is columns 18-20
        my $atomName = trim(substr($_, 12, 4));    # Atm field is columns 13-16
        next if uc $resName eq "HOH";              # omit waters
        next if uc $atomName =~ /^[0-9]*H/;        # omit protons
        # add a hash to the array, containing data from this record of the PDB
        push @atoms, {
            type =>        $type,
            resName =>     $resName,
            atomName =>    $atomName,
            atomNum =>     trim(substr($_, 6,5)),   # Num field is columns 7-11
            chain =>       trim(substr($_, 21,1)),  # Chain field is column 22
            resNum =>      trim(substr($_, 22,4)),  # ResNo field is columns 23-26
            x =>           trim(substr($_, 30,8)),  # X field is columns 31-38
            y =>           trim(substr($_, 38,8)),  # Y field is columns 39-46
            z =>           trim(substr($_, 46,8))   # Z field is columns 37-54
        };
    }
    close(PDB);
}

# trim

# removes whitespace from start and end of string

sub trim($)
{
    my ($string) = @_;      # retrieve the passed argument
    $string =~ s/^\s+//;    # remove leading whitespace
    $string =~ s/\s+$//;    # remove trailing whitespace
```

APPENDIX A-continued

```perl
    return $string;
}

# is_number

# returns 1 if passed argument is a number (allows whitespace, negative, and
decimal point)
# returns 0 if passed argument is blank or not a number

A
sub is_number($)
{
    $_ = shift;
    s/^\s+//;
    s/\s+$//;
    return 1 if /^-?[0-9]+$/ || /^-?[0-9]*\.[0-9]+$/ || /^-?[0-9]+\.[0-9]*$/;
    return 0;
}

# inter_residue_distance

# returns the minimum distance between any atoms of the specified residues
# (residues are specified according to index in @residues)

sub inter_residue_distance($, $)
{
    my ($r1, $r2) = @_;
    ## convert to PDB numbering
    my $resNum1 = $residues[$r1]{resNum};
    my $resNum2 = $residues[$r2]{resNum};
    my $min_dist = 1000000;
    for ($a1 = 0; $a1 < @atoms; ++$a1)
    {
        next unless ( $atoms[$a1]{resNum} == $resNum1 );
        for ($a2 = 0; $a2 < @atoms; ++$a2)
        {
            next unless ( $atoms[$a2]{resNum} == $resNum2 );
            my $dist = $distances[$a1][$a2];
            $min_dist = $dist if ($dist < $min_dist);
        }
    }
    return $min_dist;
}

# compute_distances

# computes the distances between all atoms

sub compute_distances
{
    for(my $atom1=0; $atom1 < @atoms; $atom1++)
    {
      for(my $atom2=$atom1; $atom2 < @atoms; $atom2++)
      {
            my ($x1,$y1,$z1) = ($atoms[$atom1]->{x}, $atoms[$atom1]->{y}, $atoms[$atom1]->{z});
            my ($x2,$y2,$z2) = ($atoms[$atom2]->{x}, $atoms[$atom2]->{y}, $atoms[$atom2]->{z});
            my $distance = sqrt(($x1-$x2)**2 + ($y1-$y2)**2 + ($z1-$z2)**2);
            $distances[$atom1][$atom2] = $distance;
            $distances[$atom2][$atom1] = $distance;
      }
    }
}

# compute_neighbor_counts

# computes the number of neighbors that each atom has.
# paramter is the cutoff, in Angstroms, for atomic neighborhood

sub compute_neighbor_counts
{
    $DISTANCE_CUTOFF = 10;       # criterion for neighborhood, in Angstroms
    for ($atom1=0; $atom1 < @atoms; $atom1++)
    {
      my $count = 0;
      for ($atom2=0; $atom2 < @atoms; $atom2++)
      {
            $count++ if ($distances[$atom1][$atom2] <= $DISTANCE_CUTOFF
                && $atom1 != $atom2);
```

APPENDIX A-continued

```perl
        }
        $atoms[$atom1]{neighborCount} = $count;
    }
}

# compute_residue_avNapsa

# for each residue, compute
# Average Neighbor Atoms Per Sidechain Atom (AvNAPSA)
# (sidechain atoms are all those except N, C, O, CA)
# for glycines, just use CA

sub compute_residue_avNapsa
{
    for (my $r = 0; $r < @residues; $r++)
    {
        my $numSideChainAtoms = 0;
        my $totalNeighbors = 0;
        my $resName = $residues[$r]{resName};
        my $resNum = $residues[$r]{resNum};
A
        for (my $a = 0; $a < @atoms; $a++)
          {
          if ($atoms[$a]{resNum} == $resNum)
            {
            my $atomName = $atoms[$a]{atomName};
              if (
                  (       $atomName ne "C"
                     && $atomName ne "O"
                     && $atomName ne "N"
                     && $atomName ne "CA"
                  )
                  || ( $atomName eq "CA" && $resName eq "GLY")
                 )
              {
              $numSideChainAtoms++;
              $totalNeighbors += $atoms[$a]{neighborCount};
              }
            }
          }
        my $avNapsa = $totalNeighbors / $numSideChainAtoms;
        $residues[$r]{avNapsa} = $avNapsa;
    }
}

# toggle31

# converts 3-letter abbrev to 1-letter
# or 1-letter abbrev to 3-letter

sub toggle31($)
{
    %conv3to1 = ( "ALA" => "A", "CYS" => "C", "SER" => "S", "LEU" => "L",
            "ILE" => "I", "PHE" => "F", "ARG" => "R", "ASN" => "N", "GLN" => "Q",
            "TYR" => "Y", "LYS" => "K", "ASP" => "D", "GLU" => "E", "VAL" => "V",
            "TRP" => "W", "MET" => "M", "HIS" => "H", "GLY" => "G", "PRO" => "P",
"THR" => "T" );
    %conv1to3 = reverse %conv3to1;
    my ($abbrev) = @_;
    $abbrev = uc $abbrev;
    return $conv1to3{$abbrev} if length ($abbrev) == 1;
    return $conv3to1{$abbrev} if length ($abbrev) == 3;
    die "in toggle31( ): invalid amino acid abbreviation $abbrev\n";
}

# is_aa

# returns 1 if passed argument is a 1-letter amino acid

sub is_aa($)
{
    my ($string) = @_;
    return 1 if (length toggle31($string) == 3);
    return 0;
}
```

What is claimed is:

1. A supercharged protein variant of a wild-type protein, wherein the supercharged protein variant comprises a modified primary amino acid sequence as compared to the wild-type sequence, resulting in a theoretical net charge on the supercharged protein variant of +10 to +52 at physiological pH, wherein the theoretical net charge at physiological pH of the supercharged protein variant is increased by at least +3 as compared to the theoretical net charge of the wild-type protein, wherein the wild-type protein is an immunoglobulin or a fragment thereof.

2. The supercharged protein of claim 1, wherein the theoretical net charge at physiological pH of the supercharged protein variant is increased by at least +4, at least +5, at least +10, at least +15, at least +20, at least +25, at least +30, or at least +35 as compared to the theoretical net charge of the wild-type sequence.

3. The supercharged protein variant of claim 1, wherein the theoretical net charge at physiological pH of the supercharged protein is within the range of +52 to +20, +52 to +30, or +52 to +40.

4. The supercharged protein variant of claim 1, wherein the supercharged protein variant retains at least 50%, at least 75%, at least 90%, or at least 95% of the activity of the wild-type protein.

5. The supercharged protein variant of claim 1, wherein the wild-type protein is an immunoglobulin.

6. The supercharged protein variant of claim 1, wherein the immunoglobulin or fragment thereof is human or humanized.

7. The supercharged protein variant of claim 1, wherein the variant is a fusion protein.

8. The supercharged protein variant of claim 7, wherein the fusion protein comprises a linker.

9. The supercharged protein variant of claim 1, wherein the modified primary amino acid sequence of the supercharged protein variant comprises a replacement of at least one charged surface residue of the wild-type protein with a different residue.

10. The supercharged protein variant of claim 1, wherein the modified primary amino acid sequence of the supercharged protein variant comprises a replacement of at least one surface residue of the wild-type protein with a lysine, histidine, or arginine residue.

11. The supercharged protein variant of claim 1, wherein the modified primary amino acid sequence of the supercharged protein variant comprises a replacement of at least two, at least five, at least ten, at least twenty, or at least thirty surface residues of the wild-type protein with a different residue.

12. A composition comprising the supercharged protein variant of claim 1.

13. The supercharged protein variant of claim 1, wherein the wild-type protein is a fragment of an immunoglobulin.

14. The supercharged protein variant of claim 1,
wherein the modified primary amino acid sequence comprises replacing a plurality of non-conserved, surface residues with a natural amino acid residue that is positively charged at physiological pH; and
wherein non-conserved, surface residues are identified by comparing the amino acid sequence of the protein with at least one other amino acid sequence of the protein from the same protein family or a different species, wherein a residue is non-conserved if less than or equal to 50% of the amino acid sequences have the same amino acid sequence in a particular position.

15. A method of preparing a supercharged protein variant of claim 1, the method comprising steps of:
identifying the surface residues of a protein of interest that are not highly conserved among other proteins related to the protein of interest; and
replacing a plurality of non-conserved, surface residues with an amino acid residue that is positively charged at physiological pH, or
replacing a plurality of non-conserved, surface residues with an amino acid residue that is negatively charged at physiological pH.

16. A supercharged protein variant of a wild-type protein, wherein the supercharged protein variant comprises a modified primary amino acid sequence as compared to the wild-type sequence, resulting in a theoretical net charge on the supercharged protein variant of −40 to −10 at physiological pH, wherein the theoretical net charge at physiological pH of the supercharged protein variant is decreased by at least −3 as compared to the theoretical net charge of the wild-type protein,
wherein the wild-type protein is an immunoglobulin or a fragment thereof.

17. The supercharged protein of claim 16, wherein the theoretical net charge at physiological pH of the supercharged protein variant is decreased by at least −4, at least −5, at least −10, at least −15, at least −20, at least −25, at least −30, or at least −35 as compared to the theoretical net charge of the wild-type sequence.

18. The supercharged protein variant of claim 16, wherein the theoretical net charge at physiological pH of the supercharged protein is within the range of −40 to −20 or −40 to −30.

19. The supercharged protein variant of claim 16, wherein the modified primary amino acid sequence of the supercharged protein variant comprises a replacement of at least one charged surface residue of the wild-type protein with a different residue.

20. The supercharged protein variant of claim 16, wherein the modified primary amino acid sequence of the supercharged protein variant comprises a replacement of at least one surface residue of the wild-type protein with an aspartate or glutamate residue.

21. The supercharged protein variant of claim 16, wherein the wild-type protein is an immunoglobulin.

22. The supercharged protein variant of claim 16, wherein the wild-type protein is a fragment of an immunoglobulin.

23. The supercharged protein variant of claim 16, wherein the immunoglobulin or fragment thereof is human or humanized.

24. The supercharged protein variant of claim 16,
wherein the modified primary amino acid sequence comprises replacing a plurality of non-conserved, surface residues with a natural amino acid residue that is positively charged at physiological pH; and
wherein non-conserved, surface residues are identified by comparing the amino acid sequence of the protein with at least one other amino acid sequence of the protein from the same protein family or a different species, wherein a residue is non-conserved if less than or equal to 50% of the amino acid sequences have the same amino acid sequence in a particular position.

25. A protein selected from:
a green fluorescent protein (+36 GFP) comprising the amino acid sequence: MGHHHHHHGGASKGERL-FRGKVPILVELKGDVNGHKFSVRGKGKGDAT-RGKLTLKFICTT GKLPVPWPTLVTTLTYGVQCF-SRYPKHMKRHDFFKSAMPKGYVQERTISFKKD-GKYKTRA EVKFEGRTLVNRIKLKGRDFKEKG-NILGHKLRYNFNSHKVYITADKRKNGIKAKFKI-RHNV KDGSVQLADHYQQNTPIGRGPVLLPRN-HYLSTRSKLSKDPKEKRDHMVLLEFVTAAGIKH GRDERYK (SEQ ID NO: 5);
a green fluorescent protein (+42 GFP) comprising the amino acid sequence: MGHHHHHHGGRSKGKRL-FRGKVPILVELKGDVNGHKFSVRGKGKGDATR-GKLTLKFICT TGKLPVPWPTLVTTLTYGVQCF-SRYPKHMKRHDFFKSAMPKGYVQERTISFKKD-GKYKTR AEVKFEGRTLVNRIKLKGRDFKEKG-NILGHKLRYNFNSHKVYITADKRKNGIKAKFKI-RHN VKDGSVQLADHYQQNTPIGRGPVLLPRK-HYLSTRSKLSKDPKEKRDHMVLLEFVTAAGIK HGRKERYK (SEQ ID NO: 6);
a green fluorescent protein (+48 GFP) comprising the amino acid sequence: MGHHHHHHGGRSKGKRL-FRGKVPILVKLKGDVNGHKFSVRGKGKGDATR-GKLTLKFICT TGKLPVPWPTLVTTLTYGVQCFS-RYPKHMKRHDFFKSAMPKGYVQERTISFKKDG-KYKTR AEVKFKGRTLVNRIKLKGRDFKEKGNI-LGHKLRYNFNSHKVYITADKRKNGIKAKFKIR-HN VKDGSVQLAKHYQQNTPIGRGPVLLPRKHY-LSTRSKLSKDPKEKRDHMVLLEFVTAAGIK HGRKERYK (SEQ ID NO: 27);
a green fluorescent protein (+49 GFP) comprising the amino acid sequence: MGHHHHHHGGRSKGKRL-FRGKVPILVKLKGDVNGHKFSVRGKGKG-DATRGKLTLKFICT TGKLPVPWPTLVTTLTYGV-QCFSRYPKHMKRHDFFKSAMPKGYVQERTIS-FKKDGKYKTR AEVKFKGRTLVNRIKLKGRD-FKEKGNILGHKLRYNFNSHKVYITADKRKN-GIKAKFKIRHN VKDGSVQLAKHYQQNTPIGRG-PVLLPRKHYLSTRSKLSKDPKEKRDHMV-LKEFVTAAGIK HGRKERYK (SEQ ID NO: 7);
a streptavidin (+52 SAV) comprising an amino acid sequence: MGHHHHHHGGAKAGITGTWYNQLG- STFIVTAGAKGALTGTYESAVGNAKSRYVLT-GRYD SAPATKGSGTALGWTVAWKNKYRNAH-SATTWSGQYVGGAKARINTQWLLTSGTTKAKA WKSTLVGHDTFTKVKPSAAS (SEQ ID NO: 30); and a glutathione-S-transferase (+50 GST) of amino acid sequence: MGHHHHHHGGPPYTITYFPVRGRCEA-MRMLLADQKQSWKEEVVTMKTWPPLKPSCL-FRQ LPKFQDGKLTLYQSNAILRHLGRSFGLYGK-KQKEAALVDMVNDGVEDLRCKYATLIYTKY KAGKKKYVKKLPKHLKPFETLLSKNKGGKAFV-VGSKISFADYNLLDLLRIHQVLNPSCLKA FPLL-SAYVARLSARPKIKAFLASPEHVKRPINGNGKQ (SEQ ID NO: 35).

26. A supercharged protein selected from:

a streptavidin protein (−40 SAV) comprising an amino acid sequence: MGHHHHHHGGAEAGITGTWYN-QLGSTFIVTAGADGALTGTYESAVGDAESEYV-LTGRYD SAPATDGSGTALGWTVAWKNDYENA-HSATTWSGQYVGGAEARINTQWLLTSGTTEA-DA WKSTLVGHDTFTKVEPSAAS (SEQ ID NO: 29);

a green fluorescent protein (−30 GFP) of amino acid sequence: MGHHHHHHGGASKGEELFDGVVPIL-VELDGDVNGHEFSVRGEGEGDATEGELTLK-FICTT GELPVPWPTLVTTLTYGVQCFSDYPDHM-DQHDFFKSAMPEGYVQERTISFKDDGTYKTRA EVKFEGDTLVNRIELKGIDFKEDGNILGHK-LEYNFNSHDVYITADKQENGIKAEFEIRHNVE DGSVQLADHYQQNTPIGDGPVLLPDDHYLSTE-SALSKDPNEDRDHMVLLEFVTAAGIDHG MDE-LYK (SEQ ID NO: 4);

a green fluorescent protein (−29 GFP) of amino acid sequence: MGHHHHHHGGASKGEELFDGEVPIL-VELDGDVNGHEFSVRGEGEGDATEGELTLK-FICTT GELPVPWPTLVTTLTYGVQCFSRYPDHM-DQHDFFKSAMPEGYVQERTISFKDDGTYKTRA EVKFEGDTLVNRIELKGIDFKEDGNILGHK-LEYNFNSHDVYITADKQENGIKAEFEIRHNVE DGSVQLADHYQQNTPIGDGPVLLPDDHYLSTE-SALSKDPNEDRDHMVLLEFVTAAGIDHG MDE-LYK (SEQ ID NO: 3);

a green fluorescent protein (−25 GFP) of amino acid sequence: MGHHHHHHGGASKGEELFTGVVPIL-VELDGDVNGHEFSVRGEGEGDATEGELTLK-FICTT GELPVPWPTLVTTLTYGVQCFSRYPDHM-KQHDFFKSAMPEGYVQERTISFKDDGTYKTRA EVKFEGDTLVNRIELKGIDFKEDGNILGHK-LEYNFNSHDVYITADKQENGIKAEFEIRHNVE DGSVQLADHYQQNTPIGDGPVLLPDDHYLSTE-SALSKDPNEDRDHMVLLEFVTAAGIDHG MDE-LYK (SEQ ID NO: 2); and a glutathione-S-transferase (−40 GST) of amino acid sequence: MGHHHHHHGGPPYTITYFPVRGRCEA-MRMLLADQDQSWEEEVVTMETWPPLKPSCL-FRQ LPKFQDGDLTLYQSNAILRHLGRSFGLY-GEDEEEAALVDMVNDGVEDLRCKYATLIYTDY EAGKEEYVEELPEHLKPFETLLSENEGGEAFV-VGSEISFADYNLLDLLRIHQVLNPSCLDAFP LLSAYVARLSARPEIEAFLASPEHVDRP-INGNGKQ (SEQ ID NO: 34).

* * * * *

UNITED STATES PATENT AND TRADEMARK OFFICE
CERTIFICATE OF CORRECTION

PATENT NO. : 9,434,774 B2  
APPLICATION NO. : 13/341231  
DATED : September 6, 2016  
INVENTOR(S) : David R. Liu et al.

Page 1 of 1

It is certified that error appears in the above-identified patent and that said Letters Patent is hereby corrected as shown below:

In the Specification

At Column 1, Lines 15-20, the paragraph:
"The work described herein was supported, in part, by grants from the National Institutes of Health (GM065400). The United States government may have certain rights in the invention."

Should be changed to:
--This invention was made with government support under GM065400 awarded by the National Institutes of Health. The government has certain rights in the invention.--

Signed and Sealed this
Twenty-seventh Day of August, 2024

Katherine Kelly Vidal
*Director of the United States Patent and Trademark Office*